(12) United States Patent
Cristau et al.

(10) Patent No.: US 9,220,266 B2
(45) Date of Patent: Dec. 29, 2015

(54) KETOHETEROARYLPIPERIDINE AND -PIPERAZINE DERIVATIVES AS FUNGICIDES

(75) Inventors: Pierre Cristau, Lyons (FR); Sebastian Hoffmann, Neuss (DE); Joachim Kluth, Langenfeld (DE); Thomas Seitz, Langenfeld (DE); Tomoki Tsuchiya, Düsseldorf (DE); Pierre Wasnaire, Düsseldorf (DE); Jürgen Benting, Leichlingen (DE); Ulrike Wachendorff-Neumann, Neuwied (DE)

(73) Assignee: Bayer Intellectual Property GmbH, Monheim (DE)

( * ) Notice: Subject to any disclaimer, the term of this patent is extended or adjusted under 35 U.S.C. 154(b) by 255 days.

(21) Appl. No.: 13/096,637

(22) Filed: Apr. 28, 2011

(65) Prior Publication Data

US 2011/0312999 A1 Dec. 22, 2011

Related U.S. Application Data

(60) Provisional application No. 61/328,806, filed on Apr. 28, 2010.

(30) Foreign Application Priority Data

Apr. 28, 2010 (EP) .................................... 10161264

(51) Int. Cl.
| | | |
|---|---|---|
| A01N 43/40 | (2006.01) | |
| C07D 419/04 | (2006.01) | |
| A01P 3/00 | (2006.01) | |
| A01N 43/78 | (2006.01) | |
| C07D 417/12 | (2006.01) | |
| C07D 417/14 | (2006.01) | |

(52) U.S. Cl.
CPC .............. *A01N 43/78* (2013.01); *C07D 417/12* (2013.01); *C07D 417/14* (2013.01)

(58) Field of Classification Search
USPC .................... 514/152, 326; 552/205; 546/207
See application file for complete search history.

(56) References Cited

U.S. PATENT DOCUMENTS

| | | | |
|---|---|---|---|
| 4,245,432 A | 1/1981 | Dannelly | |
| 4,272,417 A | 6/1981 | Barke et al. | |
| 4,808,430 A | 2/1989 | Kouno | |
| 5,876,739 A | 3/1999 | Turnblad et al. | |
| 8,722,678 B2 * | 5/2014 | Hanagan et al. | 514/252.05 |
| 8,822,693 B2 * | 9/2014 | Hoffmann et al. | 546/211 |
| 2003/0176428 A1 | 9/2003 | Schneidersmann et al. | |
| 2010/0056569 A1 | 3/2010 | Nan et al. | |
| 2010/0137245 A1 | 6/2010 | Cristau et al. | |
| 2010/0190828 A1 | 7/2010 | Cristau et al. | |
| 2011/0046178 A1 | 2/2011 | Cristau et al. | |
| 2011/0105429 A1 | 5/2011 | Cristau et al. | |
| 2012/0122928 A1 | 5/2012 | Tsuchiya et al. | |
| 2012/0245204 A1 | 9/2012 | Hoffmann et al. | |

FOREIGN PATENT DOCUMENTS

| | | |
|---|---|---|
| WO | WO 89/10396 A1 | 11/1989 |
| WO | WO 96/33270 A1 | 10/1996 |
| WO | WO 02/28186 A2 | 4/2002 |
| WO | WO 02/080675 A1 | 10/2002 |
| WO | WO2004058751 * | 7/2004 |
| WO | WO 2006/018188 A2 | 2/2006 |
| WO | WO 2006/066109 A2 | 6/2006 |
| WO | WO 2006/133216 A2 | 12/2006 |
| WO | WO 2007/014290 A2 | 2/2007 |
| WO | WO 2007/024782 A2 | 3/2007 |
| WO | WO 2007/027777 A2 | 3/2007 |
| WO | WO 2007/039177 A2 | 4/2007 |
| WO | WO 2007/070818 A1 | 6/2007 |
| WO | WO 2008/004100 A2 | 1/2008 |
| WO | WO 2008/006794 A1 | 1/2008 |
| WO | WO 2008/013622 A2 | 1/2008 |
| WO | WO 2008/013925 A2 | 1/2008 |
| WO | WO 2008/064474 A1 | 6/2008 |
| WO | WO 2008/091580 A2 | 7/2008 |

(Continued)

OTHER PUBLICATIONS

Barany, G., et al., "A General Strategy for Elaboration of the Dithiocarbonyl Functionality,-(C═O)SS-: Application to the Synthesis of Bis(chlorocarbonyl)disulfane and Related Derivatives of Thiocarbonic Acids," *J. Org. Chem.* 48(24):4750-4761, American Chemical Society, United States (1983).

Brown, D.G., et al., "A Convenient Synthesis of Dimethyl (Diazomethyl)phosphonate (Seyferth/Gilbert Reagent)," *J. Org. Chem.* 61:2540-2541, American Chemical Society, United States (1996).

Chen, W., et al., "The Design and Synthesis of Bis(thiourea) Ligands and Their Application in Pd-Catalyzed Heck and Suzuki Reactions Under Aerobic Conditions," *Eur. J. Org. Chem.* 2006(5): 1177-1184, Wiley-VCH Verlag GmbH & Co. KGaA, Weinheim, Germany (2006).

(Continued)

*Primary Examiner* — Sabiha N Qazi
(74) *Attorney, Agent, or Firm* — Sterne, Kessler, goldstein & Fox P.L.L.C.

(57) ABSTRACT

Ketoheteroarylpiperidine and -piperazine derivatives of the formula (I),

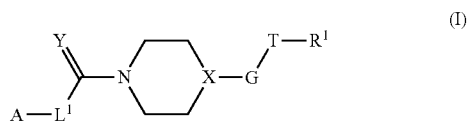

in which the symbols A, $L^1$, G, X, Y, T and $R^1$ have the meanings given in the description and agrochemically active salts thereof and their use for controlling phytopathogenic harmful fungi and also processes for preparing compounds of the formula (I).

20 Claims, No Drawings

(56) References Cited

FOREIGN PATENT DOCUMENTS

| WO | WO 2008/091594 A2 | 7/2008 |
| WO | WO 2009/055514 A2 | 4/2009 |
| WO | WO 2009/094407 A2 | 7/2009 |
| WO | WO 2009/094445 A2 | 7/2009 |
| WO | WO 2009/132785 A1 | 11/2009 |
| WO | WO 2010/065579 A2 | 6/2010 |
| WO | WO 2011/018401 A1 | 2/2011 |
| WO | WO 2011/018415 A2 | 2/2011 |

OTHER PUBLICATIONS

Dess, D.B. and Martin, J.C., "A Useful 12-I-5 Triacetoxyperiodinane (the Dess-Martin Periodinane) for the Selective Oxidation of Primary or Secondary Alcohols and a Variety of Related 12-I-5 Species," *J. Am. Chem. Soc.* 113:7277-7287, American Chemical Society, United States (1991).

Draber W., "Chemie der Pflanzenschutz-und Schadlingsbekampfungsmittel [Chemistry of Plant Protection and Pest Control Agents], " R. Wegler (eds.) 2:401-412, Springer-Verlag, Berlin (1970).

English language translation of Draber W., "Chemie der Pflanzenschutz-und Schadlingsbekampfungsmittel [Chemistry of Plant Protection and Pest Control Agents], " R. Wegler (eds.) 2:401-412, Springer-Verlag, Berlin (1970).

Grzyb, J.A. and Batey, R.A., "Achieving functional group diversity in parallel synthesis: solution-phase synthesis of a library of ureas, carmamates, thiocarbamates, and amides using carbamoylimidazolium salts," *Tetrahedron Letters* 49:5279-5282, Elsevier Ltd., United States (2008).

Grzyb, J.A., et al., "Carbamoylimidazolium and thiocarbamoylimidazolium salts: novel reagents for the synthesis of ureas, thioureas, carbamates, thiocarbamates and amides," *Tetrahedron* 61:7153-7175, Elsevier Ltd., United States (2005).

Hagen, S.E., et al., "4-Hydroxy-5,6-dihydropyrones as Inhibitors of HIV Protease: The Effect of Heterocyclic Substituents at C-6 on Antiviral Potency and Pharmacokinetic Parameters," *J. Med. Chem.* 44(14):2319-2332, American Chemical Society, United States (2001).

Jensen, O.E. and Senning, A., "Studies on Amino Acids and Peptides XII[1] Synthesis of Thiated Analogues of Boc-S-Ala-Aib-S-Ala-OMe and Ac-S-Ala-Aib-S-Ala-Ome," *Tetrahedron* 42(23):6555-6564, Pergamon Journals Ltd., Great Britain (1986).

Karikomi, M., et al.,"Regio- and stereocontrolled synthesis of novel 3-sulfonamido-2,3,4,5-tetrahydro-1,5-benzothiazepines from 2-(bromomethyl)- or 2-(sulfonyloxymethyl)aziridines," *Org. Biomol. Chem.* 6(11):1902-1904, The Royal Society of Chemistry, England (2008).

Karpov, A.S. and Müller, T.J.J., "Straightforward Novel One-Pot Enaminone and Pyrimidine Syntheses by Coupling-Addition-Cyclocondensation Sequences," *Synthesis* 18:2815-2826, Georg Thieme Verlag Stuttgart, New York, United States (2003).

Lu, Y., et al., "Discovery of 4-Substituted Methoxybenzoyl-aryl-thiazole as Novel Anticancer Agents: Synthesis, Biological Evaluation, and Structure-Activity Relationships," *J. Med. Chem.* 52(6):1701-1711, American Chemical Society, United States (2009).

Matsubara, N., et al., "Molecular Design of Glycoprotein Mimetics: Glycoblotting by Engineered Proteins with an Oxylamino-Functionalized Amino Acid Residue," *Chem. Eur. J.* 11(23):6974-6981, Wiley-VCH Verlag GmbH & Co. KGaA, Weinheim, Germany (2005).

Metzger, A., et al., "LiCl-Mediated Preparation of Highly Functionalized Benzylic Zinc Chlorides," *Organic Letters* 10(6):1107-1110, American Chemical Society, United States(2008).

Montalbetti, C.A.G.N and Falque, V.,"Amide bond formation and peptide coupling," *Tetrahedron* 61:10827-10852, Elsevier Ltd., United States (2005).

Pal, R.R., et al., "Optically Active Metallo-Supramolecular Polymers Derived from Chiral Bis-terpyridines," *Organic Letters* 11(16):3562-3565, American Chemical Society, United States (2009).

Ragnarsson, U., "Synthetic methodology for alkyl substituted hydrazines," *Chem. Soc. Rev.* 30:205-213, The Royal Society of Chemistry, England (2001).

Rateb, N.M. and Zohdi, H.F., "Atom-Efficient, Solvent-Free, Green Synthesis of Chalcones by Grinding," *Synthetic Communications®* 39:2789-2794, Taylor & Francis Group, LLC, England (2009).

Rodik, R., et al., "Calix[4]arenesulfonylamidines. Synthesis, structure and influence on $Mg^{2+}$, ATP-dependent calcium pumps," *Tetrahedron Letters* 46:7549-7462, Elsevier Ltd., United States (2005).

Roth, G.J., et al.,"Further Improvements of the Synthesis of Alkynes from Aldehydes," *Synthesis* (1):59-62, Georg Thieme Verlag Stuttgart, New YOrk, United States (2004).

Rouden, J., et al., "Studies toward Labeling Cytisine with [$^{11}$C]Phosgene: Rapid Synthesis of a δ-Lactam Involving a New Chemoselective Lithiation-Annulation Method," *J. Org. Chem.* 69(11):3787-3793, American Chemical Society, United States (2004).

Schweifer, A. and Hammerschmidt, F., "Formal and improved synthesis of enantiopure chiral methanol," *Tetrahedron* 64:7605-7610, Elsevier Ltd., United States (2008).

Simiti, I., et al., "Darstellung and Charakterisierung einiger 1,Diaryl-5-[(2-aryl-5X)-thiazol-4-yl] pyrazole," *Pharmazie* 43:82-84, Govi-Verlag, Germany (1988).

International Search Report International Application No. PCT/EP2011/056594, European Patent Office, The Hague, Netherlands, mailed on Jun. 8, 2011.

\* cited by examiner

KETOHETEROARYLPIPERIDINE AND -PIPERAZINE DERIVATIVES AS FUNGICIDES

The present invention relates to novel ketoheteroarylpiperidine and -piperazine derivatives, to processes for their preparation, to their use for controlling unwanted microorganisms, in particular phytopathogenic fungi, in crop protection, in the domestic and hygiene field and in the protection of materials, and also to crop protection compositions comprising these ketoheteroarylpiperidine and -piperazine derivatives.

It is already known that certain heteroarylpiperidine and -piperazine derivatives can be used as fungicidal crop protection agents (see WO 2007/014290, WO 2008/013925, WO 2008/013622, WO 2008/091594, WO 2008/091580, WO 2009/055514, WO 2009/094407, WO 2009/094445, WO 2009/132785, WO 2010/037479, WO 2010/065579, WO 2010/149275, WO 2010/066353, WO 2011/018401, WO 2011/018415). However, in particular at relatively low application rates, the fungicidal activity of these compounds is not always sufficient.

Since the ecological and economical demands made on modern crop protection agents are increasing constantly, for example with respect to activity spectrum, toxicity, selectivity, application rate, formation of residues and favourable manufacture, and there can furthermore be problems, for example, with resistances, there is a constant need to develop novel crop protection agents, in particular fungicides, which, at least in some areas, have advantages over the known ones.

Surprisingly, it has now been found that the present ketoheteroarylpiperidine and -piperazine derivatives achieve at least some aspects of the objects mentioned and are suitable for use as crop protection agents, in particular as fungicides.

The invention relates to compounds of the formula (I)

(I)

in which the symbols have the following meanings:

A represents phenyl which may contain up to three substituents,
where the substituents independently of one another are selected from $R^2$,
or
A' represents optionally benzo-fused unsubstituted or substituted 5- or 6-membered heteroaryl, where the substituents at carbon are independently of one another selected from $R^3$ and the substituents at nitrogen are independently of one another selected from $R^4$,
$L^1$ represents $NR^5$ or $C(R^6)_2$,
X represents CH or nitrogen,
Y represents sulphur or oxygen,
G represents:

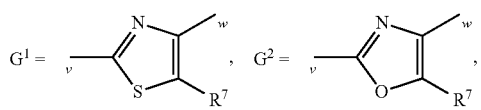

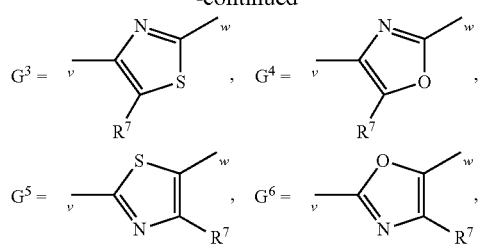

where the bond identified by "v" is attached directly to X and where the bond identified by "w" is attached directly to T, T represents *—C(=O)CH$_2$—#, *—C(=O)CH$_2$C(R$^8$)$_2$—#, *—C(=O)CH=CH—#, *—C(=O)C≡C—#, *—C(=O)CH$_2$C(=O)—#, *—C≡CC(=O)—#, *—CH=CHC(=O)—#, *—CH$_2$CH$_2$C(=O)—#, *—C(=S)CH$_2$—#, *—C(=S)CH$_2$C(R$^8$)$_2$—#, *—C(=S)CH=CH—#, *—C(=S)C≡C—#, *—C≡CC(=S)—#, *—CH=CHC(=S)—#, *—CH$_2$CH$_2$C(=S)—#, *—C(=NR$^9$)CH$_2$—#, *—C(=NR$^9$)CH$_2$C(R$^8$)$_2$—#, *—CH$_2$CH$_2$C(=NR$^9$)—#, *—C(=NR$^9$)CH=CH—#, *—CH=CHC(=NR$^9$)—#, *—CH—CHC(NOH)—# or *—CH=CHC(NO—C$_1$-C$_4$-alkyl)CH$_2$—#, where the bond identified by * is attached directly to G and where the bond identified by # is attached directly to $R^1$, $R^1$ is selected from the group containing $R^1_a$, $R^1_b$, $R^1_c$, $R^1_d$, $R^1_e$, $R^1_f$, $R^1_g$, or $R^1_h$, where $R^1_a$ represents $C_1$-$C_6$-alkyl, $C_1$-$C_6$-haloalkyl, $C_2$-$C_6$-alkenyl, $C_2$-$C_6$-alkynyl, $C_2$-$C_8$-alkoxyalkyl or $C_5$-$C_9$-cycloalkoxyalkyl, or $R^1_b$ represents unsubstituted or substituted $C_3$-$C_{10}$-cycloalkyl
where the substituents independently of one another are selected from -Q or $R^{10}$ or $R^1_c$ represents unsubstituted or substituted $C_5$-$C_{10}$-cycloalkenyl,
where the substituents independently of one another are selected from $R^{11}$ or $R^1_d$ represents unsubstituted or substituted phenyl,
where the substituents independently of one another are selected from -L$^2$Q or $R^{12}$ or $R^1_e$ represents unsubstituted or substituted naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl,
where the substituents independently of one another are selected from $R^{13}$ or $R^1_f$ represents an unsubstituted or substituted 5- or 6-membered heteroaryl radical, where the substituents at carbon independently of one another are selected from -L$^2$Q or $R^{14}$ and the substituents at nitrogen independently of one another are selected from -L$^3$Q or $R^{15}$ or $R^1_g$ represents benzo-fused unsubstituted or substituted 5- or 6-membered heteroaryl, where the substituents at carbon independently of one another are selected from $R^{16}$ and the substituents at nitrogen independently of one another are selected from $R^{17}$ or $R^1_h$ represents unsubstituted or substituted $C_5$-$C_{15}$-heterocyclyl, where the substituents at carbon independently of one another are selected from $R^{18}$ and the substituents at nitrogen independently of one another are selected from $R^{19}$, $L^2$ represents a direct bond, —O—, —C($R^{20}$)$_2$— or —N$R^{21}$—, $L^3$ represents a direct bond or —C($R^{20}$)$_2$—, Q is selected from the group containing Q', Q" and Q'", where Q' represents phenyl which may contain up to two substituents, where the substituents independently of one another are selected from $R^{22}$ or Q" represents a 5- or 6-membered heteroaryl radical which may contain up to two substituents, where the substituents at carbon independently of one another are selected from $R^{23}$ and the substituents at nitrogen independently of one another are selected from $R^{24}$ or Q'" represents saturated or partially unsaturated $C_3$-$C_{10}$-cycloalkyl, $R^2$, $R^{12}$ and $R^{22}$ independently of one another represent halogen, cyano, hydroxyl, SH, amino, nitro, phenyl, C(=O)H, C(=O)OH, CON$R^{25}R^{26}$, N$R^{25}R^{26}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_4$-$C_{10}$-halocycloalkylalkyl, $C_5$-$C_{10}$-alkylcycloalkylalkyl, $C_3$-$C_8$-cycloalkenyl, $C_3$-$C_8$-halocycloalkenyl, $C_2$-$C_6$-alkoxyalkyl, $C_4$-$C_{10}$-cycloalkoxyalkyl, $C_3$-$C_8$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_8$-dialkylaminoalkyl, $C_2$-$C_6$-haloalkylamino alkyl, $C_4$-$C_{10}$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_5$-$C_{10}$-cycloalkylalkoxycarbonyl, $C_2$-$C_6$-alkylaminocarbonyl, $C_3$-$C_8$-dialkylaminocarbonyl, $C_4$-$C_8$-cycloalkylaminocarbonyl, $C_2$-$C_6$-haloalkoxyalkyl, $C_1$-$C_6$-hydroxyalkyl, $C_1$-$C_6$-alkoxy, $C_1$-$C_6$-haloalkoxy, $C_3$-$C_8$-cycloalkoxy, $C_3$-$C_8$-halocycloalkoxy, $C_4$-$C_{10}$-cycloalkylalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_2$-$C_6$-alkoxyalkoxy, $C_2$-$C_6$-alkylcarbonyloxy, $C_2$-$C_6$-haloalkylcarbonyloxy, $C_4$-$C_8$-cycloalkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, $C_1$-$C_6$-alkylsulphonylamino or $C_1$-$C_6$-haloalkylsulphonylamino, $R^3$, $R^{14}$, $R^{16}$, $R^{18}$ and $R^{23}$ independently of one another represent halogen, cyano, hydroxyl, SH, amino, nitro, N$R^{25}R^{26}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_3$-$C_6$-alkenyloxy, $C_3$-$C_6$-alkynyloxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl, $R^4$, $R^{15}$, $R^{17}$, $R^{19}$ and $R^{24}$ independently of one another represent $C_1$-$C_6$-alkyl, $C_2$-$C_6$-alkenyl, $C_2$-$C_6$-alkynyl, $C_1$-$C_6$-haloalkyl, $C_3$-$C_6$-haloalkenyl, $C_3$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, phenyl, benzyl, $C_1$-$C_4$-alkylsulphonyl, C(=O)H, $C_2$-$C_4$-alkylcarbonyloxy, $C_2$-$C_5$-alkoxycarbonyl or $C_2$-$C_5$-alkylcarbonyl, $R^5$ represents hydrogen or $C_1$-$C_4$-alkyl, $R^6$ independently of one another represent hydrogen, $C_1$-$C_4$-alkyl, $C_1$-$C_4$-haloalkyl, cyclopropyl, halogen, or the two radicals $R^6$ together with the carbon atom to which they are attached form a cyclopropyl ring, $R^7$ represents hydrogen, $C_1$-$C_3$-alkyl, $C_1$-$C_3$-haloalkyl, $C_1$-$C_4$-alkoxy, $C_2$-$C_5$-alkoxycarbonyl or halogen, $R^8$ independently of one another represent hydrogen or $C_1$-$C_4$-alkyl, $R^9$ represents OH, nitro, cyano, $C_1$-$C_4$-alkyl, $C_1$-$C_4$-alkylamino, $C_2$-$C_4$-dialkylamino, $C_1$-$C_4$-alkoxy, $C_1$-$C_4$-haloalkoxy or cyclopropyloxy $R^{10}$ and $R^{11}$ independently of one another represent cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, phenyl, hydroxyl, oxo, $C_1$-$C_6$-alkoxy, $C_1$-$C_6$-haloalkoxy, $C_3$-$C_6$-alkenyloxy, $C_3$-$C_6$-alkynyloxy, $C_1$-$C_6$-alkylthio or $C_1$-$C_6$-haloalkylthio, $R^{13}$ independently of one another represent cyano, nitro, halogen, $C_1$-$C_6$-alkyl, $C_1$-$C_4$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, benzyl, phenyl, hydroxyl, SH, $C_1$-$C_6$-alkoxy, $C_1$-$C_6$-haloalkoxy, $C_3$-$C_6$-alkenyloxy, $C_3$-$C_6$-alkynyloxy, $C_1$-$C_6$-alkylthio or $C_1$-$C_6$-haloalkylthio, $R^{20}$ independently of one another represent hydrogen, halogen, $C_1$-$C_4$-alkyl or $C_1$-$C_4$-haloalkyl, $R^{21}$ represents $C_1$-$C_6$-alkyl, $C_1$-$C_6$-haloalkyl, $C_3$-$C_8$-cycloalkyl, $C_2$-$C_6$-alkylcarbonyl, $C_2$-$C_6$-haloalkylcarbonyl, $C_2$-$C_6$-alkoxycarbonyl or $C_2$-$C_6$-haloalkoxycarbonyl, $R^{25}$ and $R^{26}$ independently of one another represent hydrogen, $C_1$-$C_4$-alkyl, $C_2$-$C_6$-alkenyl, $C_2$-$C_6$-alkynyl, $C_1$-$C_3$-haloalkyl, $C_3$-$C_6$-cycloalkyl, benzyl or phenyl, and also agrochemically active salts thereof.

The invention furthermore provides the use of the compounds of the formula (I) as fungicide.

The ketoheteroarylpiperidine and -piperazine derivatives of the formula (I) according to the invention and their agrochemically active salts are highly suitable for controlling phytopathogenic harmful fungi. The compounds according to the invention mentioned above in particular have potent fungicidal activity and can be used both in crop protection, in the domestic and hygiene field and in the protection of materials.

The compounds of the formula (I) can be present both in pure form and as mixtures of various possible isomeric forms, in particular of stereoisomers, such as E and Z, threo and erythro, and also optical isomers, such as R and S isomers or atropisomers, and, if appropriate, also of tautomers. What is claimed are both the E and the Z isomers, and also the threo and erythro, and also the optical isomers, any mixtures of these isomers, and also the possible tautomeric forms.

A preferably represents phenyl which may contain up to two substituents, where the substituents independently of one another are selected from $R^2$ list and $R^2$ preferably represents:
halogen, cyano, hydroxyl, amino, nitro, $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_2$-$C_4$-alkoxyalkyl, $C_2$-$C_5$-alkylcarbonyl, $C_2$-$C_6$-alkoxycarbonyl, $C_2$-$C_6$-alkylcarbonyloxy or C(=O)H, A' furthermore preferably represents a heteroaromatic radical selected from the group below: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrazin-2-yl, pyrazin-3-yl, pyrimidin-2-yl, pyrimidin-4-yl or pyrimidin-5-yl which may contain up to two substituents, where the substituents independently of one another are selected from $R^3$ and $R^4$ and $R^3$ preferably represents a substituent at carbon:
halogen, cyano, hydroxyl, amino, nitro, $C_1$-$C_6$-alkyl, $C_2$-$C_6$-alkenyl, $C_2$-$C_6$-alkynyl, $C_3$-$C_8$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_2$-$C_4$-alkoxyalkyl, $C_2$-$C_6$-alkoxycarbonyl, $C_2$-$C_6$-alkylcarbonyloxy, $C(=O)H$ or phenyl $R^4$ preferably represents a substituent at nitrogen:
$C_1$-$C_6$-alkyl, $C_1$-$C_4$-haloalkyl, $C_3$-$C_6$-alkenyl, $C_3$-$C_6$-haloalkenyl, $C_3$-$C_6$-alkynyl or $C_3$-$C_6$-haloalkynyl.

A particularly preferably represents phenyl which may contain up to two substituents, where the substituents independently of one another are selected from $R^2$ and $R^2$ particularly preferably represents:
fluorine, bromine, iodine, chlorine, cyano, nitro, methyl, ethyl, propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, propoxy, methoxy, trifluoromethoxy, difluoromethoxy, 1-methylethylthio, methylthio, ethylthio, propylthio, difluoromethylthio or trifluoromethylthio, A' particularly preferably represents a heteroaromatic radical selected from the group below: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl or pyrimidin-5-yl which may contain up to two substituents, where the substituents independently of one another are selected from $R^3$ and $R^4$ and $R^3$ particularly preferably represents a substituent at carbon:
fluorine, chlorine, bromine, iodine, cyano, nitro, methyl, ethyl, propyl, 1-methylethyl, 1,1-dimethylethyl, chlorofluoromethyl, dichloromethyl, dichlorofluoromethyl, difluoromethyl, trichloromethyl, trifluoromethyl, cyclopropyl, ethoxy, 1-methylethoxy, propoxy, methoxy, trifluoromethoxy, difluoromethoxy, 1-methylethylthio, methylthio, ethylthio, propylthio, difluoromethylthio, trifluoromethylthio or phenyl, $R^4$ particularly preferably represents a substituent at nitrogen:
methyl, ethyl, propyl, 1-methylethyl, 2,2-trifluoroethyl, 2,2-difluoroethyl, 2,2-dichloro-2-fluoroethyl, 2-chloro-2-difluoroethyl or 2-chloro-2-fluoroethyl, A' very particularly preferably represents pyrazol-1-yl which may contain up to two substituents, where the substituents independently of one another are selected from $R^3$ and $R^3$ very particularly preferably represents
methyl, difluoromethyl or trifluoromethyl, A furthermore very particularly preferably represents phenyl which may contain up to two substituents, where the substituents independently of one another are selected from $R^2$ and $R^2$ very particularly preferably represents:
methyl, ethyl, iodine, chlorine, bromine, fluorine, methoxy, ethoxy, difluoromethyl or trifluoromethyl, G preferably represents $G^1$ or $G^2$, G particularly preferably represents $G^1$, T preferably represents *—C(=O)CH$_2$—#, *—C(=O)CH$_2$C(R$^8$)$_2$—#, *—C(=O)CH=CH—#, *—C(=O)C≡C—#, *—C≡CC(=O)—#, *—CH=CHC(=O)—#, *—CH$_2$CH$_2$C(=O)—#, *—C(=S)CH$_2$—#, *—C(=S)CH$_2$C(R$^8$)$_2$—#, *—CH$_2$CH$_2$C(=S)—#, *—C(=NR$^9$)CH$_2$—#, *—C(=NR$^9$)CH=CH—#, *—CH=CHC(=NR$^9$)—#, *—CH=CHC(NOH)—#, or *—CH=CHC(NO—C$_1$-C$_4$-alkyl)CH$_2$—#, T particularly preferably represents *—C(=O)CH$_2$—#, *—C(=O)CH$_2$C(R$^8$)$_2$—#, *—C(=O)CH=CH—#, *—C≡CC(=O)—#, *—CH=CHC(=O)—#, *—CH$_2$CH$_2$C(=O)—#, *—C(=S)CH$_2$—#, *—C(=S)CH$_2$C(R$^8$)$_2$—#, *—CH$_2$CH$_2$C(=S)—#, *—C(=NR$^9$)CH$_2$—#, *—C(=NR$^9$)CH=CH—#, *—CH=CHC(=NOH)—# or *—CH=CHC(N—O—C$_1$-C$_4$-alkyl)CH$_2$—#, T very particularly preferably represents *—C(=O)CH$_2$—#, *—C(=O)CH$_2$C(CH$_3$)$_2$—#, *—C(=O)CH$_2$CH$_2$—#, *—C(=O)CH=CH—#, *—C≡CC(=O)—#, *—CH=CHC(=O)—# or *—CH$_2$CH$_2$C(=O)—#, *—C(=NOCH$_3$)CH$_2$—#, *—C(=N—OH)CH=CH—#, *—C(=N—OCH$_3$)CH=CH—#, or *—CH=CHC(NOH)—#, $L^1$ preferably represents CH$_2$ or NR$^5$, particularly preferably CH$_2$, X preferably represents CH, Y preferably represents oxygen, $R^1_a$ preferably represents $C_1$-$C_6$-alkyl, $C_1$-$C_6$-haloalkyl, $C_2$-$C_6$-alkenyl or $C_2$-$C_6$-alkynyl, $C_2$-$C_6$-alkoxyalkyl, $R^1_b$ preferably represents unsubstituted or substituted $C_3$-$C_{10}$-cycloalkyl, where the substituents independently of one another are selected from -Q or $R^{10}$ and $R^{10}$ preferably represents:
cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, hydroxyl, oxo, $C_1$-$C_6$-alkoxy, $C_1$-$C_6$-haloalkoxy, $C_3$-$C_6$-alkenyloxy, $C_3$-$C_6$-alkynyloxy, $C_1$-$C_6$-alkylthio, $C_1$-$C_6$-haloalkylthio, $R^1_c$ preferably represents unsubstituted or substituted $C_5$-$C_{10}$-cycloalkenyl, where the substituents independently of one another are selected from $R^{11}$ and $R^{11}$ preferably represents:
cyano, chlorine, fluorine, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, phenyl, oxo, $C_1$-$C_6$-alkoxy, $C_1$-$C_6$-haloalkoxy, $C_3$-$C_6$-alkenyloxy, $C_3$-$C_6$-alkynyloxy, $C_1$-$C_6$-alkylthio or $C_1$-$C_6$-haloalkylthio, $R^1_d$ preferably represents unsubstituted or substituted phenyl, where the substituents independently of one another are selected from -$L^2$Q or $R^{12}$ and $R^{12}$ preferably represents:

represents halogen, cyano, hydroxyl, SH, amino, nitro, C(=O)H, C(=O)OH, $CONR^{25}R^{26}$, $NR^{25}R^{26}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_4$-$C_{10}$-halocycloalkylalkyl, $C_5$-$C_{10}$-alkylcycloalkylalkyl, $C_3$-$C_8$-cycloalkenyl, $C_3$-$C_8$-halocycloalkenyl, $C_2$-$C_6$-alkoxyalkyl, $C_4$-$C_{10}$-cycloalkoxyalkyl, $C_3$-$C_8$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_8$-dialkylaminoalkyl, $C_2$-$C_6$-haloalkylaminoalkyl, $C_4$-$C_{10}$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_5$-$C_{10}$-cycloalkylalkoxycarbonyl, $C_2$-$C_6$-alkylaminocarbonyl, $C_3$-$C_8$-dialkylaminocarbonyl, $C_4$-$C_8$-cycloalkylaminocarbonyl, $C_2$-$C_6$-haloalkoxyalkyl, $C_1$-$C_6$-hydroxyalkyl, $C_1$-$C_6$-alkoxy, $C_1$-$C_6$-haloalkoxy, $C_3$-$C_8$-cycloalkoxy, $C_3$-$C_8$-halocycloalkoxy, $C_4$-$C_{10}$-cycloalkylalkoxy, $C_3$-$C_6$-alkenyloxy, $C_3$-$C_6$-haloalkenyloxy, $C_3$-$C_6$-alkynyloxy, $C_3$-$C_6$-haloalkynyloxy, $C_2$-$C_6$-alkoxyalkoxy, $C_2$-$C_6$-alkylcarbonyloxy, $C_2$-$C_6$-haloalkylcarbonyloxy, $C_4$-$C_7$-cycloalkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, $C_1$-$C_6$-alkylsulphonylamino, $C_1$-$C_6$-haloalkylsulphonylamino, $R^1_e$ preferably represents unsubstituted or substituted naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, where the substituents independently of one another are selected from $R^{13}$ and $R^{13}$ preferably represents:
cyano, halogen, $C_1$-$C_6$-alkyl, $C_1$-$C_4$-haloalkyl, $C_2$-$C_6$-alkenyl, $C_2$-$C_6$-alkynyl, benzyl, phenyl, $C_1$-$C_6$-alkoxy, $C_1$-$C_6$-haloalkoxy, $C_3$-$C_6$-alkenyloxy, $C_3$-$C_6$-alkynyloxy or $C_1$-$C_6$-alkylthio, $R^1_f$ preferably represents an unsubstituted or substituted 5- or 6-membered heteroaryl radical, where the substituents independently of one another are selected from -$L^2$Q or $R^{14}$ and -$L^3$Q or $R^{15}$ and $R^{14}$ preferably represents a substituent at carbon:
halogen, cyano, hydroxyl, SH, amino, nitro, $NR^{25}R^{26}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_3$-$C_6$-alkenyloxy, $C_3$-$C_6$-alkynyloxy, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl, $R^{15}$ preferably represents a substituent at nitrogen:
$C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, phenyl, $R^1_g$ preferably represents a benzo-fused unsubstituted or substituted 5- or 6-membered heteroaryl, where the substituents independently of one another are selected from $R^{16}$ and $R^{17}$ and $R^{16}$ preferably represents a substituent at carbon:
halogen, cyano, hydroxyl, SH, amino, nitro, $NR^{25}R^{26}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl, $R^{17}$ preferably represents a substituent at nitrogen:
$C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl or phenyl, $R^1_h$ preferably represents unsubstituted or substituted $C_5$-$C_{15}$-heterocyclyl, where possible substituents independently of one another are selected from $R^{18}$ and $R^{19}$ and $R^{18}$ preferably represents a substituent at carbon:
halogen, cyano, hydroxyl, SH, amino, nitro, $NR^{25}R^{26}$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl, $R^{19}$ preferably represents a substituent at nitrogen:
$C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl or phenyl, $R^1_a$ particularly preferably represents 1,1-dimethylethyl, 3,3-dimethylbutyl, 2,2-dimethylpropyl, 1,2,2-trimethylpropyl, pentyl, 1-ethylpropyl, butyl, 2-methylpropyl, 1-methylethyl, ethyl, propyl, 4-methylpentyl or hexyl, $R^1_b$ particularly preferably represents cyclopentyl, cyclohexyl or cycloheptyl, each of which may contain up to two substituents, where the substituents independently of one another are selected from $R^{10}$ and $R^{10}$ particularly preferably represents:
cyano, chlorine, fluorine, bromine, iodine, methyl, ethyl, propyl, 1-methylethyl, 1,1-dimethylethyl, ethenyl, phenyl, methoxy, ethoxy, propyloxy, trifluoromethoxy, ethynyl, 2-propynyloxy, methylthio, ethylthio or trifluoromethylthio, $R^1_c$ particularly preferably represents cyclopentenyl, cyclohexenyl or cycloheptenyl, each of which may contain up to two substituents, where the substituents independently of one another are selected from $R^{11}$ and $R^{11}$ particularly preferably represents:
methyl, ethyl, methoxy, ethoxy, trifluoromethoxy, ethynyl, 2-propynyloxy, methylthio, ethylthio or trifluoromethylthio, $R^1_d$ particularly preferably represents phenyl which may contain up to three substituents, where the substituents independently of one another are selected from -L²Q' or $R^{12}$ and $R^{12}$ particularly preferably represents:
fluorine, chlorine, bromine, iodine, cyano, nitro, methyl, ethyl, propyl, 1-methylethyl, butyl, 1,1-dimethylethyl, 1,2-dimethylethyl, ethenyl, ethynyl, trifluoromethyl, difluoromethyl, trichloromethyl, dichloromethyl, cyclopropyl, methoxy, ethoxy, propoxy, 1-methylethoxy, 1,1-dimethylethoxy, methylcarbonyl, ethylcarbonyl, trifluoromethylcarbonyl, methoxycarbonyl, ethoxycarbonyl, propoxycarbonyl, 1-methylethoxycarbonyl, 1,1-dimethylethoxycarbonyl, 2-propenyloxy, 2-propynyloxy, methylthio, ethylthio, methylsulphinyl or methylsulphonyl, $R^1_e$ particularly preferably represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl which may contain up to three substituents, where the substituents independently of one another are selected from $R^{13}$ and $R^{13}$ particularly preferably represents:
methyl, methoxy, cyano, fluorine, chlorine, bromine, iodine, $R^1_f$ particularly preferably represents furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl or pyrazin-2-yl, which may each contain up to two substituents, where the substituents independently of one another are selected from $R^{14}$ and $R^{15}$ and $R^{14}$ particularly preferably represents a substituent at carbon:
chlorine, fluorine, bromine, iodine, cyano, nitro, methyl, ethyl, propyl, 1-methylethyl, butyl, 1,1-dimethylethyl, ethenyl, ethynyl, trifluoromethyl, difluoromethyl, cyclopropyl, cyclopentyl, cyclohexyl, methylcarbonyl, ethylcarbonyl, methoxycarbonyl, ethoxycarbonyl, methoxy, ethoxy, propoxy, 1-methylethoxy, 2-propynyloxy, trifluoromethoxy, methylcarbonyloxy, methylcarbonylthio, methylthio, ethylthio, trifluoromethylthio, methylsulphinyl, ethylsulphinyl, trifluoromethylsulphinyl, methylsulphonyl, ethylsulphonyl or trifluoromethylsulphonyl, $R^{15}$ particularly preferably represents a substituent at nitrogen:
methyl, ethyl, propyl, cyclopropyl, cyclohexyl, phenyl or 2-propynyl, $R^1_g$ particularly preferably represents indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, each of which may contain up to two substituents, where the substituents independently of one another are selected from $R^{16}$ and $R^{17}$ and $R^{16}$ particularly preferably represents a substituent at carbon:
fluorine, chlorine, bromine, iodine, methyl, methoxy, 2-propynyloxy, 2-propenyloxy, $R^{17}$ particularly preferably represents a substituent at nitrogen:
methyl, ethyl, propyl, cyclopropyl, cyclohexyl, phenyl or 2-propynyl, $R^1_a$ very particularly preferably represents 1,1-dimethylethyl, $R^1_b$ very particularly preferably represents cyclohexyl, cyclopentyl, 2-methylcyclohexyl, 3-methylcyclohexyl or 4-methylcyclohexyl, $R^1_c$ very particularly preferably represents cyclohex-3-en-1-yl or cyclohex-2-en-1-yl, $R^1_d$ very particularly preferably represents phenyl which may contain up to two substituents, where the substituents independently of one another are selected from $R^{12}$ and $R^{12}$ very particularly preferably represents:
chlorine, fluorine, bromine, iodine, methyl, methoxy, ethoxy, trifluoromethyl, difluoromethyl, 2-propenyloxy, 2-propynyloxy or phenyl, $R^1_e$ very particularly preferably represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, $R^1_f$ very particularly preferably represents furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl or pyrimidin-5-yl, $L^2$ preferably represents a direct bond or —O—, $L^2$ particularly preferably represents a direct bond, $L^3$ preferably represents a direct bond, Q' preferably represents phenyl which may contain up to two substituents, where the substituents independently of one another are selected from $R^{22}$ and $R^{22}$ preferably represents:
 fluorine, chlorine, bromine, iodine, cyano, hydroxyl, SH, nitro, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio or $C_1$-$C_4$-haloalkylthio, Q" preferably represents furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, tetrazol-5-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl or 1,2,4-triazin-3-yl which may contain up to two substituents, where the substituents independently of one another are selected from $R^{23}$ and $R^{24}$ and $R^{23}$ preferably represents a substituent at carbon:
 fluorine, chlorine, bromine, iodine, cyano, hydroxyl, SH, nitro, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio or $C_1$-$C_4$-haloalkylthio, $R^{24}$ preferably represents a substituent at nitrogen:
 $C_1$-$C_6$-alkyl, $C_3$-$C_6$-alkenyl, $C_3$-$C_6$-alkynyl, $C_3$-$C_6$-cycloalkyl or phenyl, Q' particularly preferably represents phenyl, $R^5$ preferably represents hydrogen or methyl, ethyl, propyl, isopropyl, butyl, isobutyl or tert-butyl, $R^5$ particularly preferably represents hydrogen, $R^7$ preferably represents hydrogen, $R^8$ independently of one another preferably represent hydrogen, methyl or ethyl, $R^8$ particularly preferably represents hydrogen, methyl, $R^{25}$ and $R^{26}$ independently of one another preferably represent hydrogen, methyl, ethyl, propyl, isopropyl, butyl, isobutyl or tert-butyl.

The formula (I) provides a general definition of the ketoheteroarylpiperidine and -piperazine derivatives which can be used according to the invention. Preferred radical definitions for the formulae shown above and below are given below. These definitions apply to the end products of the formula (I) and likewise to all intermediates (see also below under "Illustration of the processes and intermediates").

The radical definitions and explanations stated above in general or stated in preferred ranges can, however, also be combined as desired with one another, that is to say between the respective ranges and preferred ranges. They apply both to the end products and, correspondingly, to precursors and intermediates. Moreover, individual definitions may not apply.

Preference is given to those compounds of the formula (I) in which all radicals in each case have the preferred meanings mentioned above.

Particular preference is given to those compounds of the formula (I) in which all radicals in each case have the particularly preferred meanings mentioned above.

Very particular preference is given to those compounds of the formula (I) in which all radicals in each case have the very particularly preferred meanings mentioned above.

Preference is furthermore given to compounds of the formula (I) in which
A represents 3,5-bis(difluoromethyl)-1H-pyrazol-1-yl.

Preference is furthermore given to compounds of the formula (I) in which
A represents 5-methyl-3-(trifluoromethyl)-1H-pyrazol-1-yl.

Preference is furthermore given to compounds of the formula (I) in which
A represents 2,5-dimethylphenyl.

Preference is furthermore given to compounds of the formula (I) in which
A represents 2-methyl-5-chlorophenyl.

Preference is furthermore given to compounds of the formula (I) in which
G represents $G^1$.

Preference is furthermore given to compounds of the formula (I) in which
T represents *—C(=O)CH$_2$—#.

Preference is furthermore given to compounds of the formula (I) in which
T represents *—C(=O)CH$_2$C(CH$_3$)$_2$—#.

Preference is furthermore given to compounds of the formula (I) in which
T represents *—C(=O)CH$_2$CH$_2$—#.

Preference is furthermore given to compounds of the formula (I) in which
T represents *—C(=O)CH=CH—#.

Preference is furthermore given to compounds of the formula (I) in which
T represents *—C≡CC(=O)—#.

Preference is furthermore given to compounds of the formula (I) in which
T represents *—CH=CHC(=O)—#.

Preference is furthermore given to compounds of the formula (I) in which
T represents *—CH$_2$CH$_2$C(=O)—#.

Preference is furthermore given to compounds of the formula (I) in which
T represents *—C(=NOCH$_3$)CH$_2$—#.

Preference is furthermore given to compounds of the formula (I) in which
T represents *—CH=CHC(=NOH)—#.

Preference is furthermore given to compounds of the formula (I) in which
X represents CH.

Preference is furthermore given to compounds of the formula (I) in which
Y represents oxygen.

Preference is furthermore given to compounds of the formula (I) in which
$L^1$ represents NH.

Preference is furthermore given to compounds of the formula (I) in which
$L^1$ represents —CH$_2$—.

Preference is furthermore given to compounds of the formula (I) in which
$R^8$ represents hydrogen.

Preference is furthermore given to compounds of the formula (I) in which
$R^8$ represents methyl.

Preference is furthermore given to compounds of the formula (I) in which
$R^5$ represents hydrogen.

Preference is furthermore given to compounds of the formula (I) in which
R$^1$ represents cyclohexyl (R$^1_b$).

Preference is furthermore given to compounds of the formula (I) in which
R$^1$ represents phenyl (R$^1_d$).

Preference is furthermore given to compounds of the formula (I) in which
R$^1$ represents 2-methoxyphenyl (R$^1_d$).

Preference is furthermore given to compounds of the formula (I) in which
R$^1$ represents 4-methoxyphenyl (R$^1_d$).

Preference is furthermore given to compounds of the formula (I) in which
R$^1$ represents 2-ethoxyphenyl (R$^1_d$).

Preference is furthermore given to compounds of the formula (I) in which
R$^1$ represents naphthalen-1-yl (R$^1_e$).

Preference is furthermore given to compounds of the formula (I) in which
R$^1$ represents tert-butyl (R$^1_a$).

Preference is furthermore given to compounds of the formula (I) in which
R$^1$ represents thiophen-2-yl (R$^1_f$).

Preference is furthermore given to compounds of the formula (I) in which
R$^1$ represents furan-2-yl (R$^1_f$).

Preference is furthermore given to compounds of the formula (I) in which
R$^1$ represents 2-chlorophenyl (R$^1_d$).

Preference is furthermore given to compounds of the formula (I) in which
R$^1$ represents 2,4-dichlorophenyl (R$^1_d$).

Preference is furthermore given to compounds of the formula (I) in which
R$^1$ represents 2-bromophenyl (R$^1_d$).

Preference is furthermore given to compounds of the formula (I) in which
R$^1$ represents 2,6-difluorophenyl (R$^1_d$).

Preference is furthermore given to compounds of the formula (I) in which
R$^1$ represents 2-iodophenyl (R$^1_d$).

Preference is furthermore given to compounds of the formula (I) in which
R$^1$ represents 2-methylphenyl (R$^1_d$).

Preference is furthermore given to compounds of the formula (I) in which
R$^1$ represents 3-methylphenyl (R$^1_d$).

Preference is furthermore given to compounds of the formula (I) in which
R$^1$ represents cyclopentyl (R$^1_b$).

Preference is furthermore given to compounds of the formula (I) in which
R$^1$ represents 2-fluoro-4-methoxyphenyl (R$^1_d$).

Preference is furthermore given to compounds of the formula (I) in which
R$^1$ represents 2-bromo-4-fluorphenyl (R$^1_d$).

Preference is furthermore given to compounds of the formula (I) in which
R$^1$ represents 2,6-dimethoxyphenyl (R$^1_d$).

Preference is furthermore given to compounds of the formula (I) in which
R$^1$ represents 2-methylcyclohexyl (R$^1_b$).

Preference is furthermore given to compounds of the formula (I) in which
R$^1$ represents 2-(prop-2-yn-1-yloxy)phenyl (R$^1_d$).

Preference is furthermore given to compounds of the formula (I) in which
R$^1$ represents 2,6-dichlorophenyl (R$^1_d$).

Preference is furthermore given to compounds of the formula (I) in which
R$^1$ represents 2,6-dimethylphenyl (R$^1_d$).

Preference is furthermore given to compounds of the formula (I) in which
R$^1$ represents 2,4,6-trifluorophenyl (R$^1_d$).

Preference is furthermore given to compounds of the formula (I) in which
R$^1$ represents 2-chloro-5-fluorophenyl (R$^1_d$).

Preference is furthermore given to compounds of the formula (I) in which
R$^1$ represents 2-chloro-6-fluorophenyl (R$^1_d$).

Preference is furthermore given to compounds of the formula (I) in which
R$^1$ represents 4-fluorophenyl (R$^1_d$).

Preference is furthermore given to compounds of the formula (I) in which
R$^1$ represents 3-fluorophenyl (R$^1_d$).

Preference is furthermore given to compounds of the formula (I) in which
R$^1$ represents 2-fluorophenyl (R$^1_d$).

The radical definitions mentioned above can be combined with one another as desired. Moreover, individual definitions may not apply.

Depending on the nature of the substituents defined above, the compounds of the formula (I) have acidic or basic properties and can form salts, if appropriate also inner salts, or adducts with inorganic or organic acids or with bases or with metal ions. If the compounds of the formula (I) carry amino, alkylamino or other groups which induce basic properties, these compounds can be reacted with acids to give salts, or they are directly obtained as salts in the synthesis. If the compounds of the formula (I) carry hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $C_1$-$C_4$-alkyl groups, mono-, di- and trialkanolamines of $C_1$-$C_4$-alkanols, choline and also chlorocholine.

The salts obtainable in this manner also have fungicidal, herbicidal and insecticidal properties.

Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as NaHSO$_4$ and KHSO$_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, saturated or mono- or diunsaturated $C_6$-$C_{20}$-fatty acids, sulphuric acid monoalkyl esters, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, salicylic acid, p-aminosalicylic acid, 2-phenoxybenzoic acid, 2-acetoxybenzoic acid, etc.

Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals can be present in the various valencies that they can assume.

Optionally substituted groups can be mono- or polysubstituted, where in the case of polysubstitutions the substituents can be identical or different.

In the definitions of the symbols given in the formulae above, collective terms were used which are generally representative of the following substituents:

halogen: fluorine, chlorine, bromine and iodine;

alkyl: saturated, straight-chain or branched hydrocarbon radicals having 1 to 8 carbon atoms, for example (but not limited thereto) $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkenyl: unsaturated, straight-chain or branched hydrocarbon radicals having 2 to 8 carbon atoms and a double bond in any position, for example (but not limited thereto) $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

alkynyl: straight-chain or branched hydrocarbon groups having 2 to 8 carbon atoms and a triple bond in any position, for example (but not limited thereto) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

alkoxy: saturated, straight-chain or branched alkoxy radicals having 1 to 8 carbon atoms, for example (but not limited thereto) $C_1$-$C_6$-alkoxy, such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

alkylthio: saturated, straight-chain or branched alkylthio radicals having 1 to 8 carbon atoms, for example (but not limited thereto) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

alkoxycarbonyl: an alkoxy group having 1 to 6 carbon atoms (as mentioned above) which is attached to the skeleton via a carbonyl group (—CO—);

alkylsulphinyl: saturated, straight-chain or branched alkylsulphinyl radicals having 1 to 8 carbon atoms, for example (but not limited thereto) $C_1$-$C_6$-alkylsulphinyl, such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropylsulphinyl, 1,2,2-trimethylpropylsulphinyl, 1-ethyl-1-methylpropylsulphinyl and 1-ethyl-2-methylpropylsulphinyl;

alkylsulphonyl: saturated, straight-chain or branched alkylsulphonyl radicals having 1 to 8 carbon atoms, for example (but not limited thereto) $C_1$-$C_6$-alkylsulphonyl, such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl;

cycloalkyl: monocyclic saturated hydrocarbon groups having 3 to 10 carbon ring members, for example (but not limited thereto) cyclopropyl, cyclopentyl and cyclohexyl;

haloalkyl: straight-chain or branched alkyl groups having 1 to 8 carbon atoms (as mentioned above), where in these groups some or all of the hydrogen atoms may be replaced by halogen atoms as mentioned above, for example (but not limited thereto) $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

haloalkoxy: straight-chain or branched alkoxy groups having 1 to 8 carbon atoms (as mentioned above), where in these groups some or all of the hydrogen atoms may be replaced by halogen atoms as mentioned above, for example (but not limited thereto) $C_1$-$C_3$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy;

haloalkylthio: straight-chain or branched alkylthio groups having 1 to 8 carbon atoms (as mentioned above), where in these groups some or all of the hydrogen atoms may be replaced by halogen atoms as mentioned above, for example (but not limited thereto) $C_1$-$C_3$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio;

heteroaryl: a 5 or 6-membered fully unsaturated monocyclic ring system comprising one to four heteroatoms from the group consisting of oxygen, nitrogen and sulphur; if the ring contains a plurality of oxygen atoms, these are not directly adjacent;

5-membered heteroaryl: which contains one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

5-membered heteroaryl which contains one to four nitrogen atoms and is attached via nitrogen or benzo-fused 5-membered heteroaryl which contains one to three nitrogen atoms and is attached via nitrogen: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, in which one or two carbon atoms may be replaced by nitrogen atoms, where these rings are attached to the skeleton via one of the nitrogen ring members, for example (but not limited thereto) 1-pyrrolyl, 1-pyrazolyl, 1,2,4-triazol-1-yl, 1-imidazolyl, 1,2,3-triazol-1-yl, 1,3,4-triazol-1-yl;

6-membered heteroaryl which contains one to four nitrogen atoms: 6-membered heteroaryl groups which, in addition to carbon atoms, may contain, respectively, one to three and one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 5-membered heteroaryl which contains one to three nitrogen atoms or one nitrogen atom and one oxygen or sulphur atom: for example (but not limited thereto) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl, benzo-fused 6-membered heteroaryl which contains one to three nitrogen atoms: for example (but not limited thereto) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl;

heterocyclyl: a three- to fifteen-membered saturated or partially unsaturated heterocycle which contains one to four heteroatoms from the group consisting of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains a plurality of oxygen atoms, these are not directly adjacent; such as, for example (but not limited thereto), oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2, 4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

When combinations of a plurality of radicals are mentioned, such as, for example, Cx-Cy-alkylcarbonyl or Cx-Cy-alkoxyalkyl, the term Cx-Cy denotes in each case the sum of all carbon atoms present in the entire fragment. Here, X and Y each represent an integer, the number Y being greater than the number X.

Not included are combinations which are against natural laws and which the person skilled in the art would therefore exclude based on his/her expert knowledge. Ring structures having three or more adjacent oxygen atoms, for example, are excluded.

Illustration of the Processes and Intermediates

The ketoheteroarylpiperidine and -piperazine derivatives of the formula (I) can be prepared by various routes. The feasible processes are shown Schemetically below. Unless indicated otherwise, the radicals given have the meanings given above.

The processes according to the invention for preparing compounds of the formula (I) are, if appropriate, carried out using one or more reaction auxiliaries.

Suitable reaction auxiliaries are, if required, inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyldiisopropylamine, N,N-dimethylcyclohexylamine, dicyclohexylamine, ethyldicyclohexylamine, N,N-dimethylaniline, N,N-dimethylbenzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methylpyridine, 4-dimethylaminopyridine, N-methylpiperidine, 1,4-diazabicyclo[2.2.2]octane (DABCO), 1,5-diazabicyclo[4.3.0]-non-5-ene (DBN), or 1,8-diazabicyclo[5.4.0]undec-7-ene (DBU).

If appropriate, the processes according to the invention are carried out using one or more diluents. Suitable diluents are virtually all inert organic solvents. These include, in particular, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles such as, for example, acetonitrile and propionitrile, amides such as, for example, dimethylformamide, dimethylacetamide and N-methylpyrrolidone, and also dimethyl sulphoxide, tetramethylene sulphone and hexamethylphosphoramide and DMPU.

In the processes according to the invention, the reaction temperatures can be varied within a relatively wide range. In general, the processes are carried out at temperatures between 0° C. and 250° C., preferably at temperatures between 10° C. and 185° C.

The processes according to the invention are generally carried out at atmospheric pressure. However, it is also possible to work at increased or reduced pressure.

For carrying out the processes according to the invention, the starting materials required are in each case generally employed in approximately equimolar amounts. However, it is also possible to use a relatively large excess of one of the components employed in each case.

Scheme 1: Process A

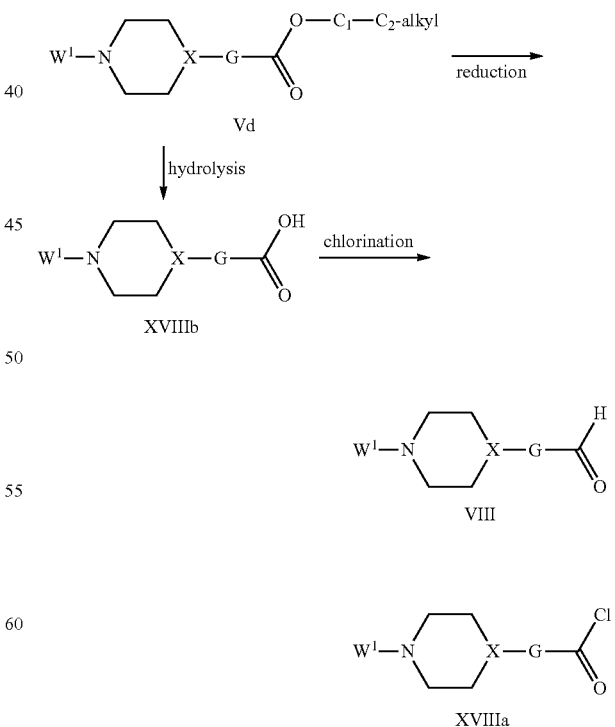

$W^1$ represents acetyl, $C_2$—$C_5$-alkoxycarbonyl, benzyl or benzyloxycarbonyl One way of producing compounds of the formulae (VIII), (XVIIIb) and (XVIIIa) from corresponding compounds (Vd) is shown in Scheme 1.

The compounds of the formula Vd can be prepared from commercially available precursors (see, for example, Figure 1) by procedures described in the literature (see, for example, *Comprehensive Heterocyclic Chemistry*, Vol. 4-6, A. R. Katritzky and C. W. Rees editors, Pergamon Press, New York, 1984; *Comprehensive Heterocyclic Chemistry II*, Vol. 2-4, A. R. Katritzky, C. R. Rees, and E. F. Scruveb editors, Pergamon Press, New York, 1996; and the series, *The Chemistry of Heterocyclic Compounds*, E. C. Taylor, editor, Wiley, New York; WO 2008/064474; WO 2008/006794; WO 2006/133216; U.S. Pat. No. 5,234,033 A; WO 2007/039177; WO 2007/014290; *Org. Biomol. Chem.,* 2008, 1904.)

Figure 1

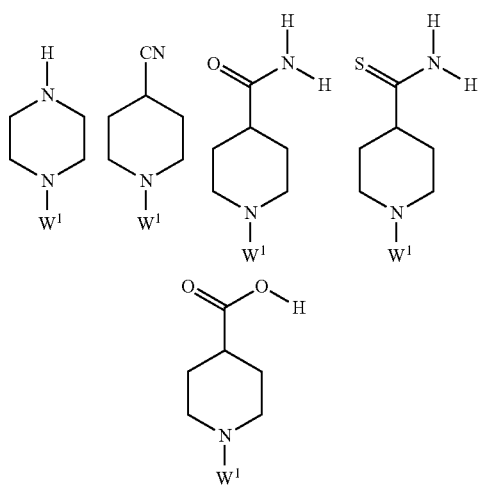

The aldehyde of the formula (VIII) can be prepared from $C_1$-$C_2$-alkyl esters of the formula (Vd) by reduction with reducing agents (for example diisobutylaluminium hydride). The reaction is preferably carried out in tetrahydrofuran at −78° C., under an inert atmosphere (see, for example, *J. Med. Chem.,* 2001, 2319).

The carboxylic acid of the formula (XVIIIb) can be prepared by hydrolysis of the corresponding $C_1$-$C_2$-alkyl ester of the formula (Vd) (cf., for example, WO 2007/014290).

The compounds of the general formula (XVIIIa) are prepared from the corresponding acids of the formula (XVIIIb) by chlorination using processes known from the literature. (for example *Tetrahedron* 2005, 61, 10827-10852, and the literature cited therein).

Scheme 2: Process B

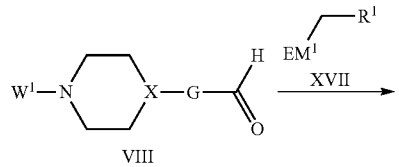

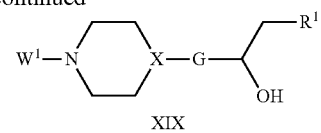

XIX $W^1$ represents acetyl, $C_2$—$C_5$-alkoxycarbonyl, benzyl or benzyloxycarbonyl
$M^1$ represents Li, Mg or Zn
E represents Cl, Br or I One way of preparing compounds of the formula (XIX) from corresponding compounds (VIII) using an organometallic reagent (XVII) is shown in Scheme 2.

The compounds of the formula (XIX) are prepared from the aldehyde of the formula (VIII) by addition of an organometallic reagent $R^1$—$CH_2M^1E$ (XVII), $M^1$=Mg, Li or Zn, E=Cl, Br, or I). The reaction is preferably carried out in tetrahydrofuran or diethyl ether at −78° C.-35° C. Particularly preferably, the reaction is carried out in tetrahydrofuran at −78° C., under an inert atmosphere (see, for example, WO 2007/039177, WO 2006/066109). In the case of organozinc compounds, preference is given to using Lewis acids (for example $BF_3.Et_2O$).

The organometallic reagent (XVII) is commercially available or can be prepared from commercially available precursors by procedures described in the literature (see, for example, "*Handbook of Functionalized Organometallics Vol. 1 and 2*", Ed. P. Knochel, Weinheim, Wiley-VCH, 2005, and references cited therein).

The reaction time varies depending on the scale of the reaction and the reaction temperature, but is generally between a couple of minutes and 48 hours. After the reaction has ended, the compound (XIX) is separated from the reaction mixture using one of the customary separation techniques. If required, the compounds are purified by recrystallization, distillation or chromatography, or they can, if appropriate, also be used for the next step without prior purification.

Scheme 3: Process C

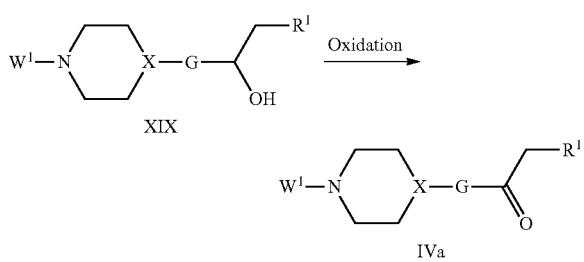

$W^1$ represents acetyl, $C_2$—$C_5$-alkoxycarbonyl, benzyl or benzyloxycarbonyl One way of preparing compounds of the formula (IVa) from compounds (XIX) is shown in Scheme 3.

Compounds of the formula (IVa) are prepared by oxidation of the alcohol (XIX). Numerous methods for preparing ketones from secondary alcohols can be found in the literature (see, for example, "Oxidation of Alcohols to Aldehydes and Ketones", Gabriel Tojo, Marcos Fernandez, Springer Berlin, 2006, pages 1-97, and the literature cited therein). The oxidation is preferably carried out under Swern conditions or using Dess-Martin periodinane (see, for example, *J. Am. Chem. Soc.* 1991, 113, 7277).

Suitable are all solvents which for their part are not oxidized by the oxidizing agent, such as, for example, dichloromethane, chloroform or acetonitrile, if appropriate in the presence of a reaction auxiliary, for example an acid (e.g. sulphuric acid or hydrochloric acid) or else a base (e.g. triethylamine or pyridine).

The reaction is preferably carried out at room temperature. The reaction time varies depending on the scale of the reaction and the reaction temperature, but is generally between a few minutes and 48 hours.

After the reaction has ended, the compound (IVa) is removed from the reaction mixture using one of the customary separation techniques. If required, the compounds are purified by recrystallization, distillation or chromatography, or they can, if appropriate, also be used for the next step without prior purification.

Scheme 4: Process D

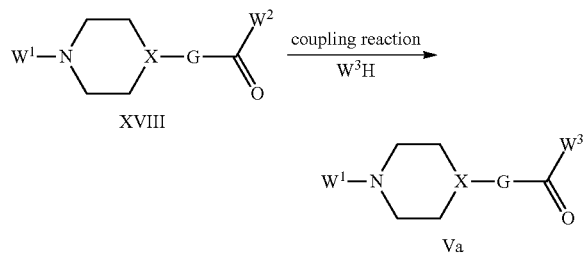

$W^1$ represents acetyl, $C_2$—$C_5$-alkoxycarbonyl, benzyl or benzyloxycarbonyl
$W^2$ = OH or Cl
$W^3$ = NMe$_2$ or NMeOMe One way of preparing compounds of the formula (Va) from corresponding compounds (XVIII) is shown in Scheme 4.

A compound of the general formula (Va) is prepared by a coupling reaction with a compound of the general formula (XVIIIa) (where $W^2$ is chlorine) and with one of the compounds below: N,O-dimethylhydroxamine, N,O-dimethylhydroxamine HCl salt, dialkylamine or dialkylamine HCl salt, if appropriate in the presence of an acid scavenger/a base (see, for example, WO 2008/013622, WO 2008/013925 and WO 2006/018188).

At least one equivalent of an acid scavenger/a base (for example Hünig base, triethylamine or commercially available polymeric acid scavengers), based on the starting material of the general formula (XVIIIa), is employed. If the starting material is a salt, at least two equivalents of the acid scavenger are required.

The reaction is usually carried out at temperatures of 0° C. to 100° C. and preferably at 20° C. to 30° C., but it can also be carried out at the reflux temperature of the reaction mixture. The reaction time varies depending on the scale of the reaction and the reaction temperature, but is generally between a few minutes and 48 hours.

Alternatively, a compound of the formula (Va) can also be synthesized from the corresponding compound of the formula (XVIIIb) (where $W^2$ represents hydroxyl) using N,O-dimethylhydroxamine, N,O-dimethylhydroxamine HCl salt, dialkylamine or dialkylamine HCl salt in the presence of a coupling reagent, analogously to procedures described in the literature (for example *Tetrahedron*, 2005, 61, 10827, and references cited therein).

Suitable coupling reagents are, for example, peptide coupling reagents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

If appropriate, a base, such as, for example, triethylamine or Hünig base can be employed in the reaction.

The reaction is preferably carried out at temperatures of from 0° C. to 100° C. and particularly preferably from 0° C. to 30° C. The reaction time varies depending on the scale of the reaction and the reaction temperature, but is generally between a number of minutes and 48 hours.

The process D according to the invention is preferably carried out using one or more diluents. After the reaction has ended, the compounds (Va) are removed from the reaction mixture using one of the customary separation techniques. If required, the compounds are purified by recrystallization, distillation or chromatography, or they can, if appropriate, also be used for the next step without prior purification.

Scheme 5: Process E

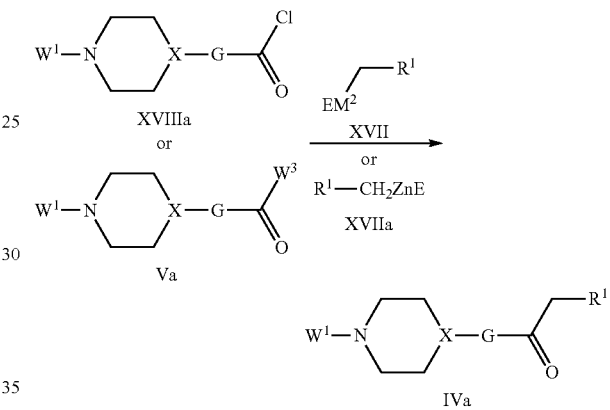

$W^1$ represents acetyl, $C_2$—$C_5$-alkoxycarbonyl, benzyl or benzyloxycarbonyl
$W^3$ represents NMeOMe or NMe$_2$
$M^2$ represents Li or Mg
E represents Cl, Br or I One way of preparing compounds of the formula (IVa) from corresponding compounds (Va) or (XVIIIa) using an organometallic reagent (XVII or XVIIa) is shown in Scheme 5.

The compounds of the formula (IVa) are prepared from the amide (Va), where $W^3$ represents NMeOMe or NMe$_2$ by addition of an organometallic reagent $R^1$—CH$_2$M$^2$E (XVII), $M^2$=Mg or Li). The reaction is preferably carried out in tetrahydrofuran at −78° C., under an inert atmosphere (see, for example, *J. Med. Chem.*, 2009, 52, 1701).

(Va) and the organometallic reagent (where $M^2$=Mg or Li) are employed in equimolar amounts; however, if appropriate, the organometallic reagent can also be used in excess. The reaction is preferably carried out at room temperature. The reaction time varies depending on the scale of the reaction and the reaction temperature, but is generally between a few minutes and 48 hours.

Alternatively, the compounds of the formula (IVa) are prepared from the chloride (XVIIIa) by addition of an organozinc reagent (XVIIa), $R^1$—CH$_2$ZnE (E=Cl, Br, or I), if appropriate in the presence of a palladium catalyst. Preferably, the reaction is carried out in the presence of Pd(PPh$_3$)$_4$ or PdCl$_2$ in tetrahydrofuran at room temperature, under an inert atmosphere (see, for example, WO 2007/070818; *Org. Lett.*, 2008, 10, 1107). The amount of catalyst used is 0.1-90 mol % based on the starting material; preferably, 1-30 mol % of the catalyst, based on the starting material, are used.

(XVIIIa) and the organozinc compound are used in equimolar amounts. However, the organozinc compound can also be used in excess. The reaction time varies depending on the scale of the reaction and the reaction temperature, but is generally between a few minutes and 48 hours.

The process E according to the invention is preferably carried out using one or more diluents. After the reaction has ended, the compound (IVa) is removed from the reaction mixture using one of the customary separation techniques. If required, the compounds are purified by recrystallization, distillation or chromatography, or they can, if appropriate, also be used for the next step without prior purification.

Scheme 6: Process F

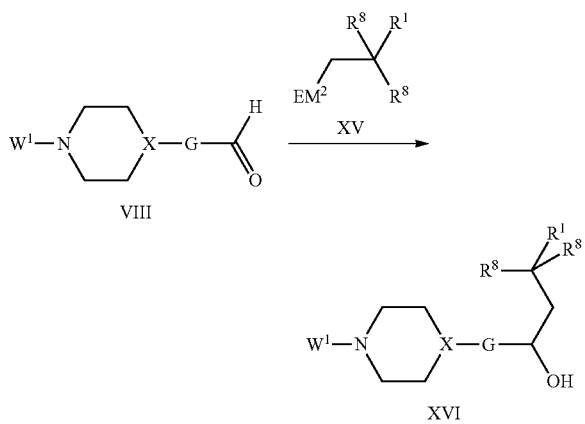

$W^1$ represents acetyl, $C_2$—$C_5$-alkoxycarbonyl, benzyl or benzyloxycarbonyl
$M^2$ represents Mg or Li
E represents Cl, Br or I One way of preparing compounds of the formula (XVI) from corresponding compounds (VIII) using an organometallic reagent (XV) is shown in Scheme 6.

Process F is carried out analogously to process B (see above).

Scheme 7: Process G

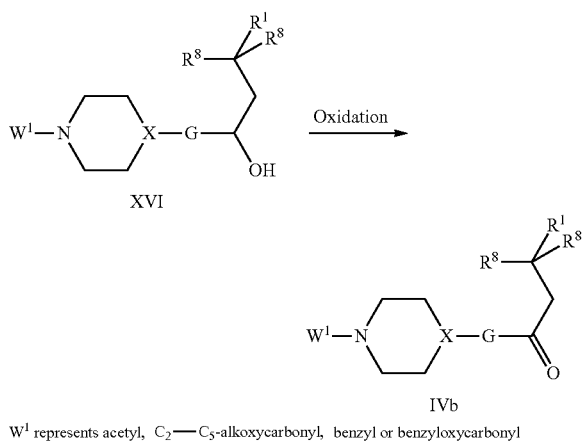

$W^1$ represents acetyl, $C_2$—$C_5$-alkoxycarbonyl, benzyl or benzyloxycarbonyl One way of preparing compounds of the formula (IVb) from corresponding compounds (XVI) is shown in Scheme 7.

Process G is carried out analogously to process C (see above).

Scheme 8: Process H

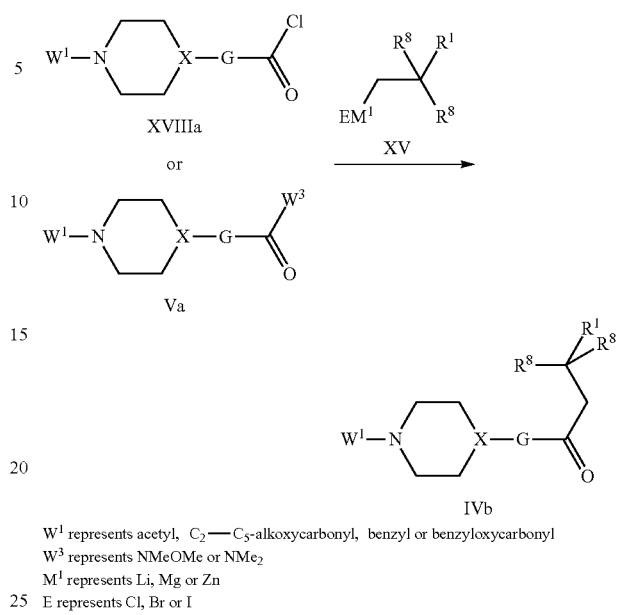

$W^1$ represents acetyl, $C_2$—$C_5$-alkoxycarbonyl, benzyl or benzyloxycarbonyl
$W^3$ represents NMeOMe or $NMe_2$
$M^1$ represents Li, Mg or Zn
E represents Cl, Br or I One way of preparing compounds of the formula (IVb) from corresponding compounds (Va) or (XVIIIa) using an organometallic reagent (XV) is shown in Scheme 8.

Process H is carried out analogously to process E (see above).

Scheme 9: Process I

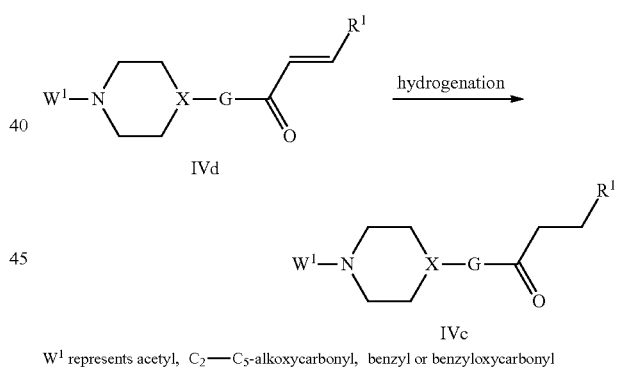

$W^1$ represents acetyl, $C_2$—$C_5$-alkoxycarbonyl, benzyl or benzyloxycarbonyl One way of preparing the intermediate (IVc) from compound (IVd) is shown in Scheme 9.

By hydrogenation using a suitable catalyst, a double bond is converted into a single bond. The catalyst for process I is selected from the hydrogenation catalysts known from the literature for hydrogenation ("*Reductions in Organic Chemistry*", Miloš Hudlický, John Wiley & Sons, 1984), such as, for example, palladium on activated carbon or Pearlmans catalyst ($Pd(OH)_2$ on activated carbon).

The process I according to the invention is preferably carried out using one or more diluents. Preferred solvents are N,N-dimethylformamide, ethyl acetate and ethanol.

The amount of catalyst used is 0.1-90 mol % based on the starting material; preferably, 1-30 mol % of the catalyst, based on the starting material, are used. The reaction can be carried out at superatmospheric pressure (1-1000 bar) or preferably at atmospheric pressure. The reaction is preferably carried out at temperatures of 0° C.-150° C. and particularly preferably at room temperature. The reaction time varies depending on the scale of the reaction and the reaction temperature, but is generally between half an hour and 72 hours.

After the reaction has ended, the compounds (IVc) are separated from the reaction mixture by one of the customary separation techniques. If required, the compounds are purified by recrystallization, distillation or chromatography, or they can, if appropriate, also be used for the next step without prior purification.

Scheme 10: Process J

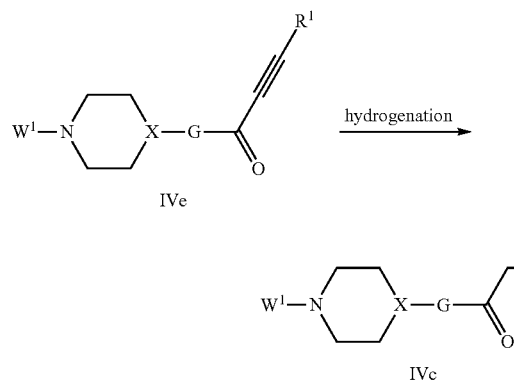

$W^1$ represents acetyl, $C_2$—$C_5$-alkoxycarbonyl, benzyl or benzyloxycarbonyl One way of preparing compounds of the formula (IVc) from corresponding compounds (We) is shown in Scheme 10.

By hydrogenation using a suitable catalyst, a triple bond is converted into a single bond.

The same process as already described in Scheme 9 (process I) is employed.

Scheme 11: Process K

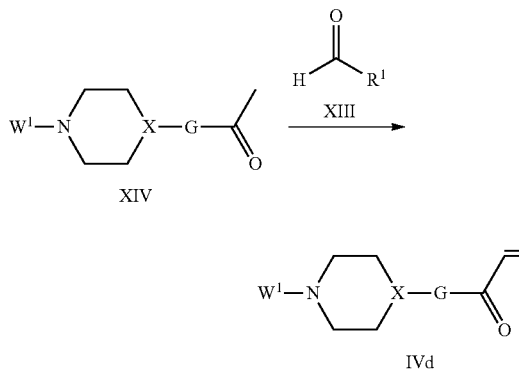

$W^1$ represents acetyl, $C_2$—$C_5$-alkoxycarbonyl, benzyl or benzyloxycarbonyl One way of preparing compounds of the formula (IVd) from corresponding compounds (XIV) using an aldehyde (XIII) is shown in Scheme 11.

Compounds (XIV) can be synthesized from compounds (VIII) by initially applying process B and then process C to compounds of the formula (XIII).

Compounds (XIV) can be synthesized from compounds (Va) by initially applying process E to compounds of the formula (Va).

The aldehyde (XIII) is commercially available or can be prepared from commercially available precursors by procedures described in the literature.

A compound of the general formula (IVd) can be synthesized by an aldol condensation of a compound having the corresponding general formula (XIV) with an aldehyde (XIII) in the presence of an acid or base (see, for example, *Synthetic Communications,* 2009, 39, 2789; *Organic Letters,* 2009, 11, 3562; *Pharmazie,* 1988, 43, 82).

Suitable bases are, for example, LiOH, NaOH or KOH, for example in the presence of water together with a cosolvent, preferably THF, toluene and/or methanol, to facilitate dissolution of the ester. The starting material and the base are employed in equimolar amounts; however, the base may, if required, also be used in excess or in catalytic amounts.

Suitable acids are, for example, $H_2SO_4$ or HCl, for example in the presence of water together with a cosolvent, preferably THF, toluene and/or methanol, to facilitate dissolution of the ester. The starting material and the acid are employed in equimolar amounts; however, the acid may, if required, also be used in excess or in catalytic amounts.

(XIV) and (XIII) are used in equimolar amounts. However, if appropriate, the aldehyde (XIII) may also be used in excess. The reaction is preferably carried out at temperatures of from 0° C. to 100° C. and particularly preferably at room temperature. The reaction time varies depending on the scale of the reaction and the reaction temperature, but is generally between a few minutes and 48 hours.

The process K according to the invention is preferably carried out using one or more diluents. After the reaction has ended, the compound (IVd) is removed from the reaction mixture using one of the customary separation techniques. If required, the compounds are purified by recrystallization, distillation or chromatography, or they can, if appropriate, also be used for the next step without prior purification.

Scheme 12: Process L

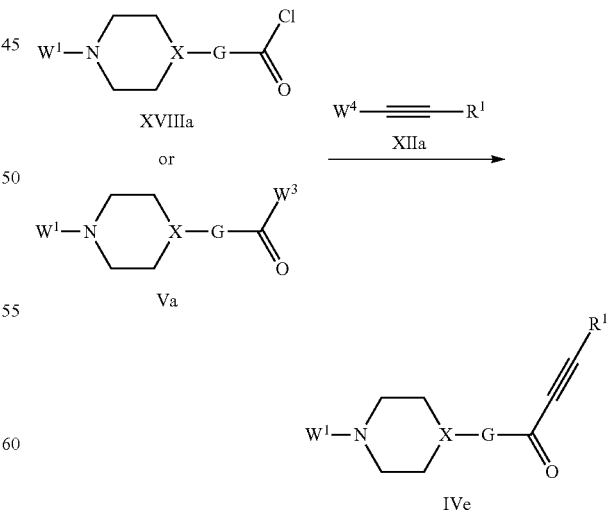

$W^1$ represents acetyl, $C_2$—$C_5$-alkoxycarbonyl, benzyl or benzyloxycarbonyl
$W^3$ represents NMeOMe or $NMe_2$
W4 represents H, ZnE, MgE or Li, E represents Cl, Br or I One way of preparing compounds of the formula (IVe) from corresponding compounds (Va or XVIIIa) using an alkyne of the formula (XIIa) is shown in Scheme 12.

Analogously to the method described above (process E), it is possible to synthesize, using an organometallic reagent (XVIIa), where $W^4$ represents ZnE, MgE or Li, the compounds (IVe) from compounds (Va).

The organometallic reagent (XIIA) is commercially available or can be prepared from commercially available precursors by procedures described in the literature (see, for example, "*Handbook of Functionalized Organometallics Vol. 1 and 2*", Ed. P. Knochel, Weinheim, Wiley-VCH, 2005, and references cited therein).

Alternatively, a compound of the general formula (IVe) can be prepared from the starting material of the formula (XVIIIa) by a palladium-catalysed crosscoupling analogously to the procedures described in the literature (see, for example, *Synthesis*, 2003, 2815). Preferably, (XVIIIa) is converted into the ketone (IVe) using an alkyne of the formula (XIIa), where $W^4$ is H in the presence of a catalyst such as, for example, [(π-allyl)PdCl]$_2$, Pd(OAc)$_2$, PdCl$_2$(CH$_3$CN)$_2$, Pd(PPh$_3$)$_4$ or PdCl$_2$(PPh$_3$)$_2$ and also, if appropriate, in the presence of further cocatalysts such as, for example, CuI, Cs$_2$CO$_3$ and triethylamine, for example in a solvent mixture of DMF or THF at 0-80° C. and under an inert atmosphere. The amount of catalyst used is 0.1-90 mol % based on the starting material; preferably, 0.5-30 mol % of the catalyst, based on the starting material, are used.

The alkyne (XIIa) is commercially available or can be prepared from commercially available precursors by procedures described in the literature.

The process L according to the invention is preferably carried out using one or more diluents. After the reaction has ended, the compound (IVe) is removed from the reaction mixture using one of the customary separation techniques. If required, the compounds are purified by recrystallization, distillation or chromatography, or they can, if appropriate, also be used for the next step without prior purification.

Scheme 13: Process M

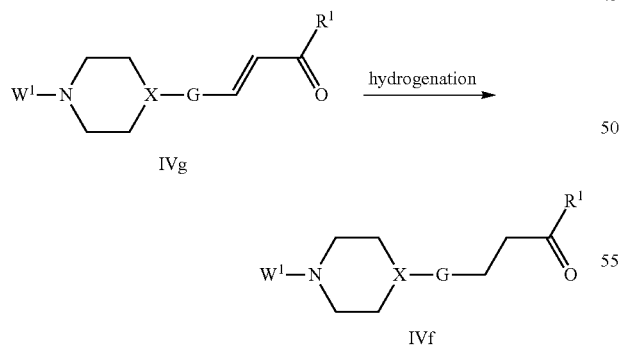

$W^1$ represents acetyl, $C_2$—$C_5$-alkoxycarbonyl, benzyl or benzyloxycarbonyl One way of preparing compounds of the formula (IVf) from corresponding compounds (IVg) is shown in Scheme 13.

The same process as already described in Scheme 9 (process I) is employed.

Scheme 14: Process N

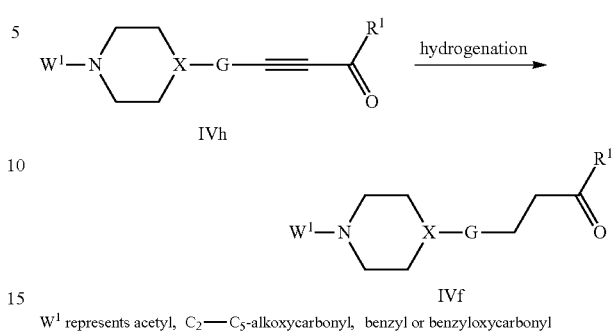

$W^1$ represents acetyl, $C_2$—$C_5$-alkoxycarbonyl, benzyl or benzyloxycarbonyl One way of preparing compounds of the formula (IVf) from corresponding compounds (IVh) is shown in Scheme 14.

The same process as already described in Scheme 9 (process I) is employed.

Scheme 15: Process O

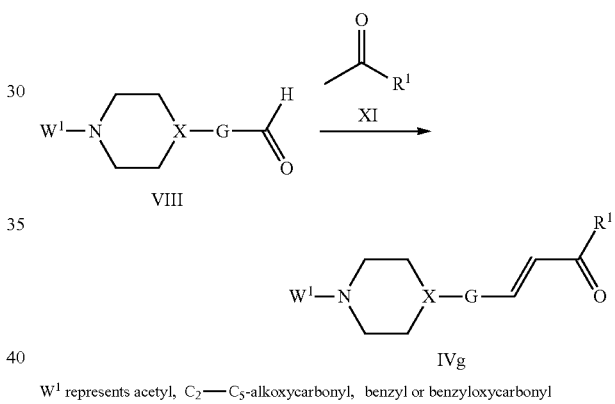

$W^1$ represents acetyl, $C_2$—$C_5$-alkoxycarbonyl, benzyl or benzyloxycarbonyl One way of preparing compounds of the formula (IVg) from corresponding compounds (VIII) using a ketone (XI) is shown in Scheme 15.

Process O is carried out analogously to process K.

Scheme 16: Process P

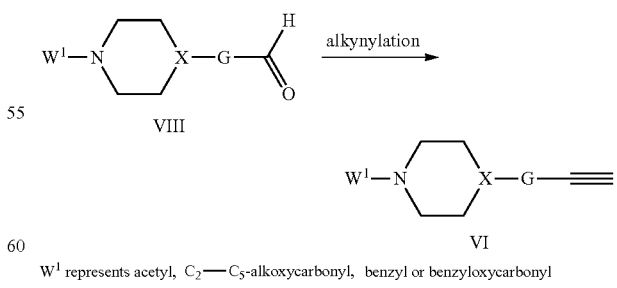

$W^1$ represents acetyl, $C_2$—$C_5$-alkoxycarbonyl, benzyl or benzyloxycarbonyl One way of preparing the intermediate (VI) from compound (VIII) is shown in Scheme 16.

From the literature, it is known that alkynylations of aldehydes can be achieved by a Corey-Fuchs reaction (*Tetrahe-*

*dron Lett.,* 1972, 36, 3769) or a Seyferth-Gilbert homologization (see, for example, *J. Org. Chem.,* 1996, 61, 2540). Alternatively, the alkyne (VI) can also be prepared from the aldehyde (VIII) using Bestmann-Ohira's reagent analogously to literature procedures (see, for example, *Synthesis,* 2004, 59). Preferably, alkynylations are carried out using Bestmann-Ohira's reagent in methanol or ethanol in the presence of potassium carbonate or sodium carbonate.

The process P according to the invention is preferably carried out using one or more diluents. All known bases can be used in the reaction. At least one equivalent of the base (for example alkali metal and alkaline earth metal oxides, hydroxides and carbonates) has to be added to the Bestmann-Ohira reagent, and the base may be used in excess, if appropriate.

The aldehyde (VIII) and the alkynylating reagent are employed in equimolar amounts; however, the Bestmann-Ohira reagent can, if appropriate, be used in excess. The reaction is preferably carried out at temperatures of from −100° C. to 60° C. and particularly preferably from −78° C. to 40° C. The reaction time varies depending on the scale of the reaction and the reaction temperature, but is generally between a number of minutes and 48 hours.

After the reaction has ended, the compounds (VI) are removed from the reaction mixture using one of the customary separation techniques. If required, the compounds are purified by recrystallization, distillation or chromatography, or they can, if appropriate, also be used for the next step without prior purification.

Scheme 17: Process Q

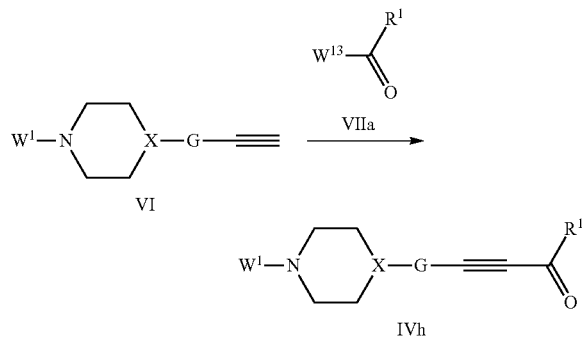

$W^1$ represents acetyl, $C_2$—$C_5$-alkoxycarbonyl, benzyl or benzyloxycarbonyl
$W^{13}$ represents Cl, NMeOMe or $C_2$—$C_6$-dialkylamine One way of preparing compounds of the formula (IVh) from corresponding compounds (VI) using a compound of the formula (VIIa) is shown in Scheme 17.

Process Q is carried out analogously to process L.

Scheme 18: Process R

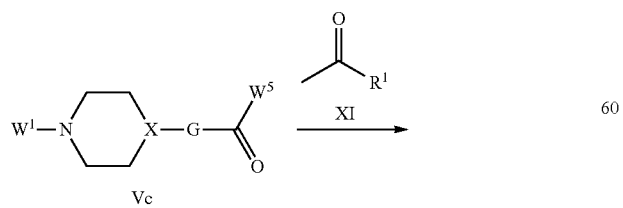

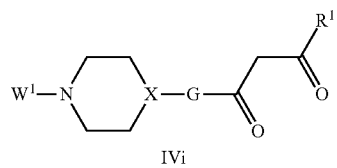

$W^1$ represents acetyl, $C_2$—$C_5$-alkoxycarbonyl, benzyl or benzyloxycarbonyl
$W^5$ represents methoxy, ethoxy, chlorine, N(Me)OMe One way of preparing compounds of the formula (IVi) from corresponding compounds (Vc) using a ketone (XI) is shown in Scheme 18.

A compound of the general formula (IVi) can be synthesized by the reaction of a compound having the corresponding general formula (Vc) with a ketone (XI) in the presence of a base (see, for example, WO 2008/004100; *Bioorganic & Medicinal Chemistry Letters,* 2008, 18(17), 4859).

All known suitable bases may be employed. Preference is given to using lithium hexamethyldisilazide, sodium hexamethyldisilazide, potassium hexamethyldisilazide, sodium methoxide, potassium methoxide, sodium ethoxide, potassium ethoxide and lithium diisopropylamide for the reaction. Preferably, at least one equivalent of the base has to be added to the ketone of the general formula (XI); if appropriate, the base may be added in excess.

The process R according to the invention is preferably carried out using one or more diluents.

The compound (Vc) and the ketone (XI) are employed in equimolar amounts. The reaction is preferably carried out at temperatures of from −100° C. to 100° C. and particularly preferably from −78° C. to 40° C. The reaction time varies depending on the scale of the reaction and the reaction temperature, but is generally between a number of minutes and 48 hours.

After the reaction has ended, the compounds (IVi) are separated from the reaction mixture by one of the customary separation techniques. If required, the compounds are purified by recrystallization, distillation or chromatography, or they can, if appropriate, also be used for the next step without prior purification.

Scheme 19: Process S

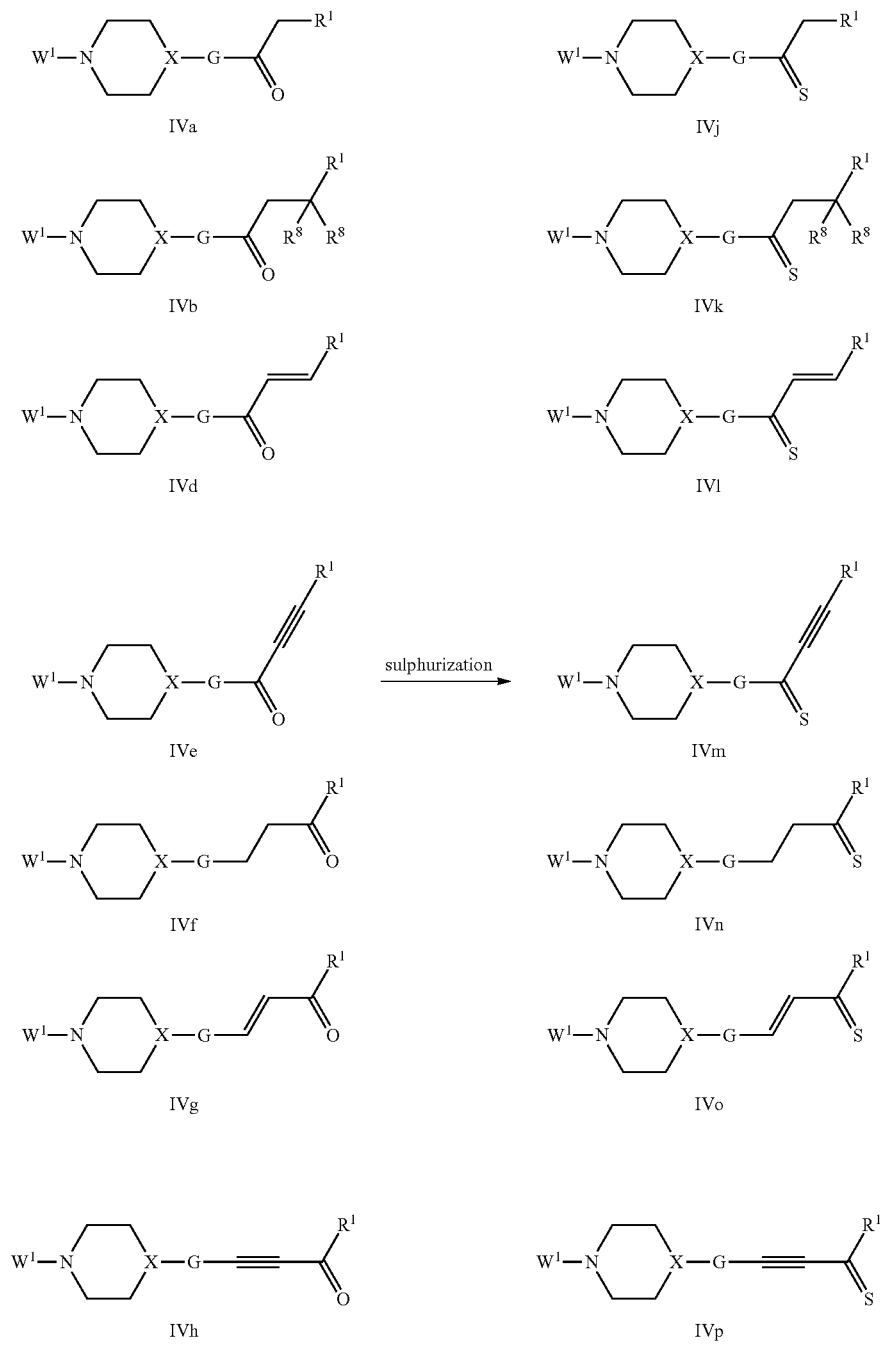

$W^1$ represents acetyl, $C_1$—$C_4$-alkoxycarbonyl, benzyl or benzyloxycarbonyl One way of preparing compounds of the formulae (IVj)-(IVp) from corresponding compounds (IVa), (IVb), (IVd)-(IVh) is shown in Scheme 19.

The process S according to the invention is preferably carried out using one or more diluents. The preferred solvents are chloroform and 1,2-dimethoxyethane.

Suitable sulphurizing agents are, for example, Lawesson's reagent (see *Tetrahedron* 1986, 42, 6555-6564, *Tetrahedron Lett.* 1993, 46, 7459-7462) and phosphorus pentasulphide. The starting material and the sulphurizing agent are employed in equimolar amounts; however, the sulphurizing agent may, if required, also be used in excess.

The reaction is preferably carried out at temperatures of 0° C.-150° C. and particularly preferably from 0° C. to 100° C. The reaction time varies depending on the scale of the reaction and the reaction temperature, but is generally between a number of minutes and 48 hours.

After the reaction has ended, the compounds (IVj)-(IVp) are removed from the reaction mixture using one of the customary separation techniques. If required, the compounds are purified by recrystallization, distillation or chromatography.

Scheme 20: Process T

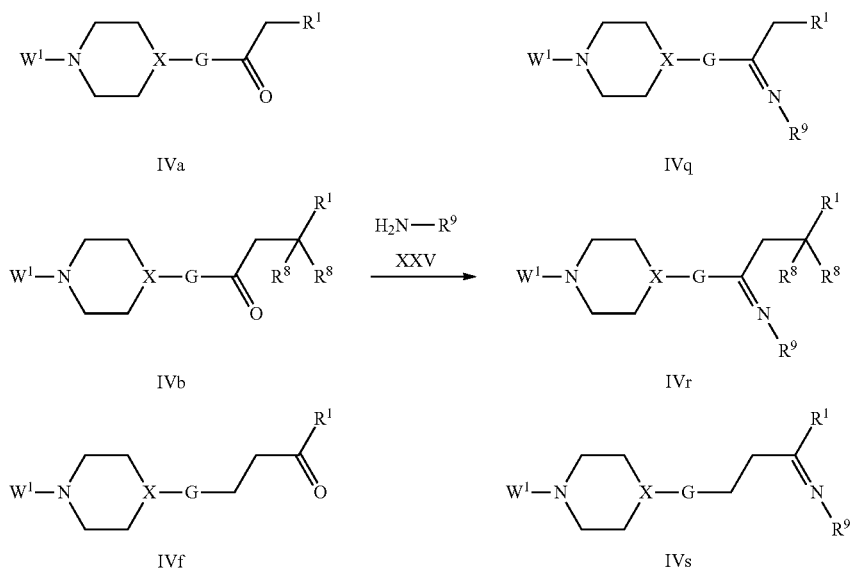

W¹ represents acetyl, C₂—C₅-alkoxycarbonyl, benzyl or benzyloxycarbonyl

A compound of the general formula (IVq)-(IVs) can be synthesized by a condensation reaction of a compound of the corresponding general formula (IVa), (IVb) or (IVf) with a substrate of the general formula (XXV), if appropriate in the presence of an acid, an acid scavenger/a base or a basic ion exchanger.

The compound (XXV) or the corresponding hydrochloric acid salts are commercially available or can be prepared by processes described in the literature (see, for example, *Chem. Eur. J.* 2005, 11, 6974-6981 and *Chem. Soc. Rev.,* 2001, 30, 205-213).

If appropriate, an acid such as, for example, hydrochloric acid or a base such as, for example, triethylamine, Hünig base or a basic ion exchanger such as, for example, Amberlyst A21 may be used in the reaction.

The process T according to the invention is preferably carried out using one or more diluents. The preferred solvent is ethanol.

The reaction is preferably carried out at temperatures of 0° C.-100° C. and particularly preferably from 0° C.-30° C. The reaction time varies depending on the scale of the reaction and the reaction temperature, but is generally between a number of minutes and 48 hours.

After the reaction has ended, the compounds (IVq)-(IVs) are removed from the reaction mixture using one of the customary separation techniques. If required, the compounds are purified by recrystallization, distillation or chromatography, or they can, if appropriate, also be used for the next step without prior purification.

Scheme 21: Process U

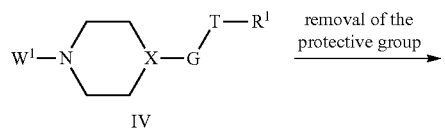

-continued

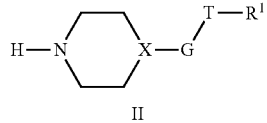

W¹ represents acetyl, C₂—C₅-alkoxycarbonyl, benzyl or benzyloxycarbonyl

One way of preparing compounds of the formula (II) from corresponding compounds (IV) is shown in Scheme 21.

A compound of the formula (II) is converted into a compound of the formula (IV) using suitable methods for removing protective groups, which methods are described in the literature ("*Protective Groups in Organic Synthesis*"; Third Edition; 1999, 494, and the literature cited therein).

tert-Butoxycarbonyl and benzyloxycarbonyl protective groups can be removed in an acidic medium (for example using hydrochloric acid or trifluoroacetic acid). Acetyl protective groups can be removed under basic conditions (using, for example, potassium carbonate or caesium carbonate). Benzylic protective groups can be removed hydrogenolytically using hydrogen in the presence of a catalyst (for example palladium on activated carbon).

Acids which can be used for this reaction of deprotecting t-butoxycarbonyl and benzyloxycarbonyl groups are, for example, trifluoroacetic acid, hydrochloric acid or other acids, as described in the literature (for example "Protective Groups in Organic Synthesis"; Third Edition; 1999; p. 494).

The process U according to the invention is preferably carried out using one or more diluents. The reaction is preferably carried out at temperatures of from 0° C. to +150° C. and particularly preferably at room temperature. The reaction time varies depending on the scale of the reaction and the reaction temperature, but is generally between half an hour and 72 hours.

After the reaction has ended, the compounds (II) are removed from the reaction mixture using one of the customary separation techniques. If required, the compounds are purified by recrystallization, distillation or chromatography, or they can, if appropriate, also be used for the next step without prior purification. Moreover, it is possible to isolate the compound of the general formula (II) as a salt, for example as hydrochloride or trifluoroacetate.

Scheme 22: Process V

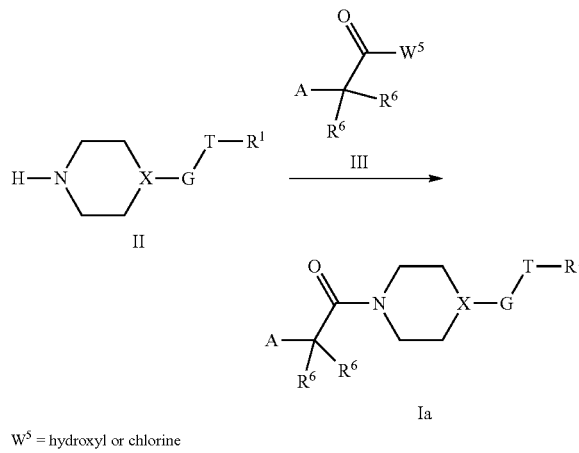

W⁵ = hydroxyl or chlorine

One way of preparing compounds of the formula (Ia) from corresponding compounds (II) using the compounds (III) is shown in Scheme 22.

Compounds (III) can be prepared by processes described in the literature (see, for example, WO 2008/013622 and WO 2008/013925).

A compound of the general formula (Ia) can be synthesized analogously to procedures described in the literature (see, for example, WO 2007/147336) by a coupling reaction of a compound of the corresponding general formula (II) with a substrate of the general formula (III), where W⁵ represents chlorine, if appropriate in the presence of an acid scavenger/a base.

At least one equivalent of an acid scavenger/a base (for example Hünig base, triethylamine or commercially available polymeric acid scavengers), based on the starting material of the general formula (II) is employed. If the starting material is a salt, at least two equivalents of the acid scavenger are required.

The starting materials are employed in equimolar amounts. The reaction is preferably carried out at temperatures of from 0° C. to 100° C. and particularly preferably at from 20° C. to 30° C. The reaction time varies depending on the scale of the reaction and the reaction temperature, but is generally between a few minutes and 48 hours.

Alternatively, a compound of the formula (Ia) can also be synthesized from the corresponding compound of the formula (II) using a substrate of the formula (III), where W⁵ represents hydroxyl in the presence of a coupling agent analogously to procedures described in the literature (for example Tetrahedron 2005, 61, 10827-10852, and the references cited therein).

Suitable coupling agents are, for example, peptide coupling agents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

The reaction is preferably carried out at temperatures of from 0° C. to 100° C. and particularly preferably from 0° C. to 30° C. The reaction time varies depending on the scale of the reaction and the reaction temperature, but is generally between a number of minutes and 48 hours.

The process V according to the invention is preferably carried out using one or more diluents. After the reaction has ended, the compounds (Ia) are removed from the reaction mixture using one of the customary separation techniques. If required, the compounds are purified by recrystallization, distillation or chromatography.

Scheme 23: Process W

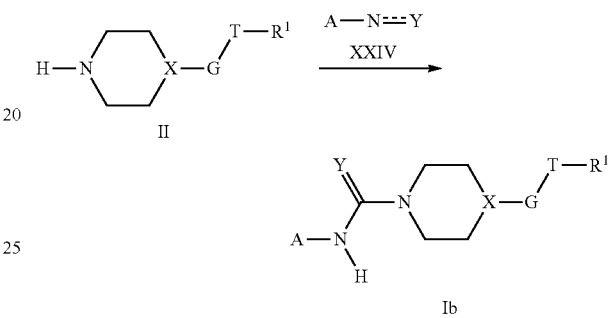

One way of preparing compounds of the formula (Ib) from corresponding compounds (II) using the compounds (XXIV) is shown in Scheme 23.

A compound of the general formula (Ib) can be synthesized analogously to procedures described in the literature (see, for example, WO 2009/055514) by a coupling reaction of a compound of the corresponding general formula (II) with a substrate of the general formula (XXIV), if appropriate in the presence of an acid scavenger/a base such as, for example, triethylamine, 1,8-diazabicyclo[5.4.0]undec-7-ene or Hünig base.

The process W according to the invention is preferably carried out using one or more diluents.

The starting materials are employed in equimolar amounts. The reaction is preferably carried out at temperatures of from 0° C. to 100° C. and particularly preferably from 20° C. to 30° C. The reaction time varies depending on the scale of the reaction and the reaction temperature, but is generally between a number of minutes and 48 hours.

After the reaction has ended, the compounds (Ib) are removed from the reaction mixture using one of the customary separation techniques. If required, the compounds are purified by recrystallization, distillation or chromatography.

Scheme 24: Process X

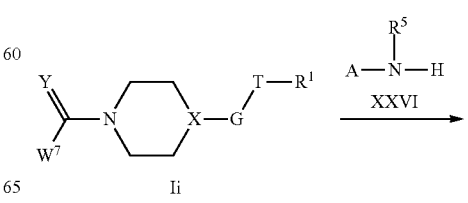

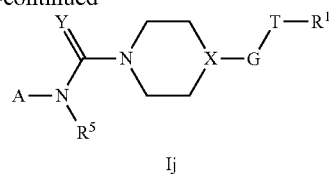

Ij $W^7$ represents chlorine or imidazol-1-yl

The carbamoyl and thiocarbamoyl chlorides of the formula (Ii, $W^7$=chlorine) required as starting materials for carrying out the process according to the invention can be prepared by methods described in the literature (see, for example, *Tetrahedron*, 2008, 7605; *Journal of Organic Chemistry*, 2004, 3787; *Journal of Organic Chemistry*, 1983, 4750; *European Journal of Organic Chemistry*, 2006, 1177). Typically, the compounds of the formula (Ii, $W^7$=chlorine) are prepared from amines of the formula (II) and phosgene, thiophosgene or equivalents thereof.

The carbamoyl- and thiocarbamoylimidazoles of the formula (Ii, $W^7$=imidazol-1-yl) required as starting materials for carrying out process X according to the invention can be prepared by methods described in the literature (see, for example, *Tetrahedron Letters*, 2008, 5279; *Tetrahedron*, 2005, 7153). Typically, the compounds of the formula (Ii, $W^7$=imidazol-1-yl) are prepared from amines of the formula (II) and 1,1'-carbonyldiimidazoles or 1,1'-thiocarbonyldiimidazoles.

Process X describes the preparation of compounds of the structure (Ij) by reaction of compounds of the structure (Ii, $W^7$=chlorine or imidazol-1-yl) and amines (XXVI).

If appropriate, process X is carried out in the presence of a suitable acid acceptor. Suitable acid acceptors are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Alternatively, some of the compounds (Ij) obtained when carrying out process X according to the invention can also be obtained without the use of an acid acceptor as corresponding acid chlorides [(Ij)-HCl] (starting material: $W^7$=Cl). If required, the compounds (Ij) are released by customary methods.

The process X according to the invention is preferably carried out using one or more diluents. The starting materials are employed in equimolar amounts. The reaction is preferably carried out at temperatures of from 0° C. to 100° C. and particularly preferably at from 20° C. to 30° C. The reaction time varies depending on the scale of the reaction and the reaction temperature, but is generally between a few minutes and 48 hours.

After the reaction has ended, the compounds (Ij) are removed from the reaction mixture using one of the customary separation techniques. If required, the compounds are purified by recrystallization, distillation or chromatography.

Scheme 25: Process Y

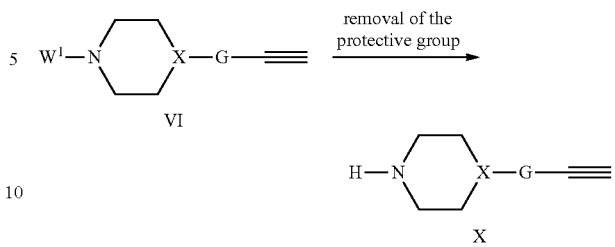

$W^1$ represents acetyl, $C_2$—$C_5$-alkoxycarbonyl, benzyl or benzyloxycarbonyl One way of preparing compounds of the formula (X) from corresponding compounds (VI) is shown in Scheme 25.

Process Y is carried out analogously to process L.

Scheme 26: Process Z

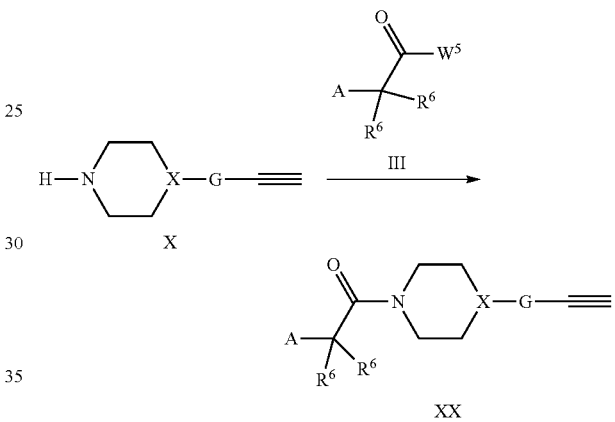

$W^5$ = hydroxyl or chlorine

One way of preparing compounds of the formula (XX) from corresponding compounds (X) is shown in Scheme 26.

The same process as already described in Scheme 22 (process V) is employed.

Scheme 27: Process AA

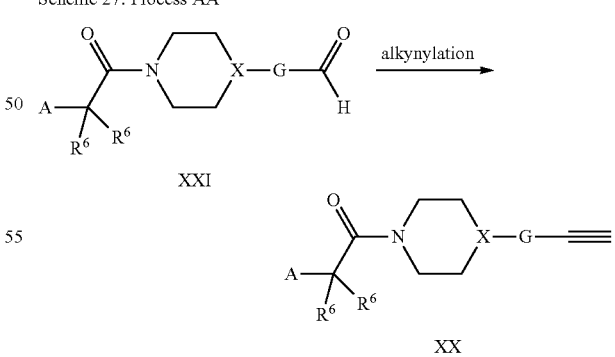

$W^5$ = hydroxyl or chlorine

One way of preparing compounds of the formula (XX) from corresponding compounds (XXI) is shown in Scheme 27.

The same process as already described in Scheme 16 (process P) is employed.

Scheme 28: Process BB

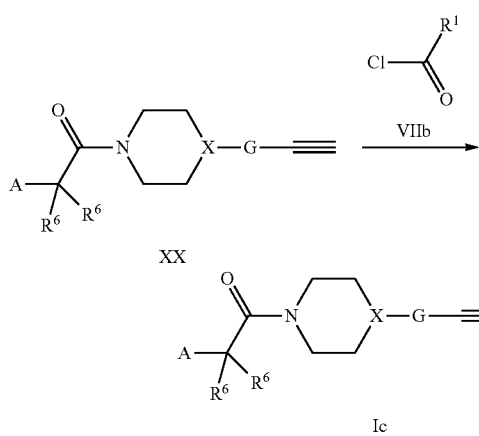

One way of preparing compounds of the formula (Ic) from corresponding compounds (XX) is shown in Scheme 28.

The same process as already described in Scheme 12 (process L) is employed.

Scheme 29: Process CC

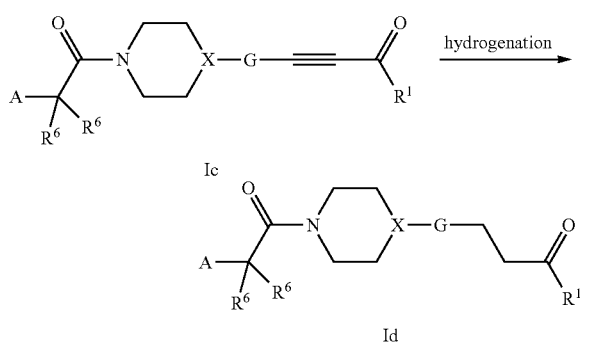

One way of preparing compounds of the formula (Id) from corresponding compounds (Ic) is shown in Scheme 29: process CC.

The same process as already described in Scheme 9 (process I) is employed.

Scheme 30: Process DD

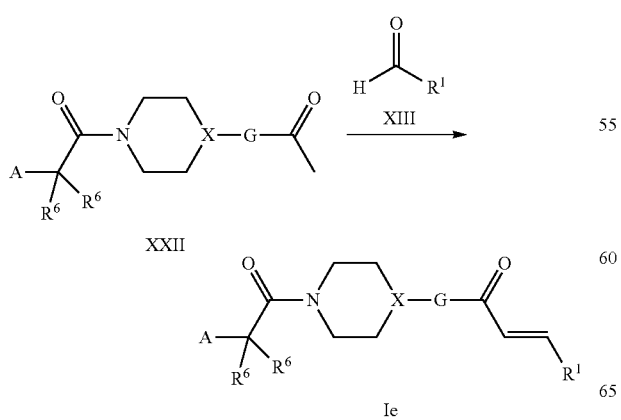

One way of preparing compounds of the formula (Ie) from corresponding compounds (XXII) using a compound of the formula (XIII) is shown in Scheme 30.

The same process as already described in Scheme 11 (process K) is employed.

Scheme 31: Process EE

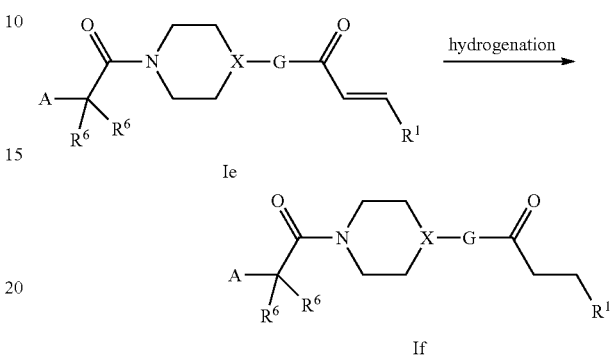

One way of preparing compounds of the formula (If) from corresponding compounds (Ie) is shown in Scheme 31.

The same process as already described in Scheme 9 (process I) is employed.

Scheme 32: Process FF

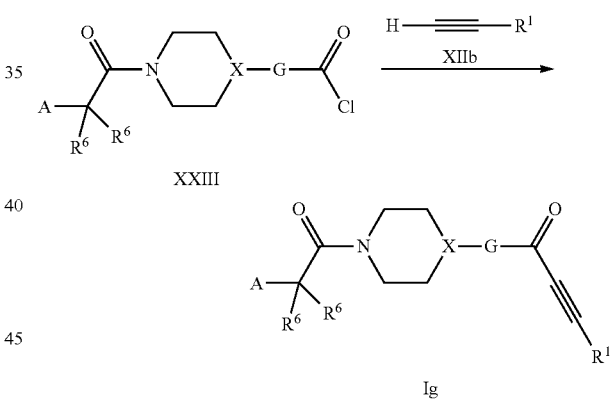

One way of preparing compounds of the formula (Ig) from corresponding compounds (XXIII) using a compound of the formula (XIIb) is shown in Scheme 32.

The same process as already described in Scheme 12 (process L) is employed.

Scheme 33: Process GG

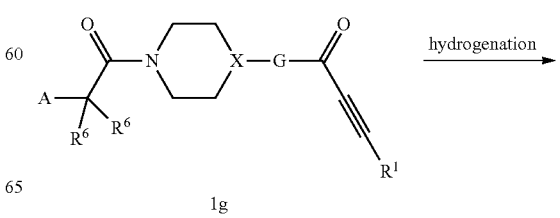

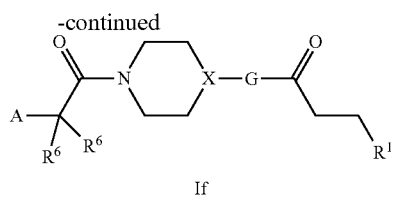

If

One way of preparing compounds of the formula (If) from corresponding compounds (Ig) is shown in Scheme 33.

The same process as already described in Scheme 9 (process I) is employed.

Scheme 34: Process HH

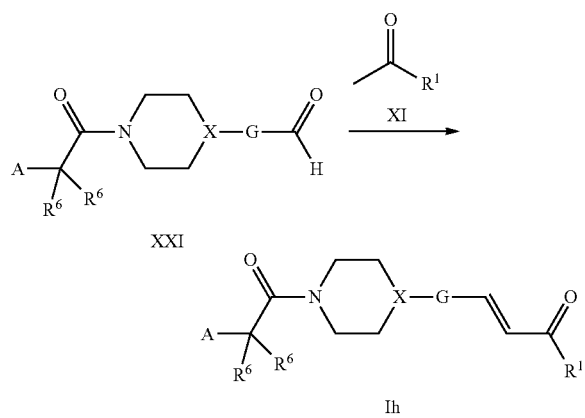

One way of preparing compounds of the formula (Ih) from corresponding compounds (XXI) using a ketone (XI) is shown in Scheme 34.

The same process as already described in Scheme 11 (process K) is employed.

Scheme 35: Process II

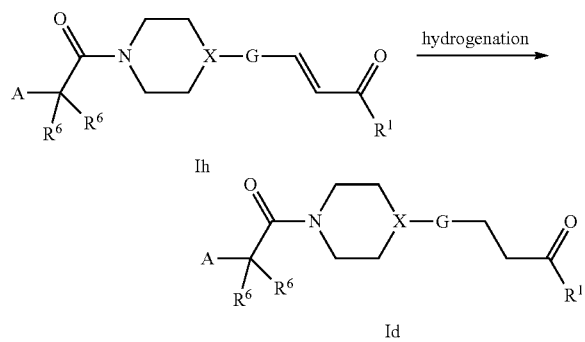

One way of preparing compounds of the formula (Id) from corresponding compounds (Ih) is shown in Scheme 35.

The same process as already described in Scheme 9 (process I) is employed.

The invention furthermore provides the non-medicinal use of the ketoheteroarylpiperidine and -piperazine derivatives for controlling unwanted microorganisms.

The present invention furthermore relates to a crop protection composition for controlling unwanted fungi, which composition comprises at least one of the ketoheteroarylpiperidine and -piperazine derivatives of the formula (I). These are preferably fungicidal compositions which comprise agriculturally suitable auxiliaries, solvents, carriers, surfactants or extenders.

Moreover, the invention relates to a method for controlling unwanted microorganisms, characterized in that ketoheteroarylpiperidine and -piperazine derivatives of the formula (I) according to the invention are applied to the phytopathogenic fungi and/or their habitat.

According to the invention, a carrier is a natural or synthetic organic or inorganic substance with which the active compounds are mixed or bonded for better applicability, in particular for application to plants or plant parts or seed. The carrier, which may be solid or liquid, is generally inert and should be suitable for use in agriculture.

Suitable solid or liquid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral and vegetable oils and derivatives of these. Mixtures of such carriers may also be used. Suitable solid carriers for granules are: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Suitable liquefied gaseous extenders or carriers are liquids which are gaseous at ambient temperature and under atmospheric pressure, for example aerosol propellants, such as halogenated hydrocarbons, and also butane, propane, nitrogen and carbon dioxide.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins and synthetic phospholipids can be used in the formulations. Other possible additives are mineral and vegetable oils.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The compositions according to the invention may comprise additional further components, such as, for example, surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

The formulations generally comprise between 0.05 and 99% by weight, 0.01 and 98% by weight, preferably between 0.1 and 95% by weight, particularly preferably between 0.5 and 90% of active compound, very particularly preferably between 10 and 70% by weight.

The active compounds or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide-coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV cold-fogging and warm-fogging formulations.

The formulations mentioned can be prepared in a manner known per se, for example by mixing the active compounds with at least one customary extender, solvent or diluent, emulsifier, dispersant, and/or binder or fixative, wetting agent, water repellent, if appropriate desiccants and UV stabilizers and, if appropriate, dyes and pigments, defoamers, preservatives, secondary thickeners, adhesives, gibberellins and also further processing auxiliaries.

The compositions according to the invention include not only formulations which are already ready for use and can be applied with a suitable apparatus to the plant or the seed, but also commercial concentrates which have to be diluted with water prior to use.

The active compounds according to the invention can be present as such or in their (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

The invention furthermore includes a method for treating seed.

The invention furthermore relates to seed which has been treated in accordance with one of the methods described in the previous paragraph. The seeds according to the invention are used in methods for the protection of seed from undesirable fungi. In these methods, seed treated with at least one active compound according to the invention is employed.

The active compounds or compositions according to the invention are also suitable for treating seed. A large part of the damage to crop plants caused by harmful organisms is triggered by the infection of the seed during storage or after sowing both during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of crop protection agents after sowing or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore also relates to a method for the protection of seed and germinating plants, from attack by phytopathogenic fungi, by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection agents. Owing to the concerns regarding a possible impact of the crop protection agents on the environment and the health of humans and animals, there are efforts to reduce the amount of active compounds applied.

One of the advantages of the present invention is that the particular systemic properties of the active compounds and compositions according to the invention mean that treatment of the seed with these active compounds and compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the active compounds or compositions according to the invention can be used in particular also for transgenic seed where the plant growing from this seed is capable of expressing a protein which acts against pests. By treating such seed with the active compounds or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety which is employed in agriculture, in the greenhouse, in forests or in horticulture and viticulture. In particular, this takes the form of seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cacao, sugar cane, tobacco, vegetables (such as tomato, cucumbers, onions and lettuce), turf and ornamentals (see also hereinbelow). The treatment of the seed of cereals (such as wheat, barley, rye, triticale and oats), maize and rice is of particular importance.

As also described further below, the treatment of transgenic seed with the active compounds or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus*, *Rhizobium*, *Pseudomonas*, *Serratia*, *Trichoderma*, *Clavibacter*, *Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

Within the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272, 417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples which may be mentioned are the colorants known by the names Rhodamin B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of crop protection agents and pesticides], vol. 2, Springer Verlag, 1970, p. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The active compounds or compositions according to the invention have a potent fungicidal activity and can be employed for controlling undesirable fungi in crop protection and in the protection of materials.

The ketoheteroarylpiperidine and -piperazine derivatives according to the invention can be employed in crop protection for controlling Plasmodiophoromycetes, Oomycetes, Chytridiomycetes, Zygomycetes, Ascomycetes, Basidiomycetes and Deuteromycetes.

The fungicidal compositions according to the invention can be used for the curative or protective control of phytopathogenic fungi. Accordingly, the invention also relates to curative and protective methods for controlling phytopathogenic fungi using the active compounds or compositions according to the invention, which are applied to the seed, the plant or plant parts, the fruit or the soil in which the plants grow.

The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

The fact that the active compounds are well tolerated by plants at the concentrations required for controlling plant diseases permits the treatment of above-ground parts of plants, of propagation stock and seeds, and of the soil.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. Parts of plants also include harvested crops and vegetative and generative propagation material, for example seedlings, tubers, rhizomes, cuttings and seeds.

The active compounds according to the invention are suitable for the protection of plants and plant organs, for increasing the harvest yields, for improving the quality of the harvested crop, while being well tolerated by plants, having favourable toxicity to warm-blooded species and being environmentally friendly. They may be preferably employed as crop protection agents. They are active against normally sensitive and resistant species and also against all or some stages of development.

The following plants may be mentioned as plants which can be treated according to the invention: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leeks, onions), *Papilionaceae* sp. (for example peas); major crop plants such as *Gramineae* sp. (for example maize, turf, cereals such as wheat, rye, rice, barley, oats, millet and triticale), *Poaceae* sp. (for example sugar cane), *Asteraceae* sp. (for example sunflower), *Brassicaceae* sp. (for example white cabbage, red cabbage, broccoli, cauliflower, Brussels sprouts, pak Choi, kohlrabi, small radishes, and also oilseed rape, mustard, horseradish and cress), *Fabacae* sp. (for example beans, peanuts), *Papilionaceae* sp. (for example soya beans), *Solanaceae* sp. (for example potatoes), *Chenopodiaceae* sp. (for example sugar beet, fodder beet, Swiss chard, beetroot); useful plants and ornamental plants in gardens and forests; and in each case genetically modified types of these plants.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Possible are thus, for example, the following effects which exceed the effects which were actually to be expected: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products.

At certain application rates, the active compound combinations according to the invention may also have a strengthening effect in plants. Accordingly, they are suitable for mobilizing the defense system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defense system of plants in such a way that, when subsequently inoculated with unwanted phytopathogenic fungi, the treated plants display a substantial degree of resistance to these unwanted phytopathogenic fungi. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stress factors, i.e. said plants have a better defense against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid effect, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio)benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:

1) an insecticidal crystal protein from *Bacillus thuringiensis* or an insecticidal portion thereof, such as the insecticidal crystal proteins listed online at: lifesci.sussex.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or 2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or 3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or 4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604;

5) an insecticidal secreted protein from *Bacillus thuringiensis* or *Bacillus cereus*, or an insecticidal portion thereof, such as the vegetative insecticidal proteins (VIP) listed at: lifesci.sussex.ac.uk/home/Neil_Crickmore/Bt/vip.html, for example proteins from the VIP3Aa protein class; or 6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;

7) a hybrid insecticidal protein comprising parts from different secreted proteins from *Bacillus thuringiensis* or *Bacillus cereus*, such as a hybrid of the proteins in 1) above or a hybrid of the proteins in 2) above; or 8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:
1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.
3) Transgenic plants which produce hyaluronan.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:
a) plants, such as cotton plants, which contain an altered form of cellulose synthase genes;
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the base of the fibre cell is altered, for example through downregulation of fibre-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:
a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated according to the invention are plants which comprise one or more genes which encode one or more toxins and are the transgenic plants available under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize) Herbicide-resistant plants (plants bred in a conventional manner for herbicide tolerance) which may be mentioned include the varieties sold under the name Clearfield® (for example maize).

Particularly useful transgenic plants which may be treated according to the invention are plants containing transformation events, or a combination of transformation events, and that are listed for example in the databases for various national or regional regulatory agencies (see for example gmoinfo.jrc.it/gmp_browse.aspx and agbios.com/dbase.php).

Moreover, in the protection of materials, the active compounds or compositions according to the invention can be employed for protecting industrial materials against attack and destruction by unwanted microorganisms, such as, for example, fungi.

Industrial materials in the present context are understood as meaning non-living materials which have been prepared for use in industry. For example, industrial materials which are intended to be protected by active compounds according to the invention from fungal change or destruction can be adhesives, sizes, paper, wallpaper, and board, textiles, carpets, leather, wood, paints and plastic articles, cooling lubricants and other materials which can be infected with, or destroyed by, microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood. The active compounds or compositions according to the invention may prevent disadvantageous effects, such as rotting, decay, discoloration, decoloration or formation of mould. Moreover, the compounds according to the invention can be employed for protecting objects which come into contact with saltwater or brackish water, in particular hulls, screens, nets, buildings, moorings and signalling systems, against fouling.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The active compounds according to the invention may prevent disadvantageous effects, such as rotting, decay, discoloration, decoloration or formation of mould.

Some pathogens of fungal diseases which can be treated according to the invention may be mentioned by way of example, but not by way of limitation:

diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

diseases caused by pathogens from the group of the Oomycetes, such as, for example, *Bremia* species, such as, for example, *Bremia lactucae*; *Peronospora* species, such as, for example, *Peronospora pisi* or *P. brassicae*; *Phytophthora* species, such as, for example, *Phytophthora infestans*; *Plasmopara* species, such as, for example, *Plasmopara viticola*; *Pseudoperonospora* species, such as, for example, *Pseudoperonospora humuli* or *Pseudoperonospora cubensis*; *Pythium* species, such as, for example, *Pythium ultimum*;

leaf blotch diseases and leaf wilt diseases caused, for example, by *Alternaria* species, such as, for example, *Alternaria solani*; *Cercospora* species, such as, for example, *Cercospora beticola*; *Cladiosporium* species, such as, for example, *Cladiosporium cucumerinum*; *Cochliobolus* species, such as, for example, *Cochliobolus sativus* (conidia form: *Drechslera*, syn: *Helminthosporium*); *Colletotrichum* species, such as, for example, *Colletotrichum lindemuthanium*; *Cycloconium* species, such as, for example, *Cycloconium oleaginum*; *Diaporthe* species, such as, for example, *Diaporthe citri*; *Elsinoe* species, such as, for example, *Elsinoe fawcettii*; *Gloeosporium* species, such as, for example, *Gloeosporium laeticolor*; *Glomerella* species, such as, for example, *Glomerella cingulata*; *Guignardia* species, such as, for example, *Guignardia bidwelli*; *Leptosphaeria* species, such as, for example, *Leptosphaeria maculans*; *Magnaporthe* species, such as, for example, *Magnaporthe grisea*; *Microdochium* species, such as, for example, *Microdochium nivale*; *Mycosphaerella* species, such as, for example, *Mycosphaerella graminicola* and *M. fijiensis*; *Phaeosphaeria* species, such as, for example, *Phaeosphaeria nodorum*; *Pyrenophora* species, such as, for example, *Pyrenophora teres*; *Ramularia* species, such as, for example, *Ramularia collo-cygni*; *Rhynchosporium* species, such as, for example, *Rhynchosporium secalis*; *Septoria* species, such as, for example, *Septoria apii*; *Typhula* species, such as, for example, *Typhula incarnata*; *Venturia* species, such as, for example, *Venturia inaequalis*;

root and stem diseases caused, for example, by *Corticium* species, such as, for example, *Corticium graminearum*; *Fusarium* species, such as, for example, *Fusarium oxysporum*; *Gaeumannomyces* species, such as, for example, *Gaeumannomyces graminis*; *Rhizoctonia* species, such as, for example *Rhizoctonia solani*; *Tapesia* species, such as, for example, *Tapesia acuformis*; *Thielaviopsis* species, such as, for example, *Thielaviopsis basicola*;

ear and panicle diseases (including corn cobs) caused, for example, by *Alternaria* species, such as, for example, *Alternaria* spp.; *Aspergillus* species, such as, for example, *Aspergillus flavus*; *Cladosporium* species, such as, for example, *Cladosporium cladosporioides*; *Claviceps* species, such as, for example, *Claviceps purpurea*; *Fusarium* species, such as, for example, *Fusarium culmorum*; *Gibberella* species, such as, for example, *Gibberella zeae*; *Monographella* species, such as, for example, *Monographella nivalis*; *Septoria* species, such as, for example, *Septoria nodorum*;

diseases caused by smut fungi, such as, for example, *Sphacelotheca* species, such as, for example, *Sphacelotheca reiliana*; *Tilletia* species, such as, for example, *Tilletia caries*, *T. controversa*; *Urocystis* species, such as, for example, *Urocystis occulta*; *Ustilago* species, such as, for example, *Ustilago nuda*, *U. nuda tritici*;

fruit rot caused, for example, by *Aspergillus* species, such as, for example, *Aspergillus flavus*; *Botrytis* species, such as, for example, *Botrytis cinerea*; *Penicillium* species, such as, for example, *Penicillium expansum* and *P. purpurogenum*; *Sclerotinia* species, such as, for example, *Sclerotinia sclerotiorum*;

*Verticilium* species, such as, for example, *Verticilium alboatrum*;

seed- and soil-borne rot and wilt diseases, and also diseases of seedlings, caused, for example, by *Fusarium* species, such as, for example, *Fusarium culmorum*; *Phytophthora* species, such as, for example, *Phytophthora cactorum*; *Pythium* species, such as, for example, *Pythium ultimum*; *Rhizoctonia* species, such as, for example, *Rhizoctonia solani*; *Sclerotium* species, such as, for example, *Sclerotium rolfsii*;

cancerous diseases, galls and witches' broom caused, for example, by *Nectria* species, such as, for example, *Nectria galligena*;

wilt diseases caused, for example, by *Monilinia* species, such as, for example, *Monilinia laxa*;

deformations of leaves, flowers and fruits caused, for example, by *Taphrina* species, such as, for example, *Taphrina deformans*;

degenerative diseases of woody plants caused, for example, by *Esca* species, such as, for example, *Phaeomoniella chlamydospora* and *Phaeoacremonium aleophilum* and *Fomitiporia mediterranea*;

diseases of flowers and seeds caused, for example, by *Botrytis* species, such as, for example, *Botrytis cinerea*;

diseases of plant tubers caused, for example, by *Rhizoctonia* species, such as, for example, *Rhizoctonia solani*; *Helminthosporium* species, such as, for example, *Helminthosporium solani*;

diseases caused by bacterial pathogens, such as, for example, *Xanthomonas* species, such as, for example, *Xanthomonas campestris* pv. *oryzae*; *Pseudomonas* species, such as, for example, *Pseudomonas syringae* pv. *lachrymans*; *Erwinia* species, such as, for example, *Erwinia amylovora*.

Preference is given to controlling the following diseases of soya beans:

Fungal diseases on leaves, stems, pods and seeds caused, for example, by *alternaria* leaf spot (*Alternaria* spec. *atrans tenuissima*), anthracnose (*Colletotrichum gloeosporoides dematium* var. *truncatum*), brown spot (*Septoria glycines*), *cercospora* leaf spot and blight (*Cercospora kikuchii*, *choanephora* leaf blight (*Choanephora infundibulifera trispora* (Syn.)), *dactuliophora* leaf spot (*Dactuliophora glycines*), downy mildew (*Peronospora manshurica*), *drechslera* blight (*Drechslera glycini*), frogeye leaf spot (*Cercospora sojina*), *leptosphaerulina* leaf spot (*Leptosphaerulina trifolii*), *phyllostica* leaf spot (*Phyllosticta sojaecola*), pod and stem blight (*Phomopsis sojae*), powdery mildew (*Microsphaera diffusa*), *pyrenochaeta* leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), *fusarium* blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), *neocosmospora* (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Organisms which can bring about degradation or modification of the industrial materials and which may be mentioned are fungi. The active compounds according to the invention preferably act against fungi, in particular moulds, wood-discoloring and wood-destroying fungi (Basidiomycetes). Fungi of the following genera may be mentioned as examples: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride*.

In addition, the active compounds according to the invention also have very good antimycotic activity. They have a very broad antimycotic activity spectrum, in particular against dermatophytes and yeasts, moulds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

When using the active compounds according to the invention as fungicides, the application rates can be varied within a relatively wide range, depending on the kind of application. The application rate of the active compounds according to the invention is when treating plant parts, for example leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used);

when treating seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed;

when treating the soil: from 0.1 to 10 000 g/ha, preferably from 1 to 5000 g/ha.

These application rates are mentioned only by way of example and are not limiting in the sense of the invention.

The active compounds or compositions according to the invention can thus be employed for protecting plants for a certain period of time after treatment against attack by the pathogens mentioned. The period for which protection is provided extends generally for 1 to 28 days, preferably for 1 to 14 days, particularly preferably for 1 to 10 days, very particularly preferably for 1 to 7 days after the treatment of the plants with the active compounds, or for up to 200 days after a seed treatment.

In addition, by the treatment according to the invention it is possible to reduce the mycotoxin content in the harvested material and the foodstuffs and feedstuffs prepared therefrom. Particular, but not exclusive, mention may be made here of the following mycotoxins: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaproliferin, fusarenol, ochratoxins, patulin, ergot alkaloids and aflatoxins produced, for example, by the following fungi: *Fusarium* spec., such as *Fusarium acuminatum, F. avenaceum, F. crookwellense, F. culmorum, F. graminearum (Gibberella zeae), F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

The plants listed can be treated according to the invention in a particularly advantageous manner with the ketoheteroarylpiperidine and -piperazine derivatives of the formula (I) or the compositions according to the invention. The preferred ranges stated above for the active compounds or compositions also apply to the treatment of these plants. Particular emphasis is given to the treatment of plants with the compounds or compositions specifically mentioned in the present text.

The preparation and the use of the active compounds of the formula (I) according to the invention is illustrated by the examples below. However, the invention is not limited to these examples.

General note: Unless indicated otherwise, all chromatographic purification and separation steps are carried out on silica gel and using a solvent gradient of from 0:100 ethyl acetate/cyclohexane to 100:0 ethyl acetate/cyclohexane.

EXAMPLES

Preparation of (I-24)

Step 1 tert-Butyl 4-{4-[methoxy(methyl)carbamoyl]-1,3-thiazol-2-yl}piperidine-1-carboxylate (V-1)

At room temperature, triethylamine (324 mg) was added to a suspension of 2-[1-(tert-butoxycarbonyl)piperidin-4-yl]-1, 3-thiazole-4-carboxylic acid (1.0 g) in dichloromethane (30 mL). After ten minutes of stirring, methoxy(methyl)ammonium chloride (312 mg), 4-dimethylaminopyridine (39 mg) and 1-ethyl-3-(3'-dimethylaminopropyl)carbodiimide HCl salt (675 mg) were added. The mixture was stirred at room temperature overnight, and water was then added. The aqueous phase was separated off and extracted with ethyl acetate. The combined organic phases are dried over sodium sulphate and concentrated under reduced pressure. The residue was purified chromatographically. This gave tert-butyl 4-{4-[methoxy(methyl)carbamoyl]-1,3-thiazol-2-yl}piperidine-1-carboxylate (1.0 g).

log P (pH2.7): 2.40

$^1$H NMR (DMSO-d$_6$, 400 MHz): $\delta_{ppm}$: 1.41 (s, 9H), 1.52-1.63 (m, 2H), 2.02-2.08 (m, 2H), 2.90 (bs, 2H), 3.19-3.30 (1H), 3.29 (s, 3H), 3.32 (s, 3H), 3.96-4.04 (m, 2H), 8.09 (s, 1H)

MS (ESI): 356 ([M+H]$^+$)

Step 2 tert-Butyl 4-[4-(cyclohexylacetyl)-1,3-thiazol-2-yl]piperidine-1-carboxylate (IV-1)

Under argon and at −78° C., cyclohexylmethylmagnesium chloride 0.5M in diethyl ether (2.7 ml) was added dropwise to a solution of tert-butyl 4-{4-[methoxy(methyl)carbamoyl]-1,3-thiazol-2-yl}piperidine-1-carboxylate (480 mg) in tetrahydrofuran (5 ml). The reaction mixture was stirred at −78° C. for one hour. The reaction mixture was then stirred at room temperature for one hour. Saturated ammonium chloride solution was then added to the reaction mixture, and the aqueous phase was separated off. After extraction of the aqueous phase with ethyl acetate, the combined organic phases were dried over sodium sulphate and the solvent was removed under reduced pressure. This gave tert-butyl 4-[4-(cyclohexylacetyl)-1,3-thiazol-2-yl]piperidine-1-carboxylate (335 mg).

log P (pH2.7): 5.43

$^1$H NMR (DMSO-d$_6$, 400 MHz): $\delta_{ppm}$: 0.98-1.05 (m, 2H), 1.14-1.22 (m, 1H), 1.22-1.31 (m, 2H), 1.44 (s, 9H), 1.61-1.76 (m, 8H), 2.05-2.10 (m, 2H). 2.87 (d, 2H), 2.90 (bs, 2H), 3.18-3.26 (m, 1H), 4.07-4.15 (m, 2H), 8.10 (s, 1H)

MS (ESI): 337 ([M-(CH$_3$)$_3$C+H]$^+$)

Step 3

4-[4-(Cyclohexylacetyl)-1,3-thiazol-2-yl]piperidinium chloride (II-1)

Under argon and at 0° C., a solution of hydrogen chloride in dioxane (4M, 1 ml) was added to a solution of tert-butyl 4-[4-(cyclohexylacetyl)-1,3-thiazol-2-yl]piperidine-1-carboxylate (5.0 g) in diethyl ether (1 ml). The mixture was stirred at 0° C. and then slowly warmed to room temperature. After stirring overnight, excess acid and the solvent were removed under reduced pressure. This gave 4-[4-(cyclohexylacetyl)-1,3-thiazol-2-yl]piperidinium chloride (315 mg).

log P (pH2.7): 1.35

MS (ESI): 293 ([M-Cl]$^+$)

Step 4

2-[3,5-Bis(difluoromethyl)-1H-pyrazol-1-yl]-1-{4-[4-(cyclohexylacetyl)-1,3-thiazol-2-yl]piperidin-1-yl}ethanone (I-24)

Oxalyl chloride (116 mg) and a drop of N,N-dimethylformamide were added to a solution of [3,5-(difluoromethyl)-1H-pyrazol-1-yl]acetic acid (69 mg) in dichloromethane (5 ml). The reaction mixture was then stirred for 30 minutes. Excess oxalyl chloride was then removed under reduced pressure, and the residue was redissolved in dichloromethane (2 ml). The solution was then added to a solution of 4-[4-(cyclohexylacetyl)-1,3-thiazol-2-yl]piperidinium chloride (100 mg) in dichloromethane (5 ml) and triethylamine (92 mg). The reaction mixture was stirred for 30 minutes. Solvent and triethylamine were removed under reduced pressure. Purification of the residue by column chromatography gave 2-[3,5-bis(difluoromethyl)-1H-pyrazol-1-yl]-1-{4-[4-(cyclohexylacetyl)-1,3-thiazol-2-yl]piperidin-1-yl}ethanone (105 mg).

log P (pH2.7): 4.02

$^1$H NMR (DMSO-d$_6$, 400 MHz): $\delta_{ppm}$: 0.95-1.02 (m, 2H), 1.10-1.26 (m, 3H), 1.54-1.69 (m, 6H), 1.77-1.91 (m, 2H), 2.06-2.15 (m, 2H), 2.82-2.87 (m, 1H), 2.89 (d, 2H), 3.25-3.30 (m, 1H), 3.35-3.41 (m, 1H), 3.94-3.99 (m, 1H), 4.33-4.37 (m, 1H), 5.36 (d, 1H), 5.45 (d, 1H), 6.91 (s, 1H), 7.04 (t, 1H), 7.18 (t, 1H), 8.44 (s, 1H)

MS (ESI): 501 ([M+H]$^+$)

Preparation of Compound (I-25)

Step 1

N-(5-Chloro-2-methylphenyl)-4-[4-(cyclohexylacetyl)-1,3-thiazol-2-yl]piperidine-1-carboxamide (I-25)

Triethylamine (0.047 ml) was added to a mixture of 4-[4-(cyclohexylacetyl)-1,3-thiazol-2-yl]piperidinium chloride (100 mg) in dichloromethane (1 ml). After the solid had dissolved completely, 4-chloro-2-isocyanato-1-methylbenzene (51 mg) and a drop of 1,8-diazabicyclo[5.4.0]undec-7-ene were added. The reaction mixture was then stirred for 5 minutes. Solvent and triethylamine were removed under reduced pressure. Purification of the residue by column chromatography gave N-(5-chloro-2-methylphenyl)-4-[4-(cyclohexylacetyl)-1,3-thiazol-2-yl]piperidine-1-carboxamide (128 mg).

log P (pH2.7): 4.51

$^1$H NMR (DMSO-d$_6$, 400 MHz): $\delta_{ppm}$: 0.94-1.05 (m, 2H), 1.10-1.26 (m, 4H), 1.56-1.73 (m, 6H), 1.83-1.92 (m, 1H), 2.06-2.13 (m, 2H), 2.16 (s, 3H), 2.88 (d, 2H), 2.98-3.06 (m, 2H), 3.30-3.38 (m, 1H), 4.11-4.18 (m, 2H), 7.07 (dd, 1H), 7.19 (d, 1H), 7.33 (d, 1H), 8.12 (s, 1H), 8.04 (s, 1H)

MS (ESI): 460 ([M+H]$^+$)

Preparation of Compound (I-58)

Step 1

1-[2-(1-{2-[3,5-Bis(difluoromethyl)-1H-pyrazol-1-yl]ethanethioyl}piperidin-4-yl)-1,3-thiazol-4-yl]-2-cyclohexylethanone (I-58)

At room temperature, 2,4-bis(4-methoxyphenyl)-1,3,2,4-dithiadiphosphetane 2,4-disulfide (194 mg) was added to a solution of 2-[3,5-bis(difluoromethyl)-1H-pyrazol-1-yl]-1-{4-[4-(cyclohexylacetyl)-1,3-thiazol-2-yl]piperidin-1-yl}ethanone (200 mg) in toluene (2 ml). The reaction mixture was stirred at 60° C. for 2 hours. After removal of the solvent under reduced pressure, the residue was purified chromatographically. This gave 1-[2-(1-{2-[3,5-bis(difluoromethyl)-1H-pyrazol-1-yl]ethanethioyl}-piperidin-4-yl)-1,3-thiazol-4-yl]-2-cyclohexylethanone (101 mg, 49%).

log P (pH2.7): 4.63

1H NMR (DMSO-d$_6$, 400 MHz): δ$_{ppm}$: 0.94-1.05 (m, 2H), 1.10-1.30 (m, 4H), 1.56-1.80 (m, 6H), 1.83-1.95 (m, 1H), 2.06-2.15 (m, 2H), 2.88 (d, 2H), 3.30-3.42 (m, 1H), 3.51-3.61 (m, 2H), 4.42-4.49 (m, 1H), 5.26-5.33 (m, 1H), 5.55 (d, 1H), 5.59 (d, 1H), 6.89 (s, 1H), 7.02 (t, 1H), 7.20 (t, 1H), 8.04 (s, 1H)

MS (ESI): 517 ([M+H]$^+$)

Preparation of Compound (I-60)

Step 1 tert-Butyl 4-[4-(2-cyclohexyl-N-methoxyethanimidoyl)-1,3-thiazol-2-yl]piperidine-1-carboxylate At room temperature, methoxyammonium chloride (171 mg) was added to a solution of tert-butyl 4-{4-[methoxy(methyl)carbamoyl]-1,3-thiazol-2-yl}piperidine-1-carboxylate (403 mg) in ethanol (2 ml). The reaction mixture was stirred at 50° C. for 24 hours, and water was then added. The aqueous phase was separated off and extracted with ethyl acetate. The combined organic phases were dried over sodium sulphate and concentrated under reduced pressure. The residue was purified chromatographically. This gave tert-butyl 4-[4-(2-cyclohexyl-N-methoxyethanimidoyl)-1,3-thiazol-2-yl]piperidine-1-carboxylate (361 mg).

Step 2

2-[3,5-Bis(difluoromethyl)-1H-pyrazol-1-yl]-1-{4-[4-(2-cyclohexyl-N-methoxyethanimidoyl)-1,3-thiazol-2-yl]piperidin-1-yl}ethanone (I-60)

Under argon and at 0° C., a solution of hydrogen chloride in dioxane (4M, 2.6 ml) was added to a suspension of tert-butyl 4-[4-(2-cyclohexyl-N-methoxyethanimidoyl)-1,3-thiazol-2-yl]piperidine-1-carboxylate (287 mg). The mixture was stirred at 0° C. and then slowly warmed to room temperature. After stirring overnight, excess acid and the solvent were removed under reduced pressure. This gave 4-[4-(2-cyclohexyl-N-methoxyethanimidoyl)-1,3-thiazol-2-yl]piperidinium chloride.

At room temperature, [3,5-(difluoromethyl)-1H-pyrazol-1-yl]acetic acid (225 mg), dimethylaminopyridine (12 mg) and 1-ethyl-3-(3'-dimethylaminopropyl)carbodiimide (89 mg) were added to a solution of 4-[4-(2-cyclohexyl-N-methoxyethanimidoyl)-1,3-thiazol-2-yl]piperidinium chloride (357 mg) in dichloromethane (3 ml) and triethylamine (101 mg). The mixture was stirred for 3 hours, and water was then added. The aqueous phase was removed and extracted with ethyl acetate. The combined organic phases were dried with sodium sulphate. The solid was filtered off and the solvent was distilled off. The residue was purified chromatographically. This gave 2-[3,5-bis(difluoromethyl)-1H-pyrazol-1-yl]-1-{4-[4-(2-cyclohexyl-N-methoxyethanimidoyl)-1,3-thiazol-2-yl]piperidin-1-yl}ethanone (182 mg, 70%).

log P (pH2.7): 4.80
MS (ESI): 530 ([M+H]$^+$)

Preparation of Compound (I-14)

Step 1 tert-Butyl 4-[4-(1-hydroxy-3-phenylpropyl)-1,3-thiazol-2-yl]piperidine-1-carboxylate (XVI-1)

Under an argon atmosphere and at −78° C., chloro(2-phenylethyl)magnesium (1M in diethyl ether, 3.77 ml) was added dropwise to a solution of tert-butyl 4-(4-formyl-1,3-thiazol-2-yl)piperidine-1-carboxylate (1.0 g) in tetrahydrofuran (10 ml). The reaction mixture was stirred at −78° C. for one hour, and more chloro(2-phenylethyl)magnesium (3M in diethyl ether, 0.20 ml) was then added dropwise. The reaction mixture was then stirred for 20 minutes. Saturated ammonium chloride solution was then added to the reaction mixture, and the aqueous phase was separated off. After extraction of the aqueous phase with ethyl acetate, the combined organic phases were dried over sodium sulphate and the solvent was removed under reduced pressure. This gave tert-butyl 4-[4-(1-hydroxy-3-phenylpropyl)-1,3-thiazol-2-yl]piperidine-1-carboxylate (790 mg).

log P (pH2.7): 3.79
$^1$H NMR (DMSO-d$_6$, 400 MHz): δ$_{ppm}$: 1.41 (s, 9H), 1.48-1.61 (m, 2H), 1.90-2.11 (4H), 2.62-2.67 (m, 2H), 2.87-2.95 (m, 2H), 3.15-3.20 (m, 1H), 3.94-4.00 (2H), 4.62-4.67 (m, 1H), 5.09-5.12 (m, 1H), 7.11-7.18 (m, 3H), 7.22-7.27 (m, 3H)
MS (ESI): 347 ([M-C(CH$_3$)$_3$+2H]$^+$)

Step 2 tert-Butyl 4-[4-(3-phenylpropanoyl)-1,3-thiazol-2-yl]piperidine-1-carboxylate (IV-2)

At room temperature, 1,1,1-triacetoxy-1,1-dihydro-1,2-benziodoxol-3(1H)-one (15% strength solution in dichloromethane, 8.3 g) was added dropwise to a solution of tert-butyl 4-[4-(1-hydroxy-3-phenylpropyl)-1,3-thiazol-2-yl]piperidine-1-carboxylate (790 mg) in dichloromethane (7.9 ml). The reaction mixture was stirred at room temperature overnight. 5 g of silica gel were then added, and the solvent was removed under reduced pressure. The residue was purified chromatographically. This gave tert-butyl 4-[4-(3-phenylpropanoyl)-1,3-thiazol-2-yl]piperidine-1-carboxylate (545 mg).

log P (pH2.7): 4.54
$^1$H NMR (DMSO-d$_6$, 400 MHz): δ$_{ppm}$: 1.41 (s, 9H), 1.54-1.65 (m, 2H), 2.00-2.08 (m, 2H), 2.88-2.97 (m, 4H), 3.20-3.30 (m, 1H), 3.31 (t, 2H), 3.96-4.02 (m, 2H), 7.12-7.18 (m, 1H), 7.21-7.28 (m, 4H), 8.35 (s, 1H)
MS (ESI): 345 ([M-C(CH$_3$)$_3$+2H]$^+$)

Step 3

4-[4-(3-Phenylpropanoyl)-1,3-thiazol-2-yl]piperidinium chloride (II-2)

tert-Butyl 4-[4-(3-phenylpropanoyl)-1,3-thiazol-2-yl]piperidine-1-carboxylate (550 mg) was reacted analogously to II-1 (step 3) with hydrogen chloride in diethyl ether (2M, 11 ml). This gave 4-[4-(3-phenylpropanoyl)-1,3-thiazol-2-yl]piperidinium chloride (500 mg).

log P (pH2.7): 1.19
$^1$H NMR (DMSO-d$_6$, 400 MHz): δ$_{ppm}$: 1.95-2.05 (m, 2H), 2.18-2.25 (m, 2H), 2.96 (t, 2H), 3.00-3.08 (m, 2H), 3.29-3.36 (m, 4H), 3.36-3.46 (m, 1H), 7.13-7.18 (m, 1H), 7.22-7.30 (m, 4H), 8.40 (s, 1H), 8.99 (bs, 1H), 9.22 (bs, 1H)
MS (ESI): 301 ([M-Cl]$^+$)

Step 4

1-[2-(1-{[5-Methyl-3-(trifluoromethyl)-1H-pyrazol-1-yl]acetyl}piperidin-4-yl)-1,3-thiazol-4-yl]-3-phenylpropan-1-one 4-[4-(3-Phenylpropanoyl)-1,3-thiazol-2-yl]piperidinium chloride (502 mg) was reacted analogously to I-24 (step 4)

with [5-methyl-3-(trifluoromethyl)-1H-pyrazol-1-yl]acetic acid (310 mg). This gave 1-[2-(1-{[5-methyl-3-(trifluoromethyl)-1H-pyrazol-1-yl]acetyl}piperidin-4-yl)-1,3-thiazol-4-yl]-3-phenylpropan-1-one (495 mg).

log P (pH2.7): 3.64

$^1$H NMR (DMSO-d$_6$, 400 MHz): $\delta_{ppm}$: 1.65 (bs, 1H), 1.80 (bs, 1H), 2.08-2.17 (m, 2H), 2.22 (s, 3H), 2.90 (bs, 1H), 2.96 (t, 2H), 3.20-3.42 (m, 2H), 3.33 (t, 2H), 3.99 (bs, 1H), 4.33 (bs, 1H), 5.15-5.25 (m, 2H), 6.44 (s, 1H), 7.14-7.18 (m, 1H), 7.21-7.30 (m, 4H), 8.37 (s, 1H)

MS (ESI): 491 ([M+H]$^+$)

Preparation of Compound (I-12)

Step 1

1-[2-(Piperidin-4-yl)-1,3-thiazol-4-yl]ethanone hydrochloride

Under an argon atmosphere and at 0° C., hydrochloric acid (2 M in diethyl ether, 23 ml) was added dropwise to a solution of tert-butyl 4-(4-acetyl-1,3-thiazol-2-yl)piperidine-1-carboxylate (920 mg) in diethyl ether (2 ml). The reaction mixture was stirred for 24 hours. Solvent and excess acid were removed under reduced pressure. This gave 1-[2-(piperidin-4-yl)-1,3-thiazol-4-yl]ethanone hydrochloride (1.05 g) as a white highly hygroscopic solid which was immediately processed further.

$^1$H NMR (DMSO-d$_6$, 400 MHz): $\delta_{ppm}$: 2.01 (qd, 2H), 2.28-2.20 (m, 2H), 2.55 (s, 3H), 3.02 (q, 2H), 3.38-3.27 (m, 2H), 3.42 (m, 1H), 8.39 (s, 1H), 9.06 (bs, 1H), 9.25 (bs, 1H)

MS (ESI): 211 ([M+H−Cl]$^+$)

Step 2

1-[4-(4-Acetyl-1,3-thiazol-2-yl)piperidin-1-yl]-2-[5-methyl-3-(trifluoromethyl)-1H-pyrazol-1-yl]ethanone (XXII-1)

Oxalyl chloride (1.74 g) and a drop of N,N-dimethylformamide were added to a solution of [5-methyl-3-(trifluoromethyl)-1H-pyrazol-1-yl]acetic acid (1.00 g) in dichloromethane (10 ml). The reaction mixture was then stirred for 24 hours. Excess oxalyl chloride was then removed under reduced pressure, and the residue was redissolved in dichloromethane (10 ml). With cooling on an ice bath, the solution was then added to a suspension of 1-[2-(piperidin-4-yl)-1,3-thiazol-4-yl]ethanone hydrochloride (1.13 g) in dichloromethane (10 ml) and N,N-diisopropylethylamine (1.77 g). The reaction mixture was then allowed to warm to room temperature and stirred for another 2 hours. Saturated aqueous ammonium chloride solution (5 ml) was then added to the reaction mixture. The aqueous phase was separated off and extracted with dichloromethane. All organic phases were combined and dried with anhydrous sodium sulphate. The solid was then filtered off and the solvent was removed under reduced pressure. Purification by column chromatography (silica gel, ethyl acetate:hexane 0%-100% elution gradient) gave 1-[4-(4-acetyl-1,3-thiazol-2-yl)piperidin-1-yl]-2-[5-methyl-3-(trifluoromethyl)-1H-pyrazol-1-yl]ethanone (1.00 g).

log P (pH2.7): 2.25

$^1$H NMR (DMSO-d$_6$, 400 MHz): $\delta_{ppm}$: 1.65 (bs, 1H), 1.80 (bs, 1H), 2.18-2.11 (m, 2H), 2.23 (s, 3H), 2.55 (s, 3H), 2.90 (bs, 1H), 3.28 (bs, 1H), 3.39 (m, 1H), 4.00 (bs, 1H), 4.33 (bs, 1H), 5.22 (bs, 2H), 6.45 (s, 1H), 8.36 (s, 1H)

MS (ESI): 401 ([M+H]$^+$)

Step 3

(2E)-3-(2,6-Difluorophenyl)-1-[2-(1-{[5-methyl-3-(trifluoromethyl)-1H-pyrazol-1-yl]acetyl}piperidin-4-yl)-1,3-thiazol-4-yl]prop-2-en-1-one (I-12)

At room temperature, a solution of sodium hydroxide (19 mg) in methanol (0.25 ml) and water (0.05 ml) was added to a solution of 1-[4-(4-acetyl-1,3-thiazol-2-yl)piperidin-1-yl]-2-[5-methyl-3-(trifluoromethyl)-1H-pyrazol-1-yl]ethanone (190 mg) and 2,6-difluorobenzaldehyde (67 mg) in methanol (0.12 ml). The reaction mixture was stirred at room temperature overnight. After aqueous work-up, the mixture was extracted with ethyl acetate and the extracts were dried with sodium sulphate and concentrated under reduced pressure. The residue was purified chromatographically. This gave (2E)-3-(2,6-difluorophenyl)-1-[2-(1-{[5-methyl-3-(trifluoromethyl)-1H-pyrazol-1-yl]acetyl}piperidin-4-yl)-1,3-thiazol-4-yl]prop-2-en-1-one (160 mg).

log P (pH2.7): 3.83

$^1$H NMR (DMSO-d$_6$, 400 MHz): $\delta_{ppm}$: 1.56-1.68 (m, 1H), 1.78-1.91 (m, 1H), 2.10-2.21 (m, 2H), 2.22 (s, 3H), 2.84-2.92 (m, 1H), 3.20-3.50 (m, 2H), 3.95-4.05 (m, 1H), 4.36-4.92 (m, 1H), 5.23 (d, 1H), 5.34 (d, 1H), 6.50 (s, 1H), 7.26 (d, 1H), 7.28 (d, 1H), 7.58 (m, 1H), 7.81 (d, 1H), 8.07 (d, 1H), 8.626 (s, 1H)

MS (ESI): 525 ([M+H]$^+$)

Preparation of Compound (I-11)

Step 1 tert-Butyl 4-(4-ethynyl-1,3-thiazol-2-yl)piperidine-1-carboxylate (VI-1)

Under argon, tert-butyl 4-(4-formyl-1,3-thiazol-2-yl)piperidine-1-carboxylate (600 mg) was dissolved in methanol, and potassium carbonate (839 mg) and dimethyl 1-diazo-2-oxopropylphosphonate (786 mg) were added. The mixture was stirred at room temperature for 3 hours. After aqueous work-up, the mixture was extracted with ethyl acetate, the extracts were dried with sodium sulphate and the solvent was concentrated under reduced pressure. The residue was purified chromatographically. This gave tert-butyl 4-(4-ethynyl-1,3-thiazol-2-yl)piperidine-1-carboxylate (493 mg).

log P (pH2.7): 3.10

$^1$H NMR (CD$_3$CN): $\delta$ 7.51 (s, 1H), 4.07 (d, 2H), 3.36 (s, 1H), 3.16 (m, 1H), 2.90 (t, 2H), 2.10-2.00 (m, 2H), 1.65 (qd, 2H), 1.43 (s, 9H) ppm

MS (ESI): 237 ([M+2H−C(CH$_3$)$_3$]$^+$)

Step 2

1-[4-(4-Ethynyl-1,3-thiazol-2-yl)piperidin-1-yl]-2-[5-methyl-3-(trifluoromethyl)-1H-pyrazol-1-yl]ethanone (XX-1)

At room temperature, a solution of trifluoroacetic acid (30% in dichloromethane, 2 ml) was added to tert-butyl 4-(4-ethynyl-1,3-thiazol-2-yl)piperidine-1-carboxylate (100 mg). After 30 minutes of stirring, triethylamine (2 ml) was added to the reaction mixture.

Oxalyl chloride (130 mg) and a drop of N,N-dimethylformamide were added to a solution of [5-methyl-3-(trifluoromethyl)-1H-pyrazol-1-yl]acetic acid (71 mg) in dichloromethane (2 ml). The reaction mixture was then stirred for 30 minutes. Excess oxalyl chloride was then removed under reduced pressure, and the residue was redissolved in dichloromethane (2 ml). The solution was then added to the first solution. The reaction mixture was stirred for 1 hour. Solvent and triethylamine were removed under reduced pressure, and the residue was then purified chromatographically. This gave 1-[4-(4-ethynyl-1,3-thiazol-2-yl)piperidin-1-yl]-2-[5-methyl-3-(trifluoromethyl)-1H-pyrazol-1-yl]ethanone (130 mg).

log P (pH2.7): 2.61

$^1$H NMR (DMSO-$d_6$, 400 MHz): $\delta_{ppm}$: 1.60 (bs, 1H), 1.76 (bs, 1H), 2.05-2.12 (m, 2H), 2.22 (s, 3H), 2.88 (bs, 1H), 3.20-3.35 (m, 2H), 3.98 (bs, 1H), 4.08 (s, 1H), 4.32 (bs, 1H), 5.20 (bs, 2H), 6.45 (s, 1H), 7.86 (s, 1H)

MS (ESI): 383 ([M+H]$^+$)

Step 3

1-(2-Ethoxyphenyl)-3-[2-(1-{[5-methyl-3-(trifluoromethyl)-1H-pyrazol-1-yl]acetyl}piperidin-4-yl)-1,3-thiazol-4-yl]prop-2-yn-1-one (I-11)

At room temperature and under an atmosphere of argon, palladium(II) chloride (5.8 mg) and copper(I) iodide were added to a solution of 1-[4-(4-ethynyl-1,3-thiazol-2-yl)piperidin-1-yl]-2-[5-methyl-3-(trifluoromethyl)-1H-pyrazol-1-yl]ethanone (250 mg) and 2-ethoxybenzoyl chloride in tetrahydrofuran. The mixture was stirred at room temperature for 1 minute, and triethylamine (83 mg) was then added. The reaction mixture was stirred at room temperature overnight. 5 g of silica gel were then added, and the solvent was removed under reduced pressure. The residue was purified chromatographically. This gave 1-(2-ethoxyphenyl)-3-[2-(1-{[5-methyl-3-(trifluoromethyl)-1H-pyrazol-1-yl]acetyl}piperidin-4-yl)-1,3-thiazol-4-yl]prop-2-yn-1-one (244 mg).

log P (pH2.7): 3.78

$^1$H NMR (CD$_3$CN, 400 MHz): $\delta_{ppm}$: 1.44 (t, 3H), 1.65-1.95 (m, 2H), 2.12-2.21 (m, 2H), 2.24 (s, 3H), 2.90 (bs, 1H), 3.25-3.38 (m, 2H), 3.95 (bs, 1H), 4.22 (q, 2H), 4.43 (1H), 5.04 (bs, 2H), 6.37 (s, 1H), 7.02-7.18 (m, 2H), 7.54-7.60 (m, 1H), 7.87 (dd, 1H), 7.89 (s, 1H)

MS (ESI): 531 ([M+H]$^+$)

Preparation of Compound (I-20)

Step 1

1-(2-Ethoxyphenyl)-3-[2-(1-{[5-methyl-3-(trifluoromethyl)-1H-pyrazol-1-yl]acetyl}piperidin-4-yl)-1,3-thiazol-4-yl]propan-1-one (I-20)

1-(2-Ethoxyphenyl)-3-[2-(1-{[5-methyl-3-(trifluoromethyl)-1H-pyrazol-1-yl]acetyl}piperidin-4-yl)-1,3-thiazol-4-yl]prop-2-yn-1-one (130 mg) was dissolved in methanol and hydrogenated at 40° C. and an H$_2$ pressure of 10 bar and in the presence of Pd/C (10%). This gave, after filtration and removal of the solvent under reduced pressure, 1-(2-ethoxyphenyl)-3-[2-(1-{[5-methyl-3-(trifluoromethyl)-1H-pyrazol-1-yl]acetyl}piperidin-4-yl)-1,3-thiazol-4-yl]propan-1-one (40 mg).

log P (pH2.7): 3.70

$^1$H NMR (CD$_3$CN, 400 MHz): $\delta_{ppm}$: 1.44 (t, 3H), 1.58-1.70 (m, 1H), 1.75-1.86 (m, 1H), 2.06-2.18 (m, 2H), 2.25 (s, 3H), 2.82-2.90 (m, 1H), 3.09 (t, 2H), 3.20-3.32 (m, 2H), 3.42 (t, 2H), 3.88-3.95 (m, 1H), 4.16 (q, 2H), 4.42-4.47 (m, 1H), 5.04 (d, 1H), 5.11 (d, 1H), 6.42 (s, 1H), 6.95 (s, 1H), 7.01 (t, 1H), 7.09 (d, 1H), 7.47-7.53 (m, 1H), 5.59 (dd, 1H)

MS (ESI): 535 ([M+H]$^+$)

Preparation of Compound (I-22)

Step 1 tert-Butyl 4-{4-[(1E)-3-(2,6-difluorophenyl)-3-oxoprop-1-en-1-yl]-1,3-thiazol-2-yl}piperidine-1-carboxylate (IV-3)

tert-Butyl 4-(4-formyl-1,3-thiazol-2-yl)piperidine-1-carboxylate (500 mg) was reacted analogously to I-12 (step 3) with 1-(2,6-difluorophenyl)ethanone (263 mg). This gave tert-butyl 4-{4-[(1E)-3-(2,6-difluorophenyl)-3-oxoprop-1-en-1-yl]-1,3-thiazol-2-yl}piperidine-1-carboxylate (720 mg).

log P (pH2.7): 4.30

$^1$H NMR (DMSO-$d_6$, 400 MHz): $\delta_{ppm}$:1.41 (s, 9H), 1.51-1.61 (m, 2H), 2.00-2.08 (m, 2H), 2.90 (bs, 2H), 3.80-4.04 (m, 3H), 7.15 (d, 1H), 7.27 (t, 2H), 7.47 (d, 1H), 7.60-7.70 (m, 1H), 8.16 (s, 1H)

MS (ESI): 335 ([M-C=OOC(CH$_3$)$_3$+2H]$^+$)

Step 2

(2E)-3-[2-(1-{[3,5-Bis(difluoromethyl)-1H-pyrazol-1-yl]acetyl}piperidin-4-yl)-1,3-thiazol-4-yl]-1-(2,6-difluorophenyl)prop-2-en-1-one (I-22)

tert-Butyl 4-{4-[(1E)-3-(2,6-difluorophenyl)-3-oxoprop-1-en-1-yl]-1,3-thiazol-2-yl}piperidine-1-carboxylate (720 mg) was reacted analogously to II-1 (step 3). This gave 4-{4-[(1E)-3-(2,6-difluorophenyl)-3-oxoprop-1-en-1-yl]-1,3-thiazol-2-yl}piperidinium chloride (800 mg).

4-{4-[(1E)-3-(2,6-Difluorophenyl)-3-oxoprop-1-en-1-yl]-1,3-thiazol-2-yl}piperidinium chloride (300 mg) was reacted analogously to I-24 (step 4) with [3,5-bis(difluoromethyl)-1H-pyrazol-1-yl]acetic acid (183 mg). This gave (2E)-3-[2-(1-{[3,5-bis(difluoromethyl)-1H-pyrazol-1-yl]acetyl}piperidin-4-yl)-1,3-thiazol-4-yl]-1-(2,6-difluorophenyl)prop-2-en-1-one (100 mg).

log P (pH2.7): 3.35

$^1$H NMR (DMSO-$d_6$, 400 MHz): $\delta_{ppm}$: 1.51-1.63 (m, 1H), 1.75-1.88 (m, 1H), 2.05-2.16 (m, 2H), 2.80-2.88 (m, 1H), 3.20-3.42 (m, 2H), 3.92-4.01 (m, 1H), 4.30-4.46 (m, 1H), 5.35 (d, 1H), 5.44 (d, 1H), 6.88 (s, 1H), 7.04 (t, 1H), 7.15-7.20 (m, 1H), 7.18 (t, 1H), 7.24-7.32 (m, 2H), 7.49 (d, 1H), 7.60-7.70 (m, 1H), 8.17 (s, 1H)

MS (ESI): 543 ([M–H]$^+$)

The compounds of the formula (I) listed in Table 1 below can be obtained analogously to the methods given above:

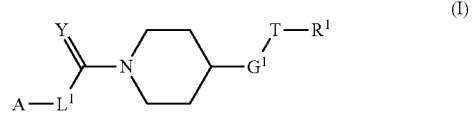

(I)

For all examples of Table 1,

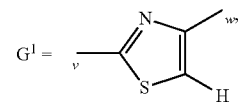

where the bond identified by "v" is attached directly to the piperidine ring and where the bond identified by "w" is attached directly to T. The bond of T identified by "*" is attached to $G^1$, the bond identified by "#" is attached to $R^1$.

TABLE I

| Ex. | A | $L^1$ | Y | T | $R^1$ | log P |
|---|---|---|---|---|---|---|
| I-1 | 5-methyl-3-(trifluoromethyl)-1H-pyrazol-1-yl | $CH_2$ | O | *—C≡C—CO—# | phenyl | $3.58^{[a]}$ |
| I-2 | 5-methyl-3-(trifluoromethyl)-1H-pyrazol-1-yl | $CH_2$ | O | *—C≡C—CO—# | 2-methoxyphenyl | $3.35^{[a]}$; $3.36^{[b]}$ |
| I-3 | 5-methyl-3-(trifluoromethyl)-1H-pyrazol-1-yl | $CH_2$ | O | *—C≡C—CO—# | naphthalen-1-yl | $4.25^{[a]}$ |
| I-4 | 5-methyl-3-(trifluoromethyl)-1H-pyrazol-1-yl | $CH_2$ | O | *—C≡C—CO—# | cyclohexyl | $4.15^{[a]}$ |
| I-5 | 5-methyl-3-(trifluoromethyl)-1H-pyrazol-1-yl | $CH_2$ | O | *—C≡C—CO—# | 2-chlorophenyl | $3.79^{[a]}$ |
| I-6 | 5-methyl-3-(trifluoromethyl)-1H-pyrazol-1-yl | $CH_2$ | O | *—C≡C—CO—# | 2,4-dichlorophenyl | $4.31^{[a]}$ |
| I-7 | 5-methyl-3-(trifluoromethyl)-1H-pyrazol-1-yl | $CH_2$ | O | *—C≡C—CO—# | 4-methoxyphenyl | $3.54^{[a]}$ |
| I-8 | 5-methyl-3-(trifluoromethyl)-1H-pyrazol-1-yl | $CH_2$ | O | *—C≡C—CO—# | tert-butyl | $3.68^{[a]}$ |
| I-9 | 5-methyl-3-(trifluoromethyl)-1H-pyrazol-1-yl | $CH_2$ | O | *—C≡C—CO—# | thiophen-2-yl | $3.29^{[a]}$ |
| I-10 | 5-methyl-3-(trifluoromethyl)-1H-pyrazol-1-yl | $CH_2$ | O | *—C≡C—CO—# | furan-2-yl | $2.92^{[a]}$ |
| I-11 | 5-methyl-3-(trifluoromethyl)-1H-pyrazol-1-yl | $CH_2$ | O | *—C≡C—CO—# | 2-ethoxyphenyl | $3.76^{[a]}$ |
| I-12 | 5-methyl-3-(trifluoromethyl)-1H-pyrazol-1-yl | $CH_2$ | O | *—CO—CH=CH—[E]—# | 2,6-difluorophenyl | $3.83^{[a]}$ |
| I-13 | 5-methyl-3-(trifluoromethyl)-1H-pyrazol-1-yl | $CH_2$ | O | *—CO—$CH_2$—# | 2-bromophenyl | $3.67^{[a]}$; $3.71^{[b]}$ |
| I-14 | 5-methyl-3-(trifluoromethyl)-1H-pyrazol-1-yl | $CH_2$ | O | *—$COCH_2CH_2$—# | phenyl | $3.64^{[a]}$ |
| I-15 | 5-methyl-3-(trifluoromethyl)-1H-pyrazol-1-yl | $CH_2$ | O | *—CO—$CH_2$—$C(CH_3)_2$—# | phenyl | $4.08^{[a]}$ |
| I-16 | 5-methyl-3-(trifluoromethyl)-1H-pyrazol-1-yl | $CH_2$ | O | *—CO—$CH_2$—# | phenyl | $3.36^{[a]}$ |
| I-17 | 5-methyl-3-(trifluoromethyl)-1H-pyrazol-1-yl | $CH_2$ | O | *—CO—$CH_2$—# | cyclohexyl | $4.13^{[a]}$; $4.24^{[b]}$ |
| I-18 | 5-methyl-3-(trifluoromethyl)-1H-pyrazol-1-yl | $CH_2$ | O | *—CO—$CH_2$—# | naphthalen-1-yl | $3.87^{[a]}$ |
| I-19 | 5-methyl-3-(trifluoromethyl)-1H-pyrazol-1-yl | $CH_2$ | O | *—$CH_2CH_2$—CO—# | 2-methoxyphenyl | $3.34^{[a]}$ |
| I-20 | 5-methyl-3-(trifluoromethyl)-1H-pyrazol-1-yl | $CH_2$ | O | *—$CH_2CH_2$—CO—# | 2-ethoxyphenyl | $3.7^{[a]}$; $3.68^{[b]}$ |
| I-21 | 5-methyl-3-(trifluoromethyl)-1H-pyrazol-1-yl | $CH_2$ | O | *—$CH_2CH_2$—CO—# | 2-chlorophenyl | $3.6^{[a]}$; $3.63^{[b]}$ |
| I-22 | 3,5-bis(difluoromethyl)-1H-pyrazol-1-yl | $CH_2$ | O | *—CH=CH—CO—[E]—# | 2,6-difluorophenyl | $3.35^{[a]}$ |
| I-23 | 2,5-dimethylphenyl | NH | O | *—CH=CH—CO—[E]—# | 2,6-difluorophenyl | $3.56^{[a]}$ |
| I-24 | 3,5-bis(difluoromethyl)-1H-pyrazol-1-yl | $CH_2$ | O | *—CO—$CH_2$—# | cyclohexyl | $4.02^{[a]}$; $4.09^{[b]}$ |
| I-25 | 5-chloro-2-methylphenyl | NH | O | *—CO—$CH_2$—# | cyclohexyl | $4.51^{[a]}$; $4.55^{[b]}$ |
| I-26 | 5-methyl-3-(trifluoromethyl)-1H-pyrazol-1-yl | $CH_2$ | O | *—C(Cl)=CHCO—[E and/or Z]—# | phenyl | $4^{[a]}$ |
| I-29 | 3,5-bis(difluoromethyl)-1H-pyrazol-1-yl | $CH_2$ | O | *—CH=CHCO—[E]—# | 2-bromophenyl | $3.51^{[a]}$; $3.49^{[b]}$ |
| I-30 | 2,5-bis(difluoromethyl)-phenyl | —NH— | O | *—$COCH_2$—# | cyclohexyl | $4.3^{[a]}$; $4.34^{[b]}$ |
| I-33 | 3,5-bis(difluoromethyl)-1H-pyrazol-1-yl | $CH_2$ | O | *—CH=CHCO—[E]—# | 2-iodophenyl | $3.65^{[a]}$; $3.64^{[b]}$ |
| I-34 | 3,5-Bis(difluormethyl)-1H-pyrazol-1-yl | $CH_2$ | O | *—CH=CHCO—[E]—# | 2-bromo-4-fluorphenyl | $3.7^{[a]}$; $3.68^{[b]}$ |
| I-35 | 3,5-bis(difluoromethyl)-1H-pyrazol-1-yl | $CH_2$ | O | *—CH=CHCO—[E]—# | 2-chloro-5-fluorophenyl | $3.64^{[a]}$; $3.6^{[b]}$ |
| I-36 | 3,5-bis(difluoromethyl)-1H-pyrazol-1-yl | $CH_2$ | O | *—CH=CHCO—[E]—# | 2-chloro-6-fluorophenyl | $3.54^{[a]}$; $3.51^{[b]}$ |
| I-37 | 3,5-bis(difluoromethyl)-1H-pyrazol-1-yl | $CH_2$ | O | *—CH=CHCO—[E]—# | phenyl | $3.31^{[a]}$; $3.31^{[b]}$ |
| I-38 | 3,5-bis(difluoromethyl)-1H-pyrazol-1-yl | $CH_2$ | O | *—CH=CHCO—[E]—# | 3-methylphenyl | $3.64^{[a]}$; $3.63^{[b]}$ |
| I-39 | 3,5-bis(difluoromethyl)-1H-pyrazol-1-yl | $CH_2$ | O | *—CH=CHCO—[E]—# | 2,6-dimethoxyphenyl | $3.04^{[a]}$ |
| I-40 | 3,5-bis(difluoromethyl)-1H-pyrazol-1-yl | $CH_2$ | O | *—CH=CHCO—[E]—# | 4-fluorophenyl | $3.43^{[a]}$ |
| I-41 | 3,5-bis(difluoromethyl)-1H-pyrazol-1-yl | $CH_2$ | O | *—CH=CHCO—[E]—# | 3-fluorophenyl | $3.48^{[a]}$ |
| I-42 | 3,5-bis(difluoromethyl)-1H-pyrazol-1-yl | $CH_2$ | O | *—CH=CHCO—[E]—# | 2-chlorophenyl | $3.51^{[a]}$ |

TABLE I-continued

| Ex. | A | L¹ | Y | T | R¹ | log P |
|---|---|---|---|---|---|---|
| I-43 | 3,5-bis(difluoromethyl)-1H-pyrazol-1-yl | CH₂ | O | *—CH=CHCO—[E]—# | 2,6-dichlorophenyl | 3.7[a] |
| I-44 | 3,5-bis(difluoromethyl)-1H-pyrazol-1-yl | CH₂ | O | *—CH=CHCO—[E]—# | cyclohexyl | 3.89[a] |
| I-45 | 3,5-bis(difluoromethyl)-1H-pyrazol-1-yl | CH₂ | O | *—CH=CHCO—[E]—# | 2-methylphenyl | 3.56[a] |
| I-46 | 3,5-bis(difluoromethyl)-1H-pyrazol-1-yl | CH₂ | O | *—CH=CHCO—[E]—# | naphthalen-1-yl | 2.84[a] |
| I-47 | 3,5-bis(difluoromethyl)-1H-pyrazol-1-yl | CH₂ | O | *—CH=CHCO—[E]—# | tert-butyl | 3.45[a] |
| I-48 | 3,5-bis(difluoromethyl)-1H-pyrazol-1-yl | CH₂ | O | *—CH=CHCO—[E]—# | 2-fluoro-4-methoxyphenyl | 3.45[a] |
| I-49 | 3,5-bis(difluoromethyl)-1H-pyrazol-1-yl | CH₂ | O | *—CH=CHCO—[E]—# | cyclopentyl | 3.52[a] |
| I-50 | 3,5-bis(difluoromethyl)-1H-pyrazol-1-yl | CH₂ | O | *—CH=CHCO—[E]—# | 2-methylcyclohexyl | 4.11[a] |
| I-51 | 3,5-bis(difluoromethyl)-1H-pyrazol-1-yl | CH₂ | O | *—CH(CH3)CH₂CO—# | 2,6-difluorophenyl | |
| I-52 | 3,5-bis(difluoromethyl)-1H-pyrazol-1-yl | CH₂ | O | *—CH=CHCO—[E]—# | 2-fluorophenyl | 3.35[a] |
| I-55 | 3,5-bis(difluoromethyl)-1H-pyrazol-1-yl | CH₂ | O | *—CH=CHCO—[E]—# | 2-(prop-2-yn-1-yloxy)phenyl | 3.28[a] |
| I-57 | 3,5-bis(difluoromethyl)-1H-pyrazol-1-yl | CH₂ | O | *—CH=CHCO—[E]—# | 2,4,6-trifluorophenyl | 3.51[a]; 3.5[b] |
| I-58 | 3,5-bis(difluoromethyl)-1H-pyrazol-1-yl | CH₂ | S | *—COCH₂—# | cyclohexyl | 4.63[a]; 4.56[b] |
| I-59 | 3,5-bis(difluoromethyl)-1H-pyrazol-1-yl | CH₂ | O | *—COCH₂—# | 2,3-dimethylphenyl | 3.71[a] |
| I-60 | 3,5-bis(difluoromethyl)-1H-pyrazol-1-yl | CH₂ | O | *—C(=NOCH₃)CH₂—[Z]—# | cyclohexyl | 4.8[a] |
| I-61 | 3,5-bis(difluoromethyl)-1H-pyrazol-1-yl | CH₂ | O | *—C(=NOCH₃)CH₂—[Z]—# | 2,3-dimethylphenyl | 4.33[a] |
| I-62 | 3,5-bis(difluoromethyl)-1H-pyrazol-1-yl | CH₂ | O | *—COCH=CH—[E]—# | 2,6-difluorophenyl | 3.68[a]; 3.59[b] |
| I-63 | 3,5-bis(difluoromethyl)-1H-pyrazol-1-yl | CH₂ | O | *—CH=CHCO—[E]—# | 2,6-dimethylphenyl | 3.65[a]; 3.64[b] |
| I-64 | 3,5-bis(difluoromethyl)-1H-pyrazol-1-yl | CH₂ | O | *—CH=CHC(=NOH)—[E,E]—# | 2-(prop-2-yn-1-yloxy)phenyl | 3.08[a][d]; 3.30[a][e] |
| I-65 | 5-methyl-3-(trifluoromethyl)-1H-pyrazol-1-yl | CH₂ | O | *—C(Cl)=CHCO—[E and/or Z]—# | 2-methoxyphenyl | 3.96[a][d]; 3.79[a][e] |

[d] major isomer;
[e] minor isomer
The logP values were determined according to EEC directive 79/831 Annex V.A8 by HPLC (High Performance Liquid Chromatography) on reversed-phase columns (C 18), using the methods below:
[a]The LC-MS determination in the acidic range is carried out at pH 2.7 using the mobile phases 0.1% aqueous formic acid and acetonitrile (contains 0.1% formic acid); linear gradient from 10% acetonitrile to 95% acetonitrile
[b]The LC-MS determination in the neutral range is carried out at pH 7.8 using the mobile phases 0.001 molar aqueous ammonium bicarbonate solution and acetonitrile; linear gradient from 10% acetonitrile to 95% acetonitrile Calibration was carried out using unbranched alkan-2-ones (having from 3 to 16 carbon atoms) with known log P values (the log P values were determined by the retention times using linear interpolation between two successive alkanones).

The lambda max values were determined in the maxima of the chromatographic signals using the UV spectra from 200 nm to 400 nm.

NMR Data of Selected Examples

| Ex. | NMR data |
|---|---|
| I-1 | ¹H NMR (CD₃CN, 400 MHz): $\delta_{ppm}$: 1.65-1.76 (m, 1H), 1.83-1.95 (m, 1H), 2.10-2.21 (m, 2H), 2.23 (s, 3H), 2.82-2.91 (m, 1H), 3.25-3.40 (m, 2H), 3.90-3.98 (m, 1H), 4.45-4.53 (m, 1H), 5.04 (d, 1H), 5.11 (d, 1H), 6.40 (s, 1H), 7.56-7.63 (m, 2H), 7.70-7.75 (m, 1H), 8.08 (s, 1H), 8.18-8.22 (m, 2H) |
| I-2 | ¹H NMR (CD₃CN, 400 MHz): $\delta_{ppm}$: 1.65-1.76 (m, 1H), 1.83-1.95 (m, 1H), 2.10-2.20 (m, 2H), 2.23 (s, 3H), 2.82-2.91 (m, 1H), 3.25-3.39 (m, 2H), 3.90-3.97 (m, 1H), 3.95 (s, 3H), 4.45-4.51 (m, 1H), 5.04 (d, 1H), 5.11 (d, 1H), 6.39 (s, 1H), 7.08 (t, 1H), 7.17 (d, 1H), 7.60-7.65 (m, 1H), 7.97 (s, 1H), 7.97-8.00 (m, 1H) |
| I-3 | ¹H NMR (CD₃CN, 400 MHz): $\delta_{ppm}$: 1.65-1.78 (m, 1H), 1.82-1.95 (m, 1H), 2.13-2.20 (m, 2H), 2.23 (s, 3H), 2.80-2.90 (m, 1H), 3.25-3.40 (m, 2H), 3.90-3.98 (m, 1H), 4.45-4.53 (m, 1H), 5.04 (d, 1H), 5.11 (d, 1H), 6.40 (s, 1H), 7.10-7.25 (m, 3H), 8.02 (d, 1H), 8.06 (s, 1H), 8.23 (d, 1H), 8.69 (d, 1H), 9.15 (d, 1H) |
| I-4 | ¹H NMR (DMSO-d₆, 400 MHz): $\delta_{ppm}$: 1.15-1.48 (m, 5H), 1.50-1.88 (m, 5H), 1.92-1.99 (m, 2H), 2.07-2.15 (m, 2H), 2.22 (s, 3H), 2.50-2.59 (m, 1H), 2.88 (bs, 1H), 3.20-3.41 (m, 2H), 3.99 (bs, 1H), 4.32 (bs, 1H), 5.21 (bs, 2H), 6.45 (s, 1H), 8.31 (a, 1H) |

| Ex. | NMR data |
| --- | --- |
| I-5 | $^1$H NMR (CD$_3$CN, 400 MHz): δ$_{ppm}$: 1.70-1.95 (m, 2H), 2.18-2.25 (m, 2H), 2.29 (s, 3H), 2.97 (bs, 1H), 3.25-3.44 (m, 2H), 4.01 (bs, 1H), 4.50 (bs, 1H), 5.10 (bs, 2H), 6.42 (s, 1H), 7.52-7.65 (m, 3H), 8.05 (s, 1H), 8.16(dd, 1H) |
| I-6 | $^1$H NMR (CD$_3$CN, 400 MHz): δ$_{ppm}$: 1.64-1.74 (m, 1H), 1.80-1.91 (m, 1H), 2.10-2.23 (m, 2H), 2.23 (s, 3H), 2.80-2.89 (m, 1H), 3.25-3.38 (m, 2H), 3.89-3.95 (m, 1H), 4.45-4.51 (m, 1H), 5.04 (d, 1H), 5.11 (d, 1H), 6.39 (s, 1H), 7.53 (dd, 1H), 7.63 (d, 1H), 8.06 (s, 1H), 8.14 (d, 1H) |
| I-7 | $^1$H NMR(CD$_3$CN, 400 MHz): δ$_{ppm}$: 1.71-2.05 (m, 2H), 2.11-2.21 (m, 2H), 2.24 (s, 3H), 2.90 (bs, 1H), 3.24-3.40 (m, 2H), 3.90 (s, 3H), 3.98 (bs, 1H), 4.45 (bs, 1H), 5.05 (bs, 2H), 6.37 (s, 1H), 7.05-7.95 (m, 2H), 7.99 (s, 1H), 8.13-8.18 (m, 2H) |
| I-8 | $^1$H NMR (CD$_3$CN, 400 MHz): δ$_{ppm}$: 1.25 (s, 9H), 1.62-1.90 (m, 2H), 2.10-2.19 (m, 2H), 2.24 (s, 3H), 2.89 (bs, 1H), 3.20-3.37 (m, 2H), 3.95 (bs, 1H), 4.44 (bs, 1H), 5.04 (bs, 2H), 6.36 (s, 1H), 7.89 (s, 1H) |
| I-9 | $^1$H NMR (CD$_3$CN, 400 MHz): δ$_{ppm}$: 1.70-1.95 (m, 2H), 2.13-2.22 (m, 2H), 2.24 (s, 3H), 2.91 (bs, 1H), 3.23-3.40 (m, 2H), 3.95 (bs, 1H), 4.44 (bs, 1H), 5.05 (bs, 2H), 6.37 (s, 1H), 7-26 (dd, 1H), 7.90 (dd, 1H), 8.01 (s, 1H), 8.06 (dd, 1H) |
| I-10 | $^1$H NMR (CD$_3$CN, 400 MHz): δ$_{ppm}$: 1.68-1.95 (m, 2H), 2.10-2.20 (m, 2H), 2.24 (s, 3H), 2.92 (bs, 1H), 3.22-3.40 (m, 2H), 3.98 (bs, 1H), 4.46 (bs, 1H), 5.05 (bs, 2H), 6.37 (s, 1H), 6.69 (dd, 1H), 7.52 (d, 1H), 7.82 (d, 1H), 7.99 (s, 1H) |
| I-11 | $^1$H NMR (CD$_3$CN, 400 MHz): δ$_{ppm}$: 1.44 (t, 3H), 1.65-1.95 (m, 2H), 2.12-2.21 (m, 2H), 2.24 (s, 3H), 2.90 (bs, 1H), 3.25-3.38 (m, 2H), 3.95 (bs, 1H), 4.22 (q, 2H), 4.43 (1H), 5.04 (bs, 2H), 6.37 (s, 1H), 7.02-7.18 (m, 2H), 7.54-7.60 (m, 1H), 7.87 (dd, 1H), 7.89 (s, 1H) |
| I-12 | $^1$H NMR (DMSO-d$_6$, 400 MHz): δ$_{ppm}$: 1.56-1.68 (m, 1H), 1.78-1.91 (m, 1H), 2.10-2.21 (m, 2H), 2.22 (s, 3H), 2.84-2.92 (m, 1H), 3.20-3.50 (m, 2H), 3.95-4.05 (m, 1H), 4.36-4.92 (m, 1H), 5.23 (d, 1H), 5.34 (d, 1H), 6.50 (s, 1H), 7.26 (d, 1H), 7.28 (d, 1H), 7.58 (m, 1H), 7.81 (d, 1H), 8.07 (d, 1H), 8.626 (s, 1H) |
| I-13 | $^1$H NMR (DMSO-d$_6$, 400 MHz): δ$_{ppm}$: 1.56-1.68 (m, 1H), 1.80-1.91 (m, 1H), 2.10-2.22 (m, 2H), 2.22 (s, 3H), 2.83-2.92 (m, 1H), 3.25-3.35 (m, 1H), 3.40-3.48 (m, 1H), 3.96-4.03 (m, 1H), 4.35-4.42 (m, 1H), 4.57 (s, 2H), 5.24 (d, 1H), 5.33 (d, 1H), 6.50 (s, 1H), 7.23 (td, 1H), 7.33-7.42 (m, 2H), 7.62 (dd, 1H), 8.54 (s, 1H) |
| I-14 | $^1$H NMR (DMSO-d$_6$, 400 MHz): δ$_{ppm}$: 1.41 (s, 9H), 1.48-1.61 (m, 2H), 1.90-2.11 (4H), 2.62-2.67 (m, 2H), 2.87-2.95 (m, 2H), 3.15-3.20 (m, 1H), 3.94-4.00 (2H), 4.62-4.67 (m, 1H), 5.09-5.12 (m, 1H), 7.11-7.18 (m, 3H), 7.22-7.27 (m, 3H) |
| I-15 | $^1$H NMR (DMSO-d$_6$, 400 MHz): δ$_{ppm}$: 1.41 (s, 6H), 1.52-1.85 (m, 2H), 2.08-2.15 (m, 2H), 2.23 (s, 3H), 2.90 (bs, 1H), 3.20-3.40 (m, 2H), 3.41 (s, 2H), 3.99 (bs, 1H), 4.34 (bs, 1H), 5.22 (bs, 2H), 6.45 (s, 1H), 7.08-7.13 (m, 1H), 7.21-7.26 (m, 2H), 7.35-7.39 (m, 2H), 8.22 (s, 1H) |
| I-16 | $^1$H NMR (DMSO-d$_6$, 400 MHz): δ$_{ppm}$: 1.58-1.90 (m, 2H), 2.12-2.19 (m, 2H), 2.23 (s, 3H), 2.93 (bs, 1H), 3.31 (bs, 1H), 3.36-3.47 (m, 1H), 4.00 (bs, 1H), 4.32 (bs, 1H), 4.33 (s, 2H), 5.17-5.27 (m, 2H), 6.45 (s, 1H), 7.18-7.32 (m, 5H), 8.43 (s, 1H) |
| I-17 | $^1$H NMR (DMSO-d$_6$, 400 MHz): δ$_{ppm}$: 0.94-1.05 (m, 2H), 1.10-1.29 (m, 3H), 1.54-1.71 (m, 6H), 1.75-1.93 (m, 2H), 2.06-2.18 (m, 2H), 2.21 (s, 3H), 2.81-2.89 (m, 1H), 2.89 (d, 2H), 3.22-3.45 (m, 2H), 3.94-4.01 (m, 1H), 4.33-4.40 (m, 1H), 5.22 (d, 1H), 5.33 (d, 1H), 6.50 (s, 1H), 8.42 (s, 1H) |
| I-18 | $^1$H NMR (DMSO-d$_6$, 400 MHz): δ$_{ppm}$: 1.60-1.91 (m, 2H), 2.11-2.21 (m, 2H), 2.23 (s, 3H), 2.92 (bs, 1H), 3.31 (bs, 1H), 3.40-3.49 (m, 1H), 4.02 (bs, 1H), 4.34 (bs, 1H), 4.83 (s, 2H), 5.22 (bs, 2H), 6.45 (s, 1H), 7.43-7.52 (m, 3H), 7.79-7.82 (m, 2H), 7.88-7.94 (m, 1H), 7.97-8.01 (m, 1H), 8.46 (s, 1H) |
| I-19 | $^1$H NMR (CD$_3$CN, 400 MHz): δ$_{ppm}$: 1.55-1.67 (m, 1H), 1.72-1.83 (m, 1H), 2.03-2.14 (m, 2H), 2.22 (s, 3H), 2.79-2.87 (m, 1H), 3.06 (t, 2H), 3.19-3.35 (m, 2H), 3.34 (t, 2H), 3.85-3.92 (m, 1H), 3.88 (s, 3H), 4.40-4.46 (m, 1H), 5.03 (d, 1H), 5.08 (d, 1H), 6.39 (s, 1H), 6.98 (s, 1H), 7.00 (t, 1H), 7.09 (d, 1H), 7.45-7.56 (m, 2H) |
| I-20 | $^1$H NMR (CD$_3$CN, 400 MHz): δ$_{ppm}$: 1.44 (t, 3H), 1.58-1.70 (m, 1H), 1.75-1.86 (m, 1H), 2.06-2.18 (m, 2H), 2.25 (s, 3H), 2.82-2.90 (m, 1H), 3.09 (t, 2H), 3.20-3.32 (m, 2H), 3.42 (t, 2H), 3.88-3.95 (m, 1H), 4.16 (q, 2H), 4.42-4.47 (m, 1H), 5.04 (d, 1H), 5.11 (d, 1H), 6.42 (s, 1H), 6.95 (s, 1H), 7.01 (t, 1H), 7.09 (d, 1H), 7.47-7.53 (m, 1H), 5.59 (dd, 1H) |
| I-21 | $^1$H NMR (CD$_3$CN, 400 MHz): δ$_{ppm}$: 1.55-1.66 (m, 1H), 1.71-1.82 (m, 1H), 2.02-2.15 (m, 2H), 2.22 (s, 3H), 2.78-2.86 (m, 1H), 3.08 (t, 2H), 3.18-3.33 (m, 2H), 3.32 (t, 2H), 3.85-3.92 (m, 1H). 4.39-4.46 (m, 1H), 5.02 (d, 1H), 5.09 (d, 1H), 6.39 (s, 1H), 6.96 (s, 1H), 7.35-7.52 (m, 4H) |
| I-22 | $^1$H NMR (DMSO-d$_6$, 400 MHz): δ$_{ppm}$: 1.51-1.63 (m, 1H), 1.75-1.88 (m, 1H), 2.05-2.16 (m, 2H), 2.80-2.88 (m, 1H), 3.20-3.42 (m, 2H), 3.92-4.01 (m, 1H), 4.30-4.46 (m, 1H), 5.35 (d, 1H), 5.44 (d. 1H), 6.88 (s, 1H), 7.04 |

| Ex. | NMR data |
|---|---|
| | (t, 1H), 7.15-7.20 (m, 1H), 7.18 (t, 1H), 7.24-7.32 (m, 2H), 7.49 (d, 1H), 7.60-7.70 (m, 1H), 8.17 (s, 1H) |
| I-23 | $^1$H NMR (DMSO-d$_6$, 400 MHz): δ$_{ppm}$: 1.62-1.69 (m, 2H), 2.05-2.09 (m, 2H), 2.11 (s, 3H), 2.23 (s, 3H), 2.95-3.01 (m, 2H), 3.29-3.35 (m, 1H), 4.13-4.17 (m, 2H), 6.86 (d, 1H), 6.99 (s, 1H), 7.04 (d, 1H), 7.17 (d, 1H), 7.27-7.32 (m, 2H), 7.49 (d, 1H), 7.63-7.68 (m, 1H), 8.03 (s, 1H), 8.18 (s, 1H) |
| I-24 | $^1$H NMR (DMSO-d$_6$, 400 MHz): δ$_{ppm}$: 0.95-1.02 (m, 2H), 1.10-1.26 (m, 3H), 1.54-1.69 (m, 6H), 1.77-1.91 (m, 2H), 2.06-2.15 (m, 2H), 2.82-2.87 (m, 1H), 2.89 (d, 2H), 3.25-3.30 (m, 1H), 3.35-3.41 (m, 1H), 3.94-3.99 (m, 1H), 4.33-4.37 (m, 1H), 5.36 (d, 1H), 5.45 (d, 1H), 6.91 (s, 1H), 7.04 (t, 1H), 7.18 (1, 1H), 8.44 (s, 1H) |
| I-25 | $^1$H NMR (DMSO-d$_6$, 400 MHz): δ$_{ppm}$: 0.94-1.05 (m, 2H), 1.10-1.26 (m, 4H), 1.56-1.73 (m, 6H), 1.83-1.92 (m, 1H), 2.06-2.13 (m, 2H), 2.16 (s, 3H), 2.88 (d, 2H), 2.98-3.06 (m, 2H), 3.30-3.38 (m, 1H), 4.11-4.18 (m, 2H), 7.07 (dd, 1H), 7.19 (d, 1H), 7.33 (d, 1H), 8.12 (s, 1H), 8.04 (s, 1H) |

The 1H-NMR data of selected examples are given in the form of 1H-NMR peak lists. For each signal peak, the δ value in ppm and the signal intensity are listed:

| Ex. | NMR peak list data |
|---|---|
| I-26 | [DMSO-D$_6$] 8.1231 6.35; 8.0482 7.38; 7.9751 0.56; 7.9599 2.84; 7.9569 3.62; 7.9443 1.14; 7.9392 4.50; 7.9357 3.58; 7.8555 0.74; 7.8509 1.42; 7.8379 0.77; 7.8343 0.72; 7.6973 0.46; 7.6939 0.91; 7.6907 0.51; 7.6806 0.67; 7.6755 2.23; 7.6706 0.80; 7.6604 1.05; 7.6571 1.85; 7.6537 0.93; 7.5924 3.06; 7.5886 1.33; 7.5760 2.41; 7.5729 4.24; 7.5589 1.05; 7.5547 2.02; 7.5528 1.33; 7.5417 0.38; 7.4696 0.59; 7.4502 0.78; 7.4321 0.37; 7.0164 1.35; 6.4681 0.77; 6.4582 0.72; 6.4485 3.44; 5.6885 5.31; 5.2322 0.85; 5.2161 0.86; 5.1375 1.62; 4.9763 2.78; 4.0644 0.46; 4.0468 1.31; 4.0289 1.42; 4.0112 0.61; 3.5676 0.65; 3.4437 0.34; 3.4342 0.61; 3.4244 0.38; 3.4159 0.68; 3.4063 1.22; 3.3965 0.76; 3.3876 0.47; 3.3782 0.74; 3.3689 0.42; 3.2752 0.36; 3.2544 0.34; 3.1201 134.75; 3.0183 0.50; 2.9006 0.33; 2.6626 0.42; 2.6579 0.59; 2.6533 0.42; 2.5272 0.49; 2.5111 1.30; 2.5064 1.84; 2.4982 32.10; 2.4935 66.61; 2.4888 94.30; 2.4841 66.08; 2.4794 31.81; 2.3203 0.38; 2.3157 0.60; 2.3109 0.44; 2.2578 3.63; 2.2563 3.71; 2.2265 15.73; 2.2250 16.00; 2.1931 0.80; 2.1744 0.92; 2.1442 1.08; 2.0406 0.95; 1.9742 5.50; 1.9015 0.40; 1.6943 0.40; 1.6725 0.38; 1.6649 0.36; 1.6591 0.40; 1.6396 0.35; 1.2449 0.45; 1.1952 1.59; 1.1774 3.19; 1.1597 1.59; −0.0001 2.84 |
| I-29 | [DMSO-D$_6$] 8.1441 11.91; 7.7596 3.68; 7.7418 3.77; 7.7397 4.01; 7.6802 0.35; 7.6610 0.38; 7.5576 1.03; 7.5549 1.06; 7.5382 3.23; 7.5215 4.67; 7.5188 4.35; 7.5112 3.71; 7.5060 6.34; 7.4917 5.35; 7.4861 3.10; 7.4745 2.90; 7.4721 3.56; 7.4689 2.31; 7.4665 2.27; 7.4549 1.87; 7.4492 1.33; 7.4147 0.37; 7.4013 0.34; 7.3191 4.88; 7.3060 2.61; 7.2797 8.40; 7.1972 0.86; 7.1779 8.71; 7.1727 6.14; 7.1580 2.85; 7.1386 4.51; 7.0394 2.75; 7.0219 6.38; 6.8997 5.57; 6.8860 3.13; 5.4484 1.02; 5.4057 4.32; 5.3696 4.24; 5.3445 0.38; 5.3267 1.03; 4.3555 1.27; 4.3222 1.34; 4.0571 1.33; 4.0393 3.75; 4.0215 3.79; 4.0038 1.44; 3.9800 1.26; 3.9453 1.36; 3.4781 0.43; 3.4577 0.49; 3.4356 0.72; 3.4109 1.52; 3.4017 1.30; 3.3918 1.86; 3.3825 2.70; 3.3729 2.13; 3.3631 2.09; 3.3537 2.84; 3.3057 573.68; 3.2826 9.11; 3.2429 1.20; 2.8901 1.16; 2.8789 0.91; 2.8508 1.60; 2.8206 0.91; 2.7321 0.68; 2.6740 0.89; 2.6695 1.12; 2.6648 0.82; 2.5394 2.52; 2.5091 62.88; 2.5048 112.86; 2.5004 143.95; 2.4960 99.46; 2.4917 47.75; 2.3315 0.71; 2.3271 0.91; 2.3225 0.67; 2.1468 1.23; 2.1107 2.33; 2.0697 1.63; 1.9869 16.00; 1.8609 0.43; 1.8514 0.48; 1.8237 1.11; 1.8017 0.98; 1.7928 0.89; 1.7702 0.38; 1.6262 0.43; 1.6163 0.48; 1.5961 1.00; 1.5879 1.06; 1.5650 0.98; 1.5573 0.90; 1.5367 0.40; 1.2363 0.48; 1.1928 4.35; 1.1750 8.73; 1.1572 4.22; 0.9264 0.37; 0.0080 0.67; −0.0002 11.85; −0.0084 0.46 |
| I-30 | [DMSO-D$_6$] 8.6206 4.81; 8.4136 16.00; 7.7324 0.47; 7.7047 2.72; 7.6850 3.18; 7.5317 4.01; 7.4853 2.48; 7.4658 2.02; 7.2201 2.26; 7.2139 1.78; 7.0810 4.92; 7.0761 4.14; 6.9500 0.37; 6.9418 2.61; 4.2512 0.33; 4.2282 0.34; 4.1744 2.50; 4.1403 2.58; 4.0571 0.57; 4.0393 1.54; 4.0215 1.61; 4.0036 0.60; 3.7222 1.42; 3.7090 0.46; 3.6975 0.44; 3.5947 0.39; 3.5678 1.69; 3.4175 0.41; 3.4044 0.54; 3.3904 1.05; 3.3810 1.53; 3.3707 1.63; 3.3619 2.31; 3.3517 3.59; 3.3135 2176.06; 3.2900 33.84; 3.2738 1.64; 3.2531 0.61; 3.0807 1.68; 3.0522 3.15; 3.0228 1.72; 2.8922 9.42; 2.8752 9.74; 2.6790 0.68; 2.6744 1.35; 2.6699 1.88; 2.6651 1.34; 2.6608 0.69; 2.5398 3.16; 2.5231 5.65; 2.5184 8.38; 2.5097 103.40; 2.5053 202.26; 2.5008 272.55; 2.4963 187.40; 2.4918 88.41; 2.3320 1.34; 2.3275 1.94; 2.3229 1.39; 2.3182 0.64; 2.1176 2.00; 2.0914 2.31; 2.0856 2.24; 2.0691 6.17; 2.0494 0.37; 1.9869 6.91; 1.9197 0.44; 1.9097 0.65; 1.9003 0.94; 1.8916 0.94; 1.8828 1.19; 1.8743 1.04; 1.8649 0.76; 1.8555 0.77; 1.8460 0.49; 1.8393 0.33; 1.7467 0.73; 1.7363 0.91; 1.7146 1.85; 1.7063 2.08; 1.6841 4.03; 1.6751 4.16; 1.6565 4.64; 1.6501 3.99; 1.6325 2.59; 1.6263 2.30; 1.5853 1.04; 1.3985 0.45; 1.2841 0.36; 1.2718 0.58; 1.2411 1.68; 1.2180 1.77; 1.2099 2.18; 1.1928 2.46; 1.1874 1.53; 1.1751 5.58; 1.1572 2.51; 1.1491 1.32; 1.1195 0.86; 1.0386 0.94; 1.0324 1.09; 1.0041 2.29; 0.9743 1.82; 0.9499 0.64; 0.9395 0.49; −0.0001 5.55 |
| I-33 | [DMSO-D$_6$] 8.1416 7.23; 7.9858 2.56; 7.9664 2.64; 7.5640 1.19; 7.5462 2.69; 7.5281 1.81; 7.4712 0.37; 7.4521 2.56; 7.4481 2.76; 7.4331 2.10; 7.4292 1.92; 7.4220 0.39; 7.3303 0.72; 7.3051 1.95; 7.2949 4.15; 7.2793 2.46; 7.2753 2.39; 7.2557 6.06; 7.2010 0.33; 7.1713 4.28; 7.1679 5.64; 7.1572 1.93; 7.1284 2.66; 7.0388 1.80; 7.0211 3.80; 6.9590 0.32; 6.9000 3.83; 6.8854 1.90; 5.4476 0.81; 5.4045 2.98; 5.3871 0.76; 5.3690 2.96; 5.3273 0.85; 4.3570 1.12; 4.3185 1.12; 4.2594 0.41; 4.2556 0.36; 4.1721 0.48; 4.1607 0.41; 4.1086 0.44; 4.0905 |

| Ex. | NMR peak list data |
|---|---|
| | 0.48; 4.0727 0.51; 4.0568 1.63; 4.0392 4.13; 4.0215 4.29; 4.0034 1.80; 3.9821 1.27; 3.9679 1.10; 3.9456 1.34; 3.9094 0.67; 3.8857 0.67; 3.8808 0.78; 3.8652 0.75; 3.8537 0.73; 3.7222 1.37; 3.6832 1.62; 3.6610 1.85; 3.6523 1.86; 3.6335 2.02; 3.6298 1.99; 3.5555 2.99; 3.4880 4.86; 3.3256 3385.14; 3.2484 4.44; 3.1974 2.05; 3.1152 1.41; 3.1033 1.39; 3.0967 1.29; 3.0836 1.22; 3.0670 1.02; 3.0343 1.05; 3.0223 0.96; 2.9873 0.87; 2.9446 0.88; 2.9150 0.86; 2.9014 0.97; 2.8821 1.42; 2.8499 2.05; 2.8220 1.49; 2.7990 1.00; 2.7843 1.05; 2.7708 1.02; 2.7565 1.08; 2.7296 1.25; 2.6955 2.61; 2.6702 3.41; 2.6661 2.97; 2.5403 11.32; 2.5057 258.17; 2.5014 323.27; 2.4973 233.05; 2.4329 1.69; 2.4245 1.31; 2.4158 1.07; 2.3762 0.73; 2.3676 0.70; 2.3320 2.03; 2.3281 2.50; 2.2801 0.54; 2.2681 0.50; 2.2450 0.46; 2.2164 0.51; 2.1967 0.60; 2.1900 0.52; 2.1779 0.78; 2.1570 1.27; 2.1516 1.30; 2.1150 2.00; 2.0844 1.70; 2.0686 2.66; 2.0489 0.68; 2.0398 0.47; 2.0179 0.55; 1.9867 16.00; 1.9595 0.42; 1.9414 0.36; 1.9203 0.46; 1.9076 0.60; 1.9035 0.58; 1.8815 0.49; 1.8643 0.62; 1.8534 0.78; 1.8276 1.06; 1.8055 0.93; 1.7744 0.56; 1.7633 0.52; 1.7524 0.36; 1.7370 0.40; 1.7172 0.32; 1.6846 0.33; 1.6321 0.58; 1.6218 0.57; 1.5907 1.01; 1.5674 0.96; 1.5634 0.92; 1.4347 0.33; 1.3982 1.38; 1.2917 0.36; 1.2355 0.75; 1.2291 0.51; 1.2133 0.47; 1.1929 4.61; 1.1751 8.54; 1.1574 4.31; 1.0366 0.33; −0.0002 5.53 |
| I-34 | [DMSO-D$_6$] 8.1326 4.77; 7.7556 1.35; 7.7495 1.36; 7.7338 1.36; 7.7277 1.30; 7.6227 1.19; 7.6075 1.32; 7.6013 1.54; 7.5861 1.39; 7.4392 0.85; 7.4330 0.81; 7.4179 1.53; 7.4117 1.40; 7.3966 0.72; 7.3904 0.66; 7.3518 2.08; 7.3126 3.32; 7.3064 1.15; 7.1775 3.36; 7.1732 2.50; 7.1580 1.13; 7.1384 1.91; 7.0399 1.10; 7.0219 2.47; 6.9006 2.17; 6.8860 1.21; 5.4501 0.42; 5.4064 1.72; 5.3694 1.67; 5.3271 0.42; 4.3574 0.53; 4.3232 0.53; 4.0571 1.27; 4.0392 3.71; 4.0214 3.73; 4.0036 1.33; 3.9819 0.51; 3.9477 0.55; 3.4127 0.72; 3.4027 0.68; 3.3938 0.92; 3.3840 1.30; 3.3745 1.13; 3.3083 410.62; 3.2447 0.51; 2.8802 0.36; 2.8502 0.67; 2.8210 0.37; 2.6741 0.43; 2.6694 0.57; 2.6647 0.42; 2.5396 1.36; 2.5093 31.74; 2.5049 57.40; 2.5005 73.67; 2.4961 51.08; 2.4917 24.52; 2.3320 0.35; 2.3272 0.46; 2.3227 0.32; 2.1467 0.53; 2.1121 0.92; 2.0693 0.85; 1.9868 16.00; 1.8299 0.41; 1.8237 0.46; 1.7994 0.38; 1.7922 0.36; 1.5982 0.41; 1.5894 0.42; 1.5672 0.38; 1.5578 0.36; 1.1928 4.47; 1.1750 8.78; 1.1572 4.31; −0.0002 2.18 |
| I-35 | [DMSO-D$_6$] 8.1524 10.14; 7.6638 2.28; 7.6518 2.45; 7.6417 2.83; 7.6297 2.73; 7.5019 2.25; 7.4944 3.06; 7.4809 2.39; 7.4733 3.03; 7.4636 2.19; 7.4559 1.54; 7.4427 2.99; 7.4346 2.07; 7.4209 1.82; 7.4132 1.23; 7.3880 4.78; 7.3486 6.57; 7.3068 2.09; 7.2890 0.40; 7.2189 0.39; 7.1709 7.64; 7.1580 2.65; 7.1313 4.26; 7.0462 0.74; 7.0403 2.41; 7.0220 5.38; 6.9590 0.34; 6.9009 4.78; 6.8861 2.72; 5.7461 16.00; 5.4494 0.94; 5.4074 3.67; 5.3893 0.62; 5.3699 3.71; 5.3271 0.90; 5.2962 0.85; 4.3562 1.10; 4.3249 1.13; 4.2641 0.33; 4.2522 0.39; 4.2400 0.34; 4.0572 0.84; 4.0395 2.42; 4.0217 2.47; 4.0039 0.95; 3.9826 1.07; 3.9495 1.17; 3.6968 0.35; 3.6930 0.36; 3.6843 0.55; 3.6729 0.75; 3.6637 0.58; 3.6512 0.38; 3.5681 0.54; 3.4416 0.48; 3.4149 1.26; 3.4056 1.13; 3.3956 1.61; 3.3864 2.39; 3.3769 1.98; 3.3671 2.06; 3.3138 679.74; 3.2457 1.26; 3.0376 0.32; 2.8818 0.78; 2.8506 1.55; 2.8225 0.79; 2.6748 0.58; 2.6701 0.76; 2.6656 0.56; 2.5401 1.68; 2.5098 43.12; 2.5055 78.38; 2.5011 100.99; 2.4967 70.61; 2.4924 34.59; 2.3325 0.54; 2.3278 0.69; 2.3232 0.54; 2.1470 1.05; 2.1123 2.00; 2.0694 1.35; 1.9871 10.39; 1.8628 0.39; 1.8583 0.40; 1.8521 0.45; 1.8320 0.89; 1.8239 0.98; 1.8014 0.84; 1.7715 0.36; 1.7633 0.32; 1.6205 0.46; 1.5984 0.89; 1.5901 0.95; 1.5688 0.87; 1.5608 0.83; 1.5391 0.36; 1.2359 0.41; 1.1930 2.90; 1.1753 5.73; 1.1574 2.83; −0.0002 3.83 |
| I-36 | [DMSO-D$_6$] 8.1773 7.83; 7.6322 0.91; 7.6164 1.11; 7.6112 2.06; 7.5960 2.17; 7.5909 1.51; 7.5752 1.34; 7.4931 3.38; 7.4729 2.41; 7.4336 1.63; 7.4113 2.75; 7.3872 3.63; 7.3470 4.08; 7.3062 1.64; 7.1729 3.65; 7.1584 1.82; 7.1246 4.22; 7.0852 3.07; 7.0397 1.80; 7.0223 4.02; 6.9007 3.62; 6.8864 2.01; 5.4484 0.70; 5.4053 2.95; 5.3701 2.86; 5.3281 0.70; 4.3546 0.89; 4.3227 0.91; 4.0572 1.28; 4.0395 3.75; 4.0217 3.79; 4.0039 1.37; 3.9818 0.86; 3.9475 0.93; 3.4377 0.56; 3.4221 0.84; 3.4139 1.17; 3.4041 1.11; 3.3951 1.53; 3.3857 2.19; 3.3762 1.98; 3.3136 766.08; 3.2443 1.08; 2.8810 0.62; 2.8506 1.18; 2.8241 0.66; 2.6747 0.64; 2.6701 0.82; 2.6654 0.62; 2.5399 1.92; 2.5097 49.29; 2.5055 88.69; 2.5011 113.23; 2.4967 79.02; 2.4926 38.38; 2.3323 0.57; 2.3278 0.74; 2.3229 0.57; 2.1466 0.85; 2.1100 1.57; 2.0693 1.39; 1.9871 16.00; 1.8543 0.33; 1.8317 0.68; 1.8244 0.76; 1.8027 0.69; 1.6207 0.34; 1.6005 0.67; 1.5914 0.71; 1.5697 0.67; 1.5619 0.63; 1.4039 0.53; 1.1930 4.42; 1.1752 8.75; 1.1574 4.28; −0.0002 2.58 |
| I-37 | [DMSO-D$_6$] 8.1616 16.00; 8.0401 8.89; 8.0224 10.20; 8.0188 8.00; 7.9030 0.42; 7.8856 0.55; 7.8818 0.43; 7.8365 5.64; 7.7983 10.55; 7.7190 11.16; 7.7010 2.08; 7.6979 1.48; 7.6813 9.55; 7.6672 2.70; 7.6642 4.06; 7.6611 2.34; 7.6069 7.16; 7.5875 10.45; 7.5693 4.54; 7.4781 0.36; 7.4590 0.50; 7.3184 3.26; 7.1851 7.42; 7.1645 3.65; 7.0519 3.67; 7.0285 8.29; 6.9891 0.40; 6.9572 0.46; 6.9076 7.49; 6.8926 4.22; 6.6263 0.45; 6.5951 0.37; 5.4668 1.50; 5.4242 5.66; 5.3824 5.56; 5.3398 1.53; 5.3181 0.75; 4.3941 1.69; 4.3606 1.77; 4.0571 1.03; 4.0393 3.16; 4.0215 3.78; 4.0038 2.55; 3.9740 1.79; 3.5680 0.97; 3.4493 0.98; 3.4400 1.67; 3.4303 1.35; 3.4209 2.07; 3.4113 3.29; 3.4018 2.38; 3.3922 2.10; 3.3823 2.85; 3.3729 2.70; 3.3125 1921.95; 3.1672 0.70; 3.1034 0.49; 3.0697 0.43; 3.0466 0.38; 3.0374 0.40; 2.8905 1.40; 2.8613 2.26; 2.8325 1.34; 2.6954 0.60; 2.6790 0.84; 2.6745 1.47; 2.6699 1.90; 2.6652 1.43; 2.5399 4.06; 2.5229 9.24; 2.5095 110.27; 2.5053 201.65; 2.5008 260.70; 2.4965 183.97; 2.4922 90.87; 2.3322 1.53; 2.3276 1.98; 2.3230 1.51; 2.1793 1.79; 2.1479 3.46; 2.1144 1.92; 2.0693 0.89; 1.9869 13.51; 1.9082 0.69; 1.8916 0.66; 1.8836 0.82; 1.8623 1.46; 1.8530 1.55; 1.8305 1.46; 1.8238 1.42; 1.8005 0.68; 1.6775 0.67; 1.6666 0.80; 1.6450 1.52; 1.6365 1.61; 1.6143 1.47; 1.6060 1.34; 1.5960 0.64; 1.5853 0.63; 1.5746 0.53; 1.3983 1.42; 1.2358 0.74; 1.1929 3.79; 1.1751 7.42; 1.1573 3.71; 0.8902 0.34; −0.0002 2.24 |
| I-38 | [DMSO-D$_6$] 8.1561 7.74; 7.8566 0.37; 7.8334 5.18; 7.8152 3.93; 7.7767 5.16; 7.7497 0.35; 7.7080 5.45; 7.6698 2.67; 7.5071 0.70; 7.5026 0.68; 7.4865 5.18; 7.4671 2.46; 7.4480 0.82; 7.3179 1.59; 7.1846 3.56; 7.1638 1.91; 7.0513 1.77; 7.0278 4.10; 6.9068 3.59; 6.8920 2.12; 5.4675 0.71; 5.4248 2.68; 5.3818 2.65; 5.3389 0.85; 4.3976 0.82; 4.3643 0.84; 4.0571 1.06; 4.0393 3.04; 4.0215 3.33; 4.0038 1.68; 3.9757 0.84; 3.5679 0.65; 3.4497 0.44; 3.4407 0.74; 3.4310 0.63; 3.4213 0.94; 3.4119 1.51; 3.4029 1.09; 3.3922 0.91; 3.3827 1.29; 3.3734 1.16; 3.3106 847.89; 3.2606 1.74; 2.8865 0.63; 2.8590 1.06; 2.8271 0.65; 2.6744 0.68; 2.6697 0.90; 2.6652 0.67; 2.6607 0.39; 2.5765 0.35; 2.5608 1.10; 2.5398 1.95; 2.5228 4.26; 2.5095 50.87; 2.5051 93.57; 2.5007 121.23; 2.4963 85.30; 2.4920 42.05; 2.4215 16.00; 2.3809 0.65; 2.3656 |

| Ex. | NMR peak list data |
|---|---|
| | 1.42; 2.3319 0.79; 2.3272 1.23; 2.1795 0.84; 2.1466 1.68; 2.1134 0.93; 2.0693 0.42; 1.9869 12.96; 1.8882 0.34; 1.8796 0.38; 1.8582 0.69; 1.8502 0.73; 1.8273 0.71; 1.8240 0.69; 1.7982 0.33; 1.6711 0.33; 1.6606 0.39; 1.6385 0.68; 1.6312 0.76; 1.6095 0.70; 1.5999 0.65; 1.3984 0.70; 1.2360 0.33; 1.1929 3.60; 1.1751 7.09; 1.1573 3.53; −0.0002 0.86 |
| I-39 | [DMSO-$D_6$] 8.0529 2.63; 7.4083 0.69; 7.3873 1.39; 7.3663 0.80; 7.3046 0.54; 7.1713 1.24; 7.1572 0.83; 7.1539 1.29; 7.1145 1.75; 7.0380 0.63; 7.0216 1.35; 6.9734 1.68; 6.9340 1.07; 6.8995 1.24; 6.8857 0.67; 6.7675 2.92; 6.7464 2.73; 5.7462 2.13; 5.4023 0.98; 5.3669 0.97; 5.2961 0.37; 3.7483 0.73; 3.7297 0.96; 3.7183 16.00; 3.6726 0.38; 3.3900 0.39; 3.3710 0.55; 3.3621 0.81; 3.3520 0.80; 3.3120 148.95; 3.2739 0.52; 3.2692 0.52; 3.1774 0.33; 2.8482 0.36; 2.5397 0.32; 2.5093 9.70; 2.5051 17.38; 2.5007 22.12; 2.4964 15.46; 2.0966 0.55; 2.0691 0.42;1.9869 0.66;1.1751 0.38 |
| I-40 | [DMSO-$D_6$] 8.1658 16.00; 8.1537 1.38; 8.1463 6.35; 8.1411 3.10; 8.1324 7.18; 8.1242 7.06; 8.1155 3.20; 8.1103 6.18; 7.8314 5.38; 7.7934 10.54; 7.7232 11.07; 7.6852 5.42; 7.4246 6.41; 7.4198 2.50; 7.4025 12.01; 7.3853 2.51; 7.3804 5.93; 7.3287 0.58; 7.3200 3.34; 7.1867 7.49; 7.1659 3.73; 7.0534 3.64; 7.0299 8.05; 6.9096 7.63; 6.8940 4.13; 5.7478 8.22; 5.4673 1.53; 5.4248 5.92; 5.3843 5.83; 5.3421 1.61; 4.3962 1.81; 4.3639 1.89; 4.0579 0.37; 4.0400 1.00; 4.0221 1.56; 4.0047 1.88; 3.9742 1.86; 3.4467 0.76; 3.4379 1.37; 3.4280 1.08; 3.4184 1.72; 3.4091 2.88; 3.3999 1.80; 3.3901 1.27; 3.3804 1.69; 3.3714 1.12; 3.3059 258.95; 3.2617 1.92; 2.8898 1.27; 2.8608 2.24; 2.8319 1.28; 2.6751 0.45; 2.6705 0.58; 2.6661 0.43; 2.5404 1.00; 2.5099 34.49; 2.5058 61.68; 2.5014 78.48; 2.4972 55.77; 2.3326 0.48; 2.3283 0.60; 2.3235 0.46; 2.1782 1.69; 2.1462 3.51; 2.1120 1.96; 2.0707 0.36; 1.9876 3.68; 1.8915 0.62; 1.8809 0.72; 1.8599 1.47; 1.8518 1.55; 1.8298 1.47; 1.8221 1.38; 1.7999 0.62; 1.7897 0.51; 1.6799 0.62; 1.6710 0.77; 1.6497 1.51; 1.6409 1.60; 1.6192 1.46; 1.6106 1.39; 1.5891 0.59; 1.5794 0.50; 1.1934 1.02; 1.1756 1.98; 1.1578 1.00; −0.0002 2.56 |
| I-41 | [DMSO-$D_6$] 8.1966 16.00; 7.9032 4.15; 7.8838 4.79; 7.8736 0.65; 7.8076 3.98; 7.7992 2.84; 7.7930 3.32; 7.7893 2.92; 7.7694 15.05; 7.7407 13.03; 7.7026 3.85; 7.6729 1.85; 7.6584 2.23; 7.6527 3.53; 7.6382 3.57; 7.6332 2.61; 7.6186 2.20; 7.5794 0.35; 7.5584 2.16; 7.5536 1.96; 7.5374 3.17; 7.5320 2.93; 7.5178 1.45; 7.5159 1.46; 7.5112 1.36; 7.3183 3.17; 7.2152 0.48; 7.1850 7.11; 7.1646 3.72; 7.0517 3.54; 7.0286 7.98; 6.9075 7.40; 6.8927 4.12; 5.7472 7.53; 5.4663 1.46; 5.4241 5.62; 5.3831 5.56; 5.3407 1.65; 5.3275 0.53; 4.3943 1.71; 4.3616 1.80; 4.0575 0.36; 4.0398 0.94; 4.0219 1.45; 4.0045 1.76; 3.9740 1.76; 3.4478 0.76; 3.4389 1.51; 3.4291 1.10; 3.4199 1.75; 3.4103 2.74; 3.4010 1.80; 3.3909 1.32; 3.3815 1.84; 3.3721 1.26; 3.3093 504.59; 3.2858 10.43; 3.2613 2.21; 3.1909 0.40; 3.1817 0.36; 2.8901 1.23; 2.8603 2.16; 2.8324 1.25; 2.6750 0.52; 2.6704 0.69; 2.6659 0.54; 2.5403 1.13; 2.5099 40.78; 2.5057 74.07; 2.5013 95.31; 2.4970 68.09; 2.3327 0.58; 2.3282 0.75; 2.3233 0.58; 2.1812 1.62; 2.1474 3.34; 2.1138 1.88; 2.0702 0.38; 1.9874 3.52; 1.8930 0.64; 1.8834 0.72; 1.8625 1.42; 1.8542 1.49; 1.8315 1.41; 1.8243 1.34; 1.8023 0.63; 1.7924 0.52; 1.6773 0.63; 1.6680 0.75; 1.6468 1.48; 1.6378 1.54; 1.6161 1.44; 1.6072 1.35; 1.5864 0.60; 1.5775 0.48; 1.2348 0.40; 1.1933 0.98; 1.1755 1.92; 1.1577 0.98; −0.0002 2.25 |
| I-42 | [DMSO-$D_6$] 9.6022 0.51; 8.1426 16.00; 8.1000 0.44; 7.6087 1.85; 7.6058 2.17; 7.5886 7.11; 7.5868 6.55; 7.5851 6.19; 7.5820 4.73; 7.5772 4.59; 7.5655 4.35; 7.5606 5.97; 7.5567 3.74; 7.5517 3.37; 7.5462 1.73; 7.5411 4.80; 7.5359 7.56; 7.5327 4.36; 7.5119 5.22; 7.5077 5.25; 7.4955 3.89; 7.4925 4.83; 7.4883 2.58; 7.4762 1.72; 7.4724 1.65; 7.4214 0.33; 7.3567 6.58; 7.3442 0.48; 7.3174 11.38; 7.3054 3.64; 7.2919 0.47; 7.2126 10.79; 7.1726 12.70; 7.1575 4.07; 7.0464 0.85; 7.0388 3.87; 7.0214 8.53; 6.9989 0.46; 6.9656 0.43; 6.8997 7.57; 6.8856 4.42; 6.2908 0.40; 6.2754 0.37; 5.7463 7.66; 5.4482 1.44; 5.4054 5.92; 5.3888 1.38; 5.3685 5.82; 5.3261 1.46; 5.2949 0.54; 5.2788 0.55; 4.3552 1.70; 4.3220 1.80; 4.0392 0.32; 4.0215 0.39; 3.9786 1.58; 3.9462 1.77; 3.6839 0.32; 3.6720 0.36; 3.5679 0.70; 3.4728 0.35; 3.4485 0.47; 3.4115 1.95; 3.4019 1.88; 3.3925 2.79; 3.3835 4.22; 3.3733 3.67; 3.3107 2339.33; 3.2435 3.77; 3.1939 1.38; 3.1526 0.83; 3.1441 0.81; 3.0746 0.52; 3.0209 0.43; 2.9962 0.35; 2.9745 0.36; 2.9605 0.33; 2.9565 0.34; 2.9265 0.35; 2.9100 0.35; 2.8784 1.39; 2.8524 2.31; 2.8212 1.38; 2.7681 0.33; 2.6955 0.42; 2.6742 1.96; 2.6697 2.54; 2.6651 1.88; 2.6192 0.39; 2.5396 4.00; 2.5226 12.06; 2.5093 145.42; 2.5050 264.34; 2.5006 339.77; 2.4962 237.87; 2.4920 117.25; 2.3747 0.67; 2.3716 0.59; 2.3579 0.58; 2.3497 0.55; 2.3366 1.23; 2.3318 2.03; 2.3273 2.66; 2.3228 2.02; 2.3019 0.47; 2.2849 0.41; 2.2255 0.33; 2.2202 0.34; 2.2162 0.33; 2.1927 0.34; 2.1429 1.76; 2.1103 3.38; 2.0692 3.06; 1.9869 1.67; 1.9078 0.46; 1.8600 0.75; 1.8515 0.87; 1.8217 1.66; 1.7989 1.50; 1.7925 1.40; 1.7706 0.70; 1.7493 0.32; 1.6417 0.36; 1.6269 0.71; 1.6175 0.84; 1.5959 1.49; 1.5872 1.59; 1.5658 1.48; 1.5573 1.41; 1.5359 0.68; 1.3983 0.38; 1.2361 1.25; 1.1928 0.61; 1.1749 1.07; 1.1572 0.59; 1.0271 0.58; 0.8902 0.42; −0.0002 4.66 |
| I-43 | [DMSO-$D_6$] 8.1720 14.54; 7.6305 6.14; 7.6255 7.71; 7.6087 16.00; 7.6074 16.00; 7.5745 8.52; 7.5580 5.31; 7.5511 3.66; 7.5394 0.60; 7.5347 2.63; 7.5074 9.53; 7.2679 9.62; 7.1737 6.57; 7.1590 3.22; 7.0746 8.73; 7.0404 3.64; 7.0351 6.55; 7.0230 7.51; 6.9008 6.24; 6.8871 3.63; 5.7468 9.42; 5.4475 1.13; 5.4051 5.10; 5.3719 5.08; 5.3295 1.10; 4.3546 1.43; 4.3212 1.50; 3.9811 1.35; 3.9467 1.46; 3.4212 0.76; 3.4118 1.24; 3.4020 1.00; 3.3927 1.54; 3.3834 2.49; 3.3739 1.67; 3.3640 1.31; 3.3550 1.83; 3.3451 1.62; 3.3057 532.18; 3.2430 1.10; 2.8798 0.99; 2.8505 1.73; 2.8229 0.98; 2.6743 0.57; 2.6697 0.76; 2.6652 0.57; 2.5397 1.04; 2.5228 3.13; 2.5095 43.31; 2.5051 80.87; 2.5006 105.64; 2.4962 72.60; 2.4918 34.34; 2.3319 0.51; 2.3274 0.70; 2.3228 0.49; 2.1460 1.23; 2.1109 2.57; 2.0761 1.48; 2.0697 2.08; 1.9871 0.34; 1.8677 0.43; 1.85760.52; 1.8371 1.09; 1.8282 1.16; 1.8061 1.08; 1.7981 1.00; 1.7764 0.44; 1.7668 0.35; 1.6318 0.42; 1.6227 0.53; 1.6019 1.10; 1.5928 1.18; 1.5713 1.11; 1.5628 1.06; 1.5420 0.45; 1.5330 0.36; 0.0080 0.91; −0.0002 21.13; −0.0084 0.80 |
| I-44 | [DMSO-$D_6$] 8.0076 16.00; 7.5620 7.74; 7.5229 8.94; 7.3109 3.30; 7.1776 7.54; 7.1606 3.72; 7.0444 3.71; 7.0246 8.50; 7.0016 8.77; 6.9624 7.56; 6.9033 7.09; 6.8887 4.24; 5.7458 7.11; 5.4559 1.43; 5.4133 5.52; 5.3717 5.46; 5.3291 1.43; 4.3700 1.59; 4.3368 1.68; 4.0395 0.48; 4.0217 0.54; 3.9873 1.51; 3.9526 1.65; 3.4072 0.82; 3.3978 1.47; 3.3885 1.21; 3.3787 1.90; 3.3692 3.11; 3.3597 2.31; 3.3494 2.32; 3.3398 3.75; 3.3125 811.08; 3.2891 6.55; 3.2722 3.23; 3.2425 1.55; 2.8735 1.16; 2.8462 2.03; 2.8160 1.18; 2.7890 0.76; 2.7808 1.11; 2.7718 |

| Ex. | NMR peak list data |
|---|---|
| | 0.85; 2.7617 1.77; 2.7536 2.28; 2.7453 1.29; 2.7344 1.26; 2.7266 1.30; 2.6792 0.32; 2.6744 0.58; 2.6700 0.77; 2.6654 0.59; 2.5400 1.06; 2.5231 2.82; 2.5098 41.65; 2.5054 78.84; 2.5009 103.87; 2.4965 72.41; 2.4921 35.05; 2.3323 0.58; 2.3276 0.74; 2.3230 0.55; 2.1412 1.46; 2.1087 3.04; 2.0691 2.21; 1.9869 2.02; 1.8576 0.66; 1.8486 0.85; 1.8145 4.71; 1.7863 4.49; 1.7557 2.72; 1.7487 3.00; 1.7410 2.68; 1.7240 3.48; 1.7174 4.43; 1.6634 1.69; 1.6318 2.31; 1.6232 1.88; 1.6021 1.41; 1.5927 1.46; 1.5714 1.36; 1.5628 1.29; 1.5420 0.57; 1.5316 0.47; 1.3981 0.51; 1.3911 0.60; 1.3835 0.81; 1.3603 1.87; 1.3529 2.68; 1.3209 4.92; 1.3078 3.17; 1.2903 6.56; 1.2644 2.70; 1.2579 2.99; 1.2346 1.37; 1.2280 1.35; 1.2204 1.12; 1.2119 0.95; 1.1929 1.76; 1.1898 1.76; 1.1817 1.38; 1.1753 1.84; 1.1682 0.93; 1.1576 1.58; 1.1517 0.93; 1.1384 0.38; 1.1303 0.44; −0.0002 1.84 |
| I-45 | [DMSO-D$_6$] 8.1080 7.57; 7.8502 0.34; 7.5392 1.54; 7.5353 1.71; 7.5296 0.62; 7.5187 2.18; 7.5165 2.17; 7.4670 0.76; 7.4637 0.76; 7.4483 1.94; 7.4450 1.65; 7.4296 1.63; 7.4262 1.46; 7.3967 2.30; 7.3577 7.53; 7.3514 2.76; 7.3416 2.36; 7.3319 1.81; 7.3232 1.13; 7.3115 6.23; 7.2725 2.19; 7.1752 3.35; 7.1676 0.47; 7.1588 1.71; 7.0420 1.66; 7.0304 0.42; 7.0227 3.82; 6.9019 3.16; 6.8868 1.93; 5.7458 2.90; 5.4523 0.59; 5.4097 2.46; 5.3896 0.53; 5.3711 2.44; 5.3292 0.70; 4.3626 0.70; 4.3298 0.73; 3.9844 0.65; 3.9506 0.72; 3.4132 0.57; 3.4042 0.46; 3.3943 0.75; 3.3848 1.24; 3.3755 0.91; 3.3651 0.81; 3.3563 1.21; 3.3172 394.60; 3.2752 1.65; 3.2468 0.83; 2.8817 0.52; 2.8509 0.96; 2.8238 0.52; 2.6703 0.35; 2.5759 0.78; 2.5429 0.67; 2.5404 0.53; 2.5236 1.24; 2.5102 19.67; 2.5058 37.43; 2.5013 49.46; 2.4968 34.40; 2.4924 16.69; 2.4237 0.37; 2.3502 16.00; 2.3327 0.50; 2.3280 0.51; 2.3236 0.39; 2.1503 0.67; 2.1166 1.34; 2.0824 0.76; 2.0693 0.65; 1.9871 0.62; 1.8345 0.60; 1.8276 0.64; 1.8041 0.60; 1.7975 0.55; 1.6048 0.57; 1.5958 0.61; 1.5740 0.57; 1.5651 0.55; 1.1753 0.35; −0.0002 5.31 |
| I-46 | [DMSO-D$_6$] 8.2538 0.55; 8.2464 2.60; 8.2378 2.12; 8.2347 2.34; 8.2281 1.60; 8.2220 2.83; 8.1638 3.93; 8.1432 4.27; 8.1115 16.00; 8.0617 2.86; 8.0565 2.00; 8.0492 2.57; 8.0456 2.60; 8.0379 3.08; 8.0297 0.58; 7.8844 3.94; 7.8817 4.05; 7.8667 4.91; 7.8639 4.50; 7.7642 0.76; 7.6727 4.14; 7.6642 0.56; 7.6547 4.45; 7.6523 4.57; 7.6423 0.70; 7.6345 4.12; 7.6246 6.02; 7.6190 4.20; 7.6137 4.57; 7.6106 4.56; 7.6058 4.05; 7.6002 6.58; 7.5888 1.05; 7.5827 0.40; 7.5410 1.71; 7.5020 14.99; 7.4927 14.47; 7.4782 0.38; 7.4538 1.63; 7.3082 2.72; 7.1749 6.26; 7.1590 3.10; 7.1437 0.43; 7.0417 3.11; 7.0325 0.86; 7.0230 7.09; 6.9977 0.40; 6.9665 0.52; 6.9025 6.29; 6.8871 3.50; 6.7280 0.46; 6.6967 0.38; 5.7462 12.28; 5.4531 1.14; 5.4104 4.61; 5.3909 0.50; 5.3709 4.52; 5.3284 1.15; 5.2700 0.36; 5.2559 0.36; 4.3684 1.31; 4.3351 1.40; 4.0578 0.48; 4.0400 1.47; 4.0222 1.52; 4.0043 0.79; 3.9874 1.31; 3.9536 1.42; 3.4899 0.57; 3.4196 1.07; 3.4100 0.87; 3.4001 1.34; 3.3910 2.26; 3.3817 1.55; 3.3715 1.30; 3.3622 1.96; 3.3196 789.08; 3.2752 2.90; 3.2467 1.47; 3.0381 0.49; 2.8795 1.00; 2.8512 2.01; 2.8221 0.98; 2.6753 0.48; 2.6709 0.62; 2.6664 0.48; 2.5409 0.77; 2.5241 2.11; 2.5107 33.80; 2.5063 64.26; 2.5019 84.75; 2.4974 59.16; 2.4930 28.67; 2.3332 0.51; 2.3285 0.65; 2.3239 0.49; 2.1541 1.23; 2.1216 2.54; 2.0873 1.44; 2.0699 0.84; 1.9875 6.45; 1.8702 0.47; 1.8618 0.54; 1.8393 1.10; 1.8316 1.17; 1.8097 1.10; 1.8017 1.02; 1.7795 0.47; 1.7697 0.41; 1.6407 0.45; 1.6312 0.58; 1.6099 1.07; 1.6009 1.16; 1.5794 1.10; 1.5706 1.03; 1.5491 0.48; 1.5397 0.39; 1.2345 0.60; 1.1933 1.90; 1.1755 3.61; 1.1577 1.79; 0.0081 0.37; −0.0002 9.08; −0.0083 0.39 |
| I-47 | [DMSO-D$_6$] 8.0468 1.47; 7.5409 0.62; 7.5028 1.01; 7.3802 0.96; 7.3422 0.60; 7.1786 0.70; 7.1604 0.36; 7.0454 0.35; 7.0244 0.79; 6.9036 0.67; 6.8885 0.41; 5.4185 0.50; 5.3705 0.50; 3.3180 74.17; 2.5103 3.27; 2.5059 6.15; 2.5014 8.08; 2.4970 5.64; 2.4927 2.73; 1.1568 16.00; 1.0780 0.44 |
| I-48 | [DMSO-D$_6$] 8.1047 5.08; 7.8248 1.17; 7.8028 2.14; 7.7814 0.98; 7.6546 0.54; 7.6500 0.56; 7.6164 2.14; 7.6120 2.06; 7.5928 1.97; 7.5860 1.94; 7.5547 0.48; 7.5478 0.50; 7.3152 0.97; 7.1819 2.21; 7.1620 1.12; 7.0487 1.09; 7.0259 2.52; 6.9976 1.12; 6.9916 1.33; 6.9637 0.87; 6.9571 2.99; 6.9508 0.98; 6.9354 1.52; 6.9293 1.17; 6.9059 2.12; 6.8901 1.28; 5.7462 1.77; 5.4651 0.46; 5.4226 1.58; 5.3754 1.60; 5.3330 0.45; 4.3811 0.48; 4.3467 0.50; 4.0039 0.41; 3.9974 0.47; 3.9625 0.51; 3.8751 16.00; 3.8388 1.04; 3.5688 0.58; 3.4328 0.49; 3.4228 0.42; 3.4136 0.63; 3.4043 0.94; 3.3950 0.66; 3.3853 0.56; 3.3754 0.74; 3.3659 0.69; 3.3209 214.30; 3.2901 0.87; 3.2858 0.87; 3.2541 0.41; 2.8861 0.33; 2.8554 0.58; 2.8286 0.34; 2.5413 0.33; 2.5245 0.85; 2.5112 10.46; 2.5069 19.22; 2.5024 24.80; 2.4980 16.91; 2.4936 7.87; 2.1657 0.42; 2.1299 0.85; 2.0948 0.47; 1.9877 0.79; 1.8415 0.38; 1.8332 0.39; 1.8105 0.37; 1.8037 0.34; 1.6143 0.38; 1.6061 0.40; 1.5846 0.38; 1.5756 0.35; 1.1758 0.42; −0.0002 0.46 |
| I-49 | [DMSO-D$_6$] 9.6003 0.61; 8.0177 16.00; 7.5816 8.06; 7.5556 8.77; 7.3632 0.40; 7.3605 0.34; 7.2989 0.38; 7.2743 2.73; 7.2673 0.33; 7.2175 0.34; 7.1857 6.39; 7.1784 0.61; 7.1287 3.26; 7.0972 3.11; 7.0605 0.61; 7.0383 7.66; 6.9762 0.37; 6.9703 0.58; 6.9520 8.89; 6.9480 3.85; 6.9259 7.98; 6.9154 7.06; 6.3327 0.60; 6.3226 0.62; 5.4579 2.40; 5.4294 5.41; 5.4039 0.99; 5.3792 5.39; 5.3644 0.41; 5.3509 2.44; 5.3087 0.77; 5.2972 0.39; 5.2893 0.33; 4.3668 1.60; 4.3487 1.64; 4.3448 1.67; 4.1728 0.35; 4.1637 0.34; 3.9801 1.48; 3.9568 1.62; 3.6698 0.48; 3.6598 0.47; 3.4003 0.60; 3.3941 1.23; 3.3879 0.77; 3.3811 1.49; 3.3749 2.61; 3.3685 1.68; 3.3618 1.37; 3.3438 592.30; 3.3202 11.51; 3.3150 1.54; 3.3028 2.20; 3.3004 2.26; 3.2884 4.89; 3.2764 2.49; 3.2740 2.60; 3.2656 2.49; 3.2624 2.60; 3.2465 1.40; 3.2426 1.12; 2.8581 1.03; 2.8539 1.46; 2.8363 1.99; 2.8332 2.06; 2.8159 1.22; 2.8119 1.02; 2.6205 0.45; 2.6176 0.98; 2.6146 1.40; 2.6116 1.01; 2.5423 0.52; 2.5239 2.52; 2.5208 3.20; 2.5177 3.15; 2.5088 75.70; 2.5058 163.26; 2.5028 224.58; 2.4998 163.62; 2.4968 76.90; 2.3929 0.53; 2.3900 1.06; 2.3870 1.47; 2.3840 1.07; 2.3811 0.53; 2.1352 1.38; 2.1152 1.65; 2.0948 1.52; 2.0768 2.25; 1.9558 2.53; 1.8583 0.73; 1.8509 1.97; 1.8417 2.34; 1.8364 3.21; 1.8317 2.66; 1.8276 2.78; 1.8206 3.17; 1.8150 3.13; 1.8054 1.50; 1.7998 1.58; 1.7937 1.41; 1.7799 0.71; 1.7732 0.63; 1.7219 0.79; 1.7097 2.70; 1.6972 3.10; 1.6888 2.85; 1.6846 2.05; 1.6766 2.32; 1.6662 0.84; 1.6638 0.94; 1.6199 0.33; 1.6008 2.09; 1.5913 6.28; 1.5845 8.13; 1.5782 10.69; 1.5734 5.83; 1.5679 4.51; 1.5590 2.66; 1.5460 0.99; 1.5386 0.78; 1.4972 0.40; 1.4097 1.92; 1.3893 0.44; 1.2336 0.96; 1.1708 0.45; 1.0236 0.38; 0.0052 0.81; −0.0002 27.57; −0.0057 0.89 |
| I-50 | [DMSO-D$_6$] 8.0244 14.36; 7.9983 1.29; 7.6093 6.63; 7.5701 7.63; 7.5310 0.62; 7.4919 0.67; 7.3112 3.18; 7.1779 7.28; 7.1611 3.67; 7.0446 3.64; 7.0354 0.96; 7.0251 8.22; 6.9964 0.61; 6.9733 7.58; 6.9341 6.68; 6.9039 7.11; 6.8892 4.39; 5.7457 4.24; 5.4559 1.35; 5.4133 |

| Ex. | NMR peak list data |
|---|---|
| | 5.41; 5.3722 5.38; 5.3298 1.43; 5.2957 0.59; 4.3705 1.56; 4.3368 1.70; 4.0396 0.55; 4.0218 0.62; 3.9878 1.49; 3.9532 1.65; 3.6730 0.43; 3.4016 1.37; 3.3915 1.09; 3.3821 1.76; 3.3728 2.86; 3.3631 2.32; 3.3168 815.40; 3.2783 3.69; 3.2444 1.84; 2.9482 0.33; 2.9225 0.37; 2.8758 1.20; 2.8455 2.05; 2.8176 1.15; 2.6750 0.59; 2.6704 0.77; 2.6661 0.56; 2.5493 1.43; 2.5405 1.78; 2.5102 39.56; 2.5058 72.67; 2.5013 94.78; 2.4969 66.70; 2.4926 32.43; 2.3324 0.52; 2.3280 0.73; 2.3235 0.53; 2.1415 1.50; 2.1088 3.06; 2.0693 2.13; 1.9871 2.49; 1.8476 0.74; 1.8264 1.44; 1.8184 1.52; 1.7952 1.51; 1.7875 1.53; 1.7662 2.67; 1.7362 3.74; 1.7218 4.03; 1.6837 4.30; 1.6677 2.83; 1.6409 1.91; 1.6328 1.82; 1.6242 1.83; 1.6056 1.81; 1.5722 1.42; 1.5641 1.28; 1.5417 0.57; 1.4071 0.41; 1.2632 3.22; 1.2549 3.25; 1.2314 1.99; 1.2254 1.94; 1.1932 1.69; 1.1753 1.64; 1.1576 0.83; 1.0719 0.61; 1.0447 1.44; 1.0189 1.19; 0.9883 0.45; 0.7780 15.77; 0.7621 16.00; 0.7414 1.58; −0.0002 1.35 |
| 1-51 | [DMSO-$D_6$] 7.6117 0.46; 7.5934 1.32; 7.5740 1.93; 7.5557 1.42; 7.5381 0.48; 7.3069 2.68; 7.2107 1.34; 7.2040 5.75; 7.1829 11.79; 7.1792 12.89; 7.1776 12.89; 7.1738 8.13; 7.1617 5.80; 7.0403 2.98; 7.0230 6.62; 6.9007 5.78; 6.8871 3.34; 5.4383 1.13; 5.3952 4.33; 5.3542 4.38; 5.3115 1.20; 5.2976 0.36; 4.3064 1.34; 4.2744 1.38; 3.9328 1.37; 3.8993 1.37; 3.4838 1.18; 3.4666 2.41; 3.4496 2.62; 3.4325 1.53; 3.4159 0.53; 3.3792 2.18; 3.3621 1.74; 3.3374 3.86; 3.3116 292.13; 3.2880 5.08; 3.2679 1.61; 3.2598 1.71; 3.2488 1.23; 3.2391 2.49; 3.2309 3.43; 3.2215 1.64; 3.2024 1.86; 3.1296 1.93; 3.1120 1.79; 3.0883 1.45; 3.0706 1.29; 2.8495 0.87; 2.8420 0.93; 2.8150 1.62; 2.7851 0.91; 2.5102 13.21; 2.5059 24.79; 2.5014 32.48; 2.4970 22.75; 2.4927 11.05; 2.0699 0.41; 2.0440 1.16; 2.0066 1.78; 1.9635 1.32; 1.7392 0.47; 1.7097 1.07; 1.6864 1.00; 1.6802 0.96; 1.6566 0.40; 1.6493 0.34; 1.5146 0.48; 1.5036 0.45; 1.4845 1.10; 1.4540 1.05; 1.4237 0.42; 1.2883 16.00; 1.2712 15.74; −0.0002 3.98 |
| 1-52 | [DMSO-$D_6$] 8.1450 16.00; 7.9241 0.88; 7.8342 0.33; 7.8301 0.34; 7.7728 2.13; 7.7685 2.39; 7.7542 4.11; 7.7497 4.60; 7.7345 2.55; 7.7303 2.48; 7.7035 1.30; 7.6987 1.27; 7.6901 1.60; 7.6853 2.71; 7.6823 2.22; 7.6714 2.25; 7.6674 2.23; 7.6644 2.75; 7.6595 1.60; 7.6510 1.63; 7.6463 1.35; 7.6221 3.53; 7.6190 3.50; 7.5836 6.54; 7.5806 6.29; 7.4983 5.45; 7.4922 5.33; 7.4598 2.94; 7.4539 2.87; 7.4088 3.30; 7.3968 3.95; 7.3944 4.12; 7.3875 3.63; 7.3830 3.87; 7.3780 6.81; 7.3593 5.87; 7.3104 3.30; 7.2799 0.41; 7.1772 7.65; 7.1594 3.67; 7.0440 3.77; 7.0234 8.21; 6.9281 0.61; 6.9027 7.22; 6.8875 4.01; 5.7458 4.96; 5.4582 1.60; 5.4166 5.55; 5.3715 5.47; 5.3481 0.78; 5.3291 1.57; 4.3715 1.80; 4.3388 1.84; 4.1303 0.35; 4.0392 0.39; 4.0202 0.43; 3.9930 1.81; 3.9598 1.88; 3.8840 0.33; 3.8496 0.33; 3.8245 0.39; 3.7895 0.39; 3.7752 0.35; 3.7579 0.37; 3.7289 0.37; 3.7233 0.37; 3.6965 0.42; 3.6610 0.45; 3.6217 0.54; 3.5969 0.60; 3.5520 0.72; 3.4287 3.21; 3.4096 4.17; 3.3998 5.68; 3.3903 5.36; 3.3708 7.58; 3.3190 2661.98; 3.2498 2.21; 3.2196 0.57; 3.2014 0.46; 3.1642 0.33; 2.8811 1.22; 2.8518 2.09; 2.8243 1.26; 2.6750 1.07; 2.6704 1.30; 2.6657 1.03; 2.5943 0.50; 2.5402 2.29; 2.5101 76.99; 2.5057 139.24; 2.5013 178.61; 2.4969 123.40; 2.4926 59.64; 2.4440 0.40; 2.3322 0.85; 2.3282 1.16; 2.3235 0.84; 2.1585 1.58; 2.1250 3.07; 2.0852 2.03; 2.0692 1.31; 1.9868 0.46; 1.8602 0.71; 1.8300 1.49; 1.8091 1.34; 1.8014 1.27; 1.7781 0.60; 1.7688 0.55; 1.6302 0.69; 1.6093 1.37; 1.6001 1.42; 1.5787 1.36; 1.5704 1.30; 1.5477 0.56; 1.5370 0.50; 1.2365 0.54; −0.0002 12.15 |
| I-55 | [DMSO-$D_6$] 8.2161 0.55; 8.0448 12.22; 8.0245 0.94; 8.0222 1.08; 7.5743 1.29; 7.5700 1.58; 7.5519 2.58; 7.5491 2.43; 7.5351 1.79; 7.5306 2.10; 7.4889 2.95; 7.4846 3.06; 7.4699 3.52; 7.4657 3.40; 7.4413 0.38; 7.4237 15.38; 7.4226 16.00; 7.4168 2.28; 7.4129 1.63; 7.4071 1.54; 7.3832 0.47; 7.3043 2.07; 7.2886 0.59; 7.2762 3.88; 7.2556 3.38; 7.2039 0.40; 7.1915 0.41; 7.1822 0.70; 7.1709 4.73; 7.1574 2.58; 7.1299 2.24; 7.1113 3.88; 7.0945 2.00; 7.0927 2.00; 7.0766 0.42; 7.0550 0.57; 7.0464 0.76; 7.0377 2.42; 7.0213 5.38; 6.9783 0.33; 6.9548 0.49; 6.9007 4.86; 6.8854 3.08; 6.8539 0.53; 6.7244 0.41; 5.7466 1.57; 5.4440 0.74; 5.4010 3.72; 5.3720 3.77; 5.3580 0.73; 5.3465 0.34; 5.3300 0.85; 5.3056 0.36; 5.2957 0.98; 4.9216 9.22; 4.9158 10.09; 4.8789 0.73; 4.8732 0.75; 4.8116 0.32; 4.8058 0.34; 4.3462 1.07; 4.3106 1.10; 4.2628 0.35; 4.2512 0.38; 4.2396 0.39; 4.0218 0.33; 3.9780 1.07; 3.9416 1.11; 3.6973 0.44; 3.6931 0.44; 3.6841 0.58; 3.6723 0.76; 3.6630 0.54; 3.6508 0.35; 3.5793 0.49; 3.5560 2.51; 3.5501 5.43; 3.5442 2.70; 3.5373 0.69; 3.4073 0.79; 3.3931 1.05; 3.3883 1.12; 3.3794 1.79; 3.3697 1.27; 3.3585 1.26; 3.3498 1.63; 3.3074 734.77; 3.2863 8.37; 3.2551 2.26; 3.1387 0.42; 3.0369 0.63; 2.9014 0.88; 2.8763 1.52; 2.8492 0.96; 2.8150 0.33; 2.6740 0.51; 2.6692 0.61; 2.6649 0.47; 2.5744 0.55; 2.5394 0.75; 2.5090 34.19; 2.5047 64.65; 2.5002 85.50; 2.4958 60.67; 2.4915 30.30; 2.3315 0.56; 2.3269 0.72; 2.3224 0.56; 2.2033 0.50; 2.1583 1.06; 2.1246 1.99; 2.0894 1.22; 2.0693 0.92; 2.0330 0.41; 1.9867 0.54; 1.8534 0.51; 1.8246 0.97; 1.8018 0.91; 1.7728 0.47; 1.6391 0.61; 1.6185 1.06; 1.6096 1.07; 1.5879 1.10; 1.5802 0.95; 1.5579 0.63; 1.4151 1.04; 1.4082 6.37; 1.3933 0.47; 1.3889 0.41; 1.3846 0.34; 1.2654 0.63; 1.2499 0.74; 1.2358 1.21; 1.1822 0.32; 1.1747 0.38; 1.1085 0.55; 1.0909 1.03; 1.0735 0.51; 0.0079 0.32; −0.0002 5.93 |
| I-57 | [DMSO-$D_6$] 8.1634 13.11; 8.1472 0.76; 7.5710 4.48; 7.5319 5.69; 7.5073 0.36; 7.4373 0.57; 7.4241 3.82; 7.4040 5.44; 7.4009 5.75; 7.3808 3.84; 7.3282 0.89; 7.3111 3.27; 7.3060 1.88; 7.2835 0.77; 7.1776 11.64; 7.1653 3.74; 7.1379 3.93; 7.0447 3.27; 7.0293 7.89; 7.0152 0.64; 6.9934 0.35; 6.9096 7.23; 6.8935 4.18; 5.4580 1.46; 5.4154 5.09; 5.3913 0.87; 5.3745 5.11; 5.3554 0.72; 5.3319 1.52; 4.3627 1.46; 4.3299 1.58; 4.0564 1.19; 4.0386 3.60; 4.0208 3.65; 4.0030 1.43; 3.9843 1.37; 3.9494 1.66; 3.9175 0.40; 3.8629 2.49; 3.8203 0.37; 3.8073 0.48; 3.5491 0.33; 3.3691 454.41; 3.3559 688.63; 3.2715 3.26; 3.2420 1.92; 3.1943 0.69; 3.1851 0.69; 3.1660 1.21; 3.1448 0.46; 2.8753 1.09; 2.8446 1.91; 2.8179 1.18; 2.6822 0.40; 2.6779 0.81; 2.6733 1.07; 2.6688 0.80; 2.6643 0.39; 2.5434 1.87; 2.5264 3.05; 2.5133 58.45; 2.5088 117.23; 2.5042 155.51; 2.4996 111.90; 2.4951 53.73; 2.3401 0.37; 2.3356 0.77; 2.3309 1.04; 2.3263 0.76; 2.1489 1.33; 2.1120 2.64; 2.0867 1.53; 2.0729 3.43; 1.9891 16.00; 1.8606 0.49; 1.8514 0.59; 1.8303 1.16; 1.8217 1.27; 1.7998 1.17; 1.7909 1.10; 1.7697 0.49; 1.7602 0.45; 1.6289 0.55; 1.6179 0.63; 1.5974 1.18; 1.5885 1.27; 1.5667 1.18; 1.5584 1.13; 1.5367 0.51; 1.5266 0.44; 1.3105 0.53; 1.2439 1.83; 1.2350 1.03; 1.2166 2.36; 1.1930 4.45; 1.1752 8.86; 1.1574 4.35; −0.0002 1.64 |

-continued

| Ex. | NMR peak list data |
|---|---|
| I-59 | [DMSO-D$_6$] 8.4936 9.05; 7.3144 1.47; 7.1811 3.27; 7.1608 1.62; 7.0612 1.55; 7.0551 1.88; 7.0476 2.64; 7.0404 6.28; 7.0247 4.40; 7.0209 3.64; 7.0058 1.19; 6.9989 0.84; 6.9846 0.66; 6.9041 3.26; 6.8889 1.86; 5.7472 1.75; 5.4671 0.69; 5.4239 2.46; 5.3787 2.48; 5.3356 0.70; 4.5903 0.34; 4.4152 10.64; 4.3748 0.80; 4.3413 0.86; 4.0390 0.34; 4.0212 0.44; 4.0039 0.78; 3.9676 0.78; 3.7096 0.47; 3.7057 0.36; 3.6980 0.55; 3.6960 0.58; 3.6810 0.60; 3.6715 0.37; 3.6677 0.41; 3.4979 0.45; 3.4861 0.42; 3.4746 0.85; 3.4639 1.03; 3.4561 0.61; 3.4462 0.82; 3.4364 1.23; 3.4268 0.75; 3.4179 0.57; 3.4087 0.72; 3.3982 0.47; 3.3009 297.63; 3.2772 7.56; 2.9051 0.55; 2.8768 0.95; 2.8471 0.57; 2.6732 0.49; 2.6686 0.69; 2.6639 0.51; 2.5386 1.04; 2.5084 39.69; 2.5041 72.43; 2.4997 93.44; 2.4953 65.59; 2.4910 32.05; 2.3452 0.39; 2.3310 0.53; 2.3263 0.69; 2.3219 0.51; 2.2393 15.38; 2.2068 0.36; 2.1885 0.79; 2.1850 0.78; 2.1726 0.67; 2.1483 1.40; 2.1128 1.01; 2.0768 16.00; 1.9866 1.34; 1.8627 0.63; 1.8541 0.66; 1.8330 0.61; 1.8258 0.57; 1.6385 0.63; 1.6303 0.65; 1.6093 0.60; 1.5996 0.58; 1.2368 0.78; 1.1925 0.38; 1.1747 0.68; 1.1570 0.36; 0.0079 0.62; −0.0002 11.73; −0.0085 0.51 |
| I-60 | [DMSO-D$_6$] 8.3299 0.40; 7.7755 6.73; 7.6623 0.33; 7.3056 1.04; 7.2679 0.47; 7.1722 2.36; 7.1569 1.27; 7.0388 1.16; 7.0317 0.56; 7.0211 2.58; 6.8993 2.66; 6.8854 1.32; 5.7474 1.35; 5.4566 0.56; 5.4132 1.63; 5.3601 1.71; 5.3176 0.60; 5.2956 0.47; 5.2746 0.36; 4.3544 0.44; 4.3432 0.59; 4.3127 0.63; 3.9748 0.57; 3.9354 0.78; 3.9197 0.40; 3.8887 1.04; 3.8676 16.00; 3.6860 0.35; 3.6721 0.45; 3.6627 0.36; 3.4247 0.45; 3.3792 1.14; 3.3008 1113.92; 3.2777 19.21; 3.2076 0.63; 3.1878 0.59; 3.1744 0.49; 3.1672 0.43; 3.1486 0.39; 2.8868 0.54; 2.8592 0.74; 2.8383 0.35; 2.8211 0.50; 2.6925 2.76; 2.6736 4.08; 2.6688 3.15; 2.6642 2.17; 2.6598 1.18; 2.6255 0.37; 2.6134 0.41; 2.6090 0.44; 2.5388 4.71; 2.5085 159.43; 2.5042 286.60; 2.4997 366.70; 2.4953 252.97; 2.4909 121.25; 2.4240 0.76; 2.3732 0.38; 2.3676 0.37; 2.3563 0.40; 2.3312 2.00; 2.3265 2.52; 2.3218 1.83; 2.1289 0.65; 2.1226 0.64; 2.0845 4.97; 2.0694 4.57; 1.9864 0.54; 1.7881 0.59; 1.7521 0.51; 1.5951 2.86; 1.5634 2.25; 1.3991 0.42; 1.2368 0.73; 1.1747 0.51; 1.1577 0.50; 1.1150 2.15; 1.0951 1.38; 1.0060 0.57; 0.9835 0.98; 0.9616 0.73; 0.9555 0.77; 0.8901 0.49; 0.0080 2.80; −0.0002 51.71; −0.0084 2.10; −0.1497 0.32 |
| I-61 | [DMSO-D$_6$] 7.7676 6.50; 7.3003 0.96; 7.1671 2.26; 7.1545 1.10; 7.0337 1.12; 7.0185 2.56; 6.9655 0.92; 6.9483 1.70; 6.9263 1.19; 6.9067 2.05; 6.8964 2.35; 6.8827 1.36; 6.8246 1.41; 6.8057 0.97; 5.4374 0.51; 5.3940 1.76; 5.3536 1.74; 5.3104 0.49; 4.3147 0.63; 4.2815 0.61; 4.0985 4.92; 4.0568 0.38; 4.0389 0.97; 4.0211 1.02; 4.0034 0.36; 3.9443 0.64; 3.9025 16.00; 3.7095 0.35; 3.6962 0.36; 3.6808 0.38; 3.4982 0.39; 3.4752 0.58; 3.4640 0.53; 3.4527 0.53; 3.4443 0.52; 3.4166 0.67; 3.4003 0.89; 3.3047 1218.33; 3.2814 18.99; 3.2131 0.65; 3.0832 0.49; 2.8555 0.43; 2.8231 0.72; 2.7949 0.49; 2.6736 1.46; 2.6690 1.91; 2.6643 1.44; 2.6602 0.80; 2.6131 0.39; 2.5390 3.14; 2.5087 109.72; 2.5044 200.01; 2.4999 258.25; 2.4955 180.12; 2.4912 86.91; 2.3311 1.32; 2.3265 1.73; 2.3220 1.17; 2.3174 0.62; 2.2191 10.31; 2.1997 10.49; 2.0828 0.52; 2.0691 1.44; 2.0478 0.92; 2.0120 0.61; 1.9867 4.02; 1.7607 0.47; 1.7301 0.42; 1.5373 0.48; 1.5301 0.45; 1.5074 0.45; 1.3985 1.31; 1.2364 0.52; 1.1926 1.17; 1.1748 2.17; 1.1570 1.12; 0.8903 0.37; 0.0079 1.13; −0.0002 20.73; −0.0084 0.91 |
| I-62 | [DMSO-D$_6$] 8.6244 16.00; 8.4920 0.52; 8.0955 4.59; 8.0545 6.27; 7.8260 6.63; 7.7849 4.95; 7.6205 0.66; 7.6038 1.48; 7.5993 1.46; 7.5828 2.83; 7.5663 1.51; 7.5618 1.74; 7.5454 0.79; 7.3139 2.67; 7.2904 4.80; 7.2679 7.01; 7.2461 3.91; 7.1806 5.94; 7.1610 2.97; 7.0782 0.35; 7.0473 3.04; 7.0250 6.55; 6.9047 5.84; 6.8891 3.33; 5.4687 1.21; 5.4263 4.20; 5.3779 4.28; 5.3351 1.26; 5.2959 0.43; 4.3852 1.32; 4.3523 1.40; 4.0572 1.04; 4.0394 3.11; 4.0216 3.52; 4.0039 2.14; 3.9745 1.38; 3.5682 0.36; 3.4991 0.69; 3.4899 1.12; 3.4799 0.94; 3.4707 1.40; 3.4614 2.23; 3.4520 1.49; 3.4426 1.16; 3.4330 1.50; 3.4252 1.10; 3.4115 0.90; 3.3151 1941.32; 3.1796 0.72; 3.1408 0.67; 2.9072 1.09; 2.8782 1.77; 2.8506 1.14; 2.8303 0.33; 2.6956 0.39; 2.6795 0.76; 2.6749 1.36; 2.6702 1.76; 2.6658 1.33; 2.6612 0.76; 2.5402 3.49; 2.5233 8.22; 2.5099 97.98; 2.5056 183.21; 2.5011 241.25; 2.4967 173.04; 2.4923 86.93; 2.3804 0.38; 2.3491 0.35; 2.3323 1.45; 2.3278 1.79; 2.3233 1.42; 2.1993 1.36; 2.1620 2.48; 2.1238 1.57; 2.0851 0.33; 2.0694 2.27; 1.9871 13.50; 1.9085 0.86; 1.8950 0.53; 1.8854 0.62; 1.8636 1.17; 1.8565 1.25; 1.8330 1.17; 1.8256 1.14; 1.8047 0.55; 1.7953 0.50; 1.6675 0.61; 1.6469 1.16; 1.6376 1.25; 1.6157 1.15; 1.6072 1.11; 1.5860 0.52; 1.5764 0.47; 1.3984 0.42; 1.2355 0.71; 1.1930 3.81; 1.1753 7.51; 1.1575 3.69; 0.0079 0.46; −0.0002 9.48; −0.0085 0.45 |
| I-63 | [DMSO-D$_6$] 8.1046 3.68; 7.3058 0.73; 7.2811 0.75; 7.2622 1.16; 7.2431 1.07; 7.1725 1.68; 7.1582 0.89; 7.1374 2.66; 7.1301 1.34; 7.1186 1.96; 7.0904 3.04; 7.0561 2.91; 7.0392 0.87; 7.0221 1.91; 7.0166 1.02; 6.9007 1.65; 6.8863 0.91; 5.4029 1.36; 5.3696 1.32; 4.3529 0.40; 4.3211 0.42; 4.0573 0.42; 4.0395 1.20; 4.0217 1.22; 4.0038 0.46; 3.9768 0.38; 3.9445 0.42; 3.3995 0.60; 3.3902 0.62; 3.3808 0.83; 3.3713 1.19; 3.3608 1.19; 3.3132 179.92; 3.2393 0.40; 2.8479 0.49; 2.5398 0.71; 2.5096 16.90; 2.5053 30.21; 2.5009 38.39; 2.4966 26.71; 2.4923 12.94; 2.1841 0.47; 2.1360 16.00; 2.1043 0.77; 2.0695 0.51; 1.9870 5.09; 1.8196 0.33; 1.5817 0.32; 1.3982 0.54; 1.1929 1.40; 1.1752 2.76; 1.1573 1.35; −0.0002 0.40 |
| I-64 | [DMSO-D$_6$] 11.4444 4.39; 11.1901 0.81; 9.8995 0.61; 9.0748 0.34; 8.6602 0.56; 7.9819 0.34; 7.8239 1.45; 7.7835 1.56; 7.6641 0.87; 7.6598 0.95; 7.6444 1.02; 7.6404 0.97; 7.6203 2.89; 7.6118 0.37; 7.6004 2.97; 7.5921 0.47; 7.5795 0.71; 7.5283 0.70; 7.4820 0.52; 7.4651 1.27; 7.4613 1.12; 7.4428 1.44; 7.4257 0.56; 7.4216 0.56; 7.3257 0.38; 7.3187 0.66; 7.3051 0.81; 7.2482 0.43; 7.2196 1.03; 7.2109 2.00; 7.1990 1.13; 7.1919 2.15; 7.1884 2.39; 7.1714 2.69; 7.1462 0.37; 7.0881 0.41; 7.0802 1.14; 7.0690 0.56; 7.0608 2.03; 7.0526 1.09; 7.0426 1.41; 7.0388 1.54; 7.0349 2.49; 7.0276 1.94; 6.9091 2.84; 6.8913 0.96; 6.3120 1.53; 6.2723 1.45; 6.1958 0.37; 6.1870 0.76; 6.1688 0.61; 5.7851 0.68; 5.7646 0.79; 5.7573 1.82; 5.7375 0.50; 5.4713 0.46; 5.4445 0.43; 5.4276 1.10; 5.4027 1.31; 5.3905 0.78; 5.3807 1.73; 5.3669 1.21; 5.3376 0.51; 5.3260 0.44; 5.0197 0.55; 5.0141 0.57; 4.9042 2.67; 4.8986 2.60; 4.8296 0.71; 4.8208 0.86; 4.8045 2.17; 4.7984 2.25; 4.7687 0.39; 4.7639 0.42; 4.3678 0.52; 4.3440 0.75; 4.3274 0.56; 4.0553 0.78; 4.0374 2.23; 4.0197 2.26; 4.0018 0.77; 3.9550 0.68; 3.8317 0.39; 3.8045 0.41; 3.7879 0.78; 3.7614 0.68; 3.7015 0.68; 3.6923 0.45; 3.6806 0.63; 3.6583 0.34; 3.6384 0.38; 3.6124 0.86; 3.6067 2.11; 3.6010 0.87; 3.5675 0.69; 3.5118 1.03; 3.5061 2.16; 3.5001 0.92; 3.4144 0.39; 3.4015 0.59; 3.3913 0.99; 3.3795 1.66; 3.3470 1964.81; 3.3250 5.70; 3.2972 1.40; 3.2599 1.04; 3.2431 0.82; 3.2282 0.61; 3.2018 0.33; 2.8662 0.42; 2.8307 |

| Ex. | NMR peak list data |
|---|---|
| | 0.70; 2.8039 0.50; 2.6768 1.01; 2.6718 1.53; 2.6673 1.15; 2.5421 0.78; 2.5251 2.65; 2.5206 3.84; 2.5112 86.20; 2.5071 166.76; 2.5028 232.18; 2.4986 160.26; 2.4944 80.12; 2.4562 0.37; 2.3342 1.12; 2.3295 1.39; 2.3251 1.04; 2.1407 0.58; 2.1029 1.02; 2.0746 16.00; 2.0457 0.53; 1.9892 10.59; 1.8258 0.58; 1.7937 0.54; 1.7670 0.43; 1.7581 0.43; 1.5938 0.34; 1.5805 0.39; 1.5736 0.52; 1.5644 0.52; 1.5448 0.62; 1.2346 0.73; 1.1922 2.79; 1.1744 5.96; 1.1567 2.76; 0.0079 0.59; −0.0002 20.96; −0.0087 0.56 |
| I-65 | [CD$_3$CN] 8.0859 4.04; 7.8317 3.92; 7.8312 3.99; 7.6910 0.33; 7.6866 0.33; 7.6476 1.02; 7.6434 1.12; 7.6283 1.07; 7.6241 1.11; 7.5577 0.89; 7.5556 1.56; 7.5534 0.79; 7.5395 0.82; 7.5368 0.92; 7.5350 0.83; 7.5323 0.74; 7.5185 0.85; 7.5139 0.73; 7.1323 1.29; 7.1122 1.16; 7.0765 0.89; 7.0741 0.85; 7.0575 1.35; 7.0557 1.19; 7.0390 0.79; 7.0366 0.71; 7.0124 0.43; 7.0047 0.33; 6.9912 0.42; 6.9858 0.49; 6.9674 0.35; 6.9022 1.35; 6.3609 2.00; 5.4215 10.07; 5.0391 1.26; 5.0021 0.57; 3.9498 0.56; 3.8868 16.00; 3.8073 4.63; 3.7942 1.21; 3.3556 0.49; 3.3456 0.35; 3.3381 0.57; 3.3281 0.99; 3.3181 0.58; 3.3108 0.41; 3.3009 0.58; 3.2899 0.44; 2.2310 12.74; 2.2294 10.23; 2.1955 0.52; 2.1638 0.59; 2.0857 0.36; 1.9912 41.03; 1.9596 1.75; 1.9524 1.81; 1.9428 7.37; 1.9367 4.93; 1.9307 19.09; 1.9246 33.26; 1.9184 43.17; 1.9123 29.21; 1.9061 14.83; 1.7469 0.34; 1.2802 0.39; 1.2203 0.34; 1.2026 0.74; 1.1847 0.39; 0.9161 0.44; −0.0001 4.75 |

The intensity of sharp signals correlates with the height of the signals in a printed example of an NMR spectrum in cm and shows the true ratios of the signal intensities. In the case of broad signals, a plurality of peaks or the middle of the signal and their relative intensities compared to the most intensive signal in the spectrum may be shown.

The lists of the $^1$H-NMR peaks are similar to the classic $^1$H-NMR prints and thus usually comprise all peaks listed in classic NMR interpretations.

In addition, like classic $^1$H-NMR prints, they may show solvent signals, signals of stereoisomers of the target compounds, which are likewise part of the subject matter of the invention, and/or peaks of impurities.

In the list of compound signals in the delta range of solvents and/or water, in our lists of $^1$H-NMR peaks the usual solvent peaks, for example peaks of DMSO in DMSO-d$_6$ and the peak of water, which usually on average have a high intensity, are shown.

Usually, on average, the peaks of stereoisomers of the target compounds and/or peaks of impurities have a lower intensity than the peaks of the target compounds (for example with a purity of >90%).

Such stereoisomers and/or impurities may be typical for the preparation process in question. Thus, their peaks may help to identify any reproduction of our preparation process using "by-product fingerprints".

If required, an expert calculating the peaks of the target compounds with known methods (MestreC, ACD simulation, but also using empirically evaluated expected values) can isolate the peaks of the target compounds, using, if appropriate, additional intensity filters. This isolation would be similar to the corresponding peak picking of the classic $^1$H-NMR interpretation.

Use Examples

Example A

*Phytophthora* Test (Tomato)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Phytophthora infestans* and then remain at 100% relative humidity and 22° C. for 24 h. The plants are then placed in a climatized cabin at about 96% relative atmospheric humidity and a temperature of about 20° C.

Evaluation is carried out 7 days after the inoculation. 0% means an efficacy which corresponds to that of the control, whereas an efficacy of 100% means that no infection is observed.

In this test, the following compounds according to the invention I-2, I-3, I-4, I-5, I-6, I-7, I-8, I-11, I-13, I-14, I-15, I-17, I-18, I-19, I-20 and I-21 show, at an active compound concentration of 500 ppm, an efficacy of 70% or more.

Furthermore, in this test the following compounds show, at an active compound concentration of 500 ppm, an efficacy of 70% or more, where the efficacies reported in brackets are observed for specific compounds: I-16 (80%), I-22 (100%), I-23 (70%), I-24 (94%), I-25 (100%), I-29 (100%), I-30 (95%), I-33 (95%), I-34 (95%), I-35 (95%), I-36 (100%), I-37 (95%), I-38 (95%), I-39 (90%), I-41 (95%), I-42 (100%), I-43 (90%), I-44 (95%), I-45 (95%), I-46 (95%), I-47 (94%), I-48 (94%), I-49 (90%), I-50 (95%), I-51 (98%), I-52 (98%), I-53 (90%), I-54 (85%), I-55 (98%), I-57 (98%), I-60 (95%), I-61 (95%), I-65 (93%).

Example B

*Plasmopara* Test (Grapevine)/Protective

Solvent: 24.5 parts by weight of acetone
24.5 parts by weight of dimethylacetamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at about 20° C. and 100% relative atmospheric humidity for 1 day. The plants are then placed in a greenhouse at about 21° C. and about 90% atmospheric humidity for 4 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the following compounds according to the invention I-3, I-11, I-13, I-14, I-16, I-17, I-18, I-19, I-20, I-21 show, at an active compound concentration of 100 ppm, an efficacy of 70% or more.

Furthermore, in this test the following compounds show, at an active compound concentration of 500 ppm, an efficacy of 70% or more, where the efficacies reported in brackets are observed for specific compounds: I-22 (100%), I-24 (100%), I-25 (96%), I-29 (95%), I-30 (85%), I-33 (89%), I-34 (84%), I-35 (89%), I-36 (96%), I-42 (90%), I-43 (100%), I-44 (74%), I-45 (100%), I-46 (100%), I-49 (79%), I-50 (93%), I-51 (100%), I-52 (94%), I-53 (76%), I-55 (100%), I-57 (91%).

The invention claimed is:

1. A compound of formula (I')

wherein

A represents phenyl which may contain up to two substituents, wherein the substituents independently of one another are selected from $R^2$, and $R^2$ represents: methyl, ethyl, iodine, chlorine, bromine, fluorine, methoxy, ethoxy, difluoromethyl, or trifluoromethyl, or A is A', which represents pyrazol-1-yl, which may contain up to two substituents at carbon, wherein the substituents independently of one another are selected from $R^3$, and $R^3$ represents methyl, difluoromethyl, or trifluoromethyl, T is selected from the group consisting of *—C(=O)CH$_2$—#, *—C(=O)CH$_2$C(CH$_3$)$_2$—#, *—C(=O)CH$_2$CH$_2$—#, *—C(=O)CH=CH—#, *—C≡CC(=O)—#, *—CH=CHC(=O)—#, *—CH$_2$CH$_2$C(=O)—#, *—C(=NOCH$_3$)CH$_2$—#, *—CH=CHC(=NOH)—#, *—C(Cl)=CHC(=O)—#, and *—CH(CH$_3$)CH$_2$C(=O)—#, where the bond identified by * is attached directly to G and where the bond identified by # is attached directly to $R^1$, $R^1$ is selected from the group consisting of $R^1_a$, $R^1_b$, $R^1_c$, $R^1_d$, $R^1_e$, and $R^1_f$, wherein $R^1_a$ represents 1,1-dimethylethyl, $R^1_b$ represents cyclohexyl, cyclopentyl, 2-methylcyclohexyl, 3-methylcyclohexyl, or 4-methylcyclohexyl, $R^1_c$ represents cyclohex-3-en-1-yl or cyclohex-2-en-1-yl, $R^1_d$ represents phenyl that may contain up to two substituents, wherein the substituents independently of one another are selected from $R^{12}$ and $R^{12}$ represents: chlorine, fluorine, bromine, iodine, methyl, methoxy, ethoxy, trifluoromethyl, difluoromethyl, 2-propenyloxy, 2-propynyloxy or phenyl, $R^1_e$ represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl, or indan-5-yl, $R^1_f$ represents furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, pyridin-2-yl, pyridin-3-yl, pyridin-4-yl, pyridazin-3-yl, pyridazin-4-yl, pyrimidin-2-yl, pyrimidin-4-yl, or pyrimidin-5-yl, or an agrochemically active salt thereof.

2. The compound of claim 1, wherein

A is A', which represents pyrazol-1-yl, which may contain up to two substituents at carbon, wherein the substituents independently of one another are selected from $R^3$, and $R^3$ represents methyl, difluoromethyl, or trifluoromethyl.

3. The compound of claim 1, wherein

A represents phenyl which may contain up to two substituents, wherein the substituents independently of one another are selected from $R^2$, and $R^2$ represents: methyl, ethyl, iodine, chlorine, bromine, fluorine, methoxy, ethoxy, difluoromethyl, or trifluoromethyl.

4. The compound of claim 2, wherein $R^1$ is selected from the group consisting of cyclohexyl, phenyl, 2-methoxyphenyl, 4-methoxyphenyl, 2-ethoxyphenyl, naphthalen-1-yl, tert-butyl, thiophen-2-yl, furan-2-yl, 2-chlorophenyl, 2,4-dichlorophenyl, 2-bromophenyl, 2,6-difluorophenyl, 2-iodophenyl, 2-methylphenyl, 3-methylphenyl, cyclopentyl, 2-fluoro-4-methoxyphenyl, 2-bromo-4-fluorphenyl, 2,6-dimethoxyphenyl, 2-methylcyclohexyl, 2-(prop-2-yn-1-yloxy)phenyl, 2,6-dichlorophenyl, 2,6-dimethylphenyl, 2,4,6-trifluorophenyl, 2-chloro-5-fluorophenyl, 2-chloro-6-fluorophenyl, 4-fluorophenyl, 3-fluorophenyl, and 2-fluorophenyl.

5. The compound of claim 3, wherein $R^1$ is selected from the group consisting of cyclohexyl, phenyl, 2-methoxyphenyl, 4-methoxyphenyl, 2-ethoxyphenyl, naphthalen-1-yl, tert-butyl, thiophen-2-yl, furan-2-yl, 2-chlorophenyl, 2,4-dichlorophenyl, 2-bromophenyl, 2,6-difluorophenyl, 2-iodophenyl, 2-methylphenyl, 3-methylphenyl, cyclopentyl, 2-fluoro-4-methoxyphenyl, 2-bromo-4-fluorphenyl, 2,6-dimethoxyphenyl, 2-methylcyclohexyl, 2-(prop-2-yn-1-yloxy)phenyl, 2,6-dichlorophenyl, 2,6-dimethylphenyl, 2,4,6-trifluorophenyl, 2-chloro-5-fluorophenyl, 2-chloro-6-fluorophenyl, 4-fluorophenyl, 3-fluorophenyl, and 2-fluorophenyl.

6. The compound of claim 1, wherein

T is selected from the group consisting of *—C(=O)CH$_2$—#, *—C(=O)CH$_2$C(CH$_3$)$_2$—#, *—C(=O)CH$_2$CH$_2$—#, *—C(=O)CH=CH—#, *—C≡CC(=O)—#, *—CH=CHC(=O)—#, *—CH$_2$CH$_2$C(=O)—#, *—C(=NOCH$_3$)CH$_2$—#, and *—CH=CHC(=NOH)—#.

7. The compound of claim 1, wherein

A is selected from the group consisting of 3,5-bis(difluoromethyl)-1H-pyrazol-1-yl, 5-methyl-3-(trifluoromethyl)-1H-pyrazol-1-yl, 2,5-dimethylphenyl, and 2-methyl-5-chlorophenyl, and $R^1$ is selected from the group consisting of cyclohexyl, phenyl, 2-methoxyphenyl, 4-methoxyphenyl, 2-ethoxyphenyl, naphthalen-1-yl, tert-butyl, thiophen-2-yl, furan-2-yl, 2-chlorophenyl, 2,4-dichlorophenyl, 2-bromophenyl, 2,6-difluorophenyl, 2-iodophenyl, 2-methylphenyl, 3-methylphenyl, cyclopentyl, 2-fluoro-4-methoxyphenyl, 2-bromo-4-fluorphenyl, 2,6-dimethoxyphenyl, 2-methylcyclohexyl, 2-(prop-2-yn-1-yloxy)phenyl, 2,6-dichlorophenyl, 2,6-dimethylphenyl, 2,4,6-trifluorophenyl, 2-chloro-5-fluorophenyl, 2-chloro-6-fluorophenyl, 4-fluorophenyl, 3-fluorophenyl, and 2-fluorophenyl.

8. The compound of claim 7, wherein A is 3,5-bis(difluoromethyl)-1H-pyrazol-1-yl.

9. The compound of claim 7, wherein A is 5-methyl-3-(trifluoromethyl)-1H-pyrazol-1-yl.

10. The compound of claim 7, wherein A is 2,5-dimethylphenyl.

11. The compound of claim 7, wherein A is 2-methyl-5-chlorophenyl.

12. The compound of claim 7, wherein
A is 5-methyl-3-(trifluoromethyl)-1H-pyrazol-1-yl, T is *—C≡CC(=O)—#, and $R^1$ is naphthalen-1-yl.

13. A composition comprising from 0.05% to 99% by weight of at least one compound of claim 1, and at least one extender, at least one surfactant, or a combination thereof.

14. The composition of claim 13, wherein the composition is effective in controlling phytopathogenic harmful fungi *Phytophthora infestans* or *Plasmopara viticola*.

15. A composition comprising from 0.05% to 99% by weight of at least one compound of claim 2, and at least one extender, at least one surfactant, or a combination thereof.

16. The composition of claim 15, wherein the composition is effective in controlling phytopathogenic harmful fungi *Phytophthora infestans* or *Plasmopara viticola*.

17. A composition comprising from 0.05% to 99% by weight of at least one compound of claim 3, and at least one extender, at least one surfactant, or a combination thereof.

18. The composition of claim 17, wherein the composition is effective in controlling phytopathogenic harmful fungi *Phytophthora infestans* or *Plasmopara viticola*.

19. A composition comprising from 0.05% to 99% by weight of at least one compound of claim 12, and at least one extender, at least one surfactant, or a combination thereof.

20. The composition of claim 19, wherein the composition is effective in controlling phytopathogenic harmful fungi *Phytophthora infestans* or *Plasmopara viticola*.

* * * * *